(12) United States Patent
Barden et al.

(10) Patent No.: US 8,420,640 B2
(45) Date of Patent: Apr. 16, 2013

(54) METHODS OF TREATING AMYLOID DISEASE USING ANALOGS OF 1-(4-NITROPHENYL) PIPERAZINE

(75) Inventors: Christopher J. Barden, Lakeside (CA); Michael D. Carter, Toronto (CA); Mark A. Reed, Hubley (CA); Donald F. Weaver, Halifax (CA); Arun Yadav, Halifax (CA); Shengguo Sun, Halifax (CA)

(73) Assignee: Treventis Corporation, Bernville, PA (US)

( * ) Notice: Subject to any disclaimer, the term of this patent is extended or adjusted under 35 U.S.C. 154(b) by 0 days.

(21) Appl. No.: 13/060,939

(22) PCT Filed: Aug. 28, 2009

(86) PCT No.: PCT/US2009/055377
§ 371 (c)(1),
(2), (4) Date: May 23, 2011

(87) PCT Pub. No.: WO2010/025375
PCT Pub. Date: Mar. 4, 2010

(65) Prior Publication Data
US 2011/0218200 A1  Sep. 8, 2011

Related U.S. Application Data

(60) Provisional application No. 61/092,845, filed on Aug. 29, 2008.

(51) Int. Cl.
*A61K 31/535* (2006.01)
*C07D 295/00* (2006.01)

(52) U.S. Cl.
USPC .................. 514/235.8; 514/255.01; 544/391; 544/395

(58) Field of Classification Search .............. 514/235.8, 514/255.01; 544/391, 395
See application file for complete search history.

(56) References Cited

U.S. PATENT DOCUMENTS 5,959,411 A     9/1999  Veldman
5,981,168 A  *  11/1999 Reiner et al. ................ 435/4
2003/0191164 A1  10/2003 Hirano et al.
2004/0220235 A1  11/2004 Augelli-Szafran et al.
2004/0229889 A1  11/2004 Urano et al.
2005/0014812 A1   1/2005 Hayashida et al.
2007/0010573 A1   1/2007 Kong et al.
2008/0132459 A1   6/2008 Moradei et al.
2009/0240052 A1   9/2009 Yokotani et al.

FOREIGN PATENT DOCUMENTS

| EP | 0860098 | 8/1998 |
|---|---|---|
| EP | 1300398 | 4/2003 |
| EP | 1820795 | 8/2007 |
| WO | WO 0076489 | 12/2000 |
| WO | 02/088101 | 11/2002 |
| WO | WO 2004063169 | 7/2004 |
| WO | WO 2004108686 | 12/2004 |
| WO | WO 2005/014563 | 2/2005 |
| WO | 2005/030705 | 4/2005 |
| WO | WO 2005030705 | 4/2005 |
| WO | 2006/066133 | 6/2006 |
| WO | 2007/061880 | 5/2007 |
| WO | 2007/061978 | 5/2007 |
| WO | 2007/118137 | 10/2007 |
| WO | 2008/010985 | 1/2008 |
| WO | 2009/002495 | 12/2008 |
| WO | 2009/020589 | 2/2009 |
| WO | 2010/009139 | 1/2010 |
| WO | 2010-014611 | 2/2010 |

OTHER PUBLICATIONS

Bischoff et al. CAS: 150: 77715, 2008.*
Blakey et al. CAS: 22: 7966, 1928.*
Banus et al. CAS: 16:12259, 1922.*
Baudoin, O., et al., "Synthesis and Biological Evaluation of A-Ring Biaryl-Carbamate Analogues of Rhazinilam," Bioorganic & Medicinal Chemistry, vol. 10, Issue 11, Nov. 2002, pp. 3395-3400.
Perissutti, E. et al., "Design and Synthesis of Potential β-sheet Nucleators via Suzuki Coupling Reaction," Tetrahedron, vol. 63, Issue 51, Dec. 17, 2007, pp. 12779-12785.
Ono, K., et al., "Potent Anti-Amyloidogenic and Fibril-Destabilizing Effects of Polyphenols in Vitro: Implications for the Prevention and Therapeutics of Alzheimer's Disease," Journal of Neurochemistry, vol. 87, Issue 1, pp. 172-181, Oct. 2003.
Extended European Search report issued in corresponding application PCT/US2009/055377, dated May 4, 2012.
International Search Report issued in connection with corresponding International Application No. PCT/US2009/055377, 2009.

* cited by examiner

*Primary Examiner* — Rei-tsang Shiao
(74) *Attorney, Agent, or Firm* — Davidson, Davidson & Kappel, LLC

(57) ABSTRACT

The present invention is directed to compounds that inhibit amyloid aggregation and methods of treatment therewith.

22 Claims, 6 Drawing Sheets

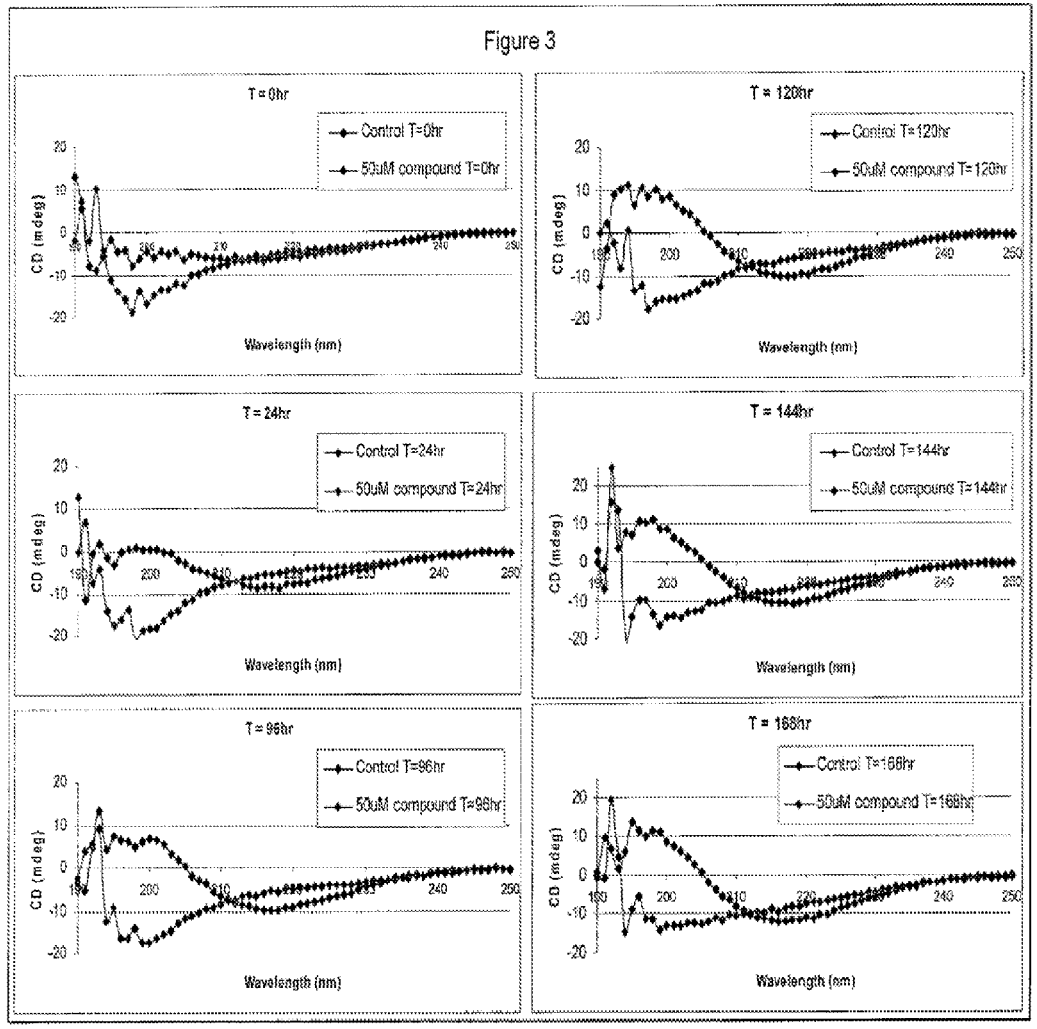

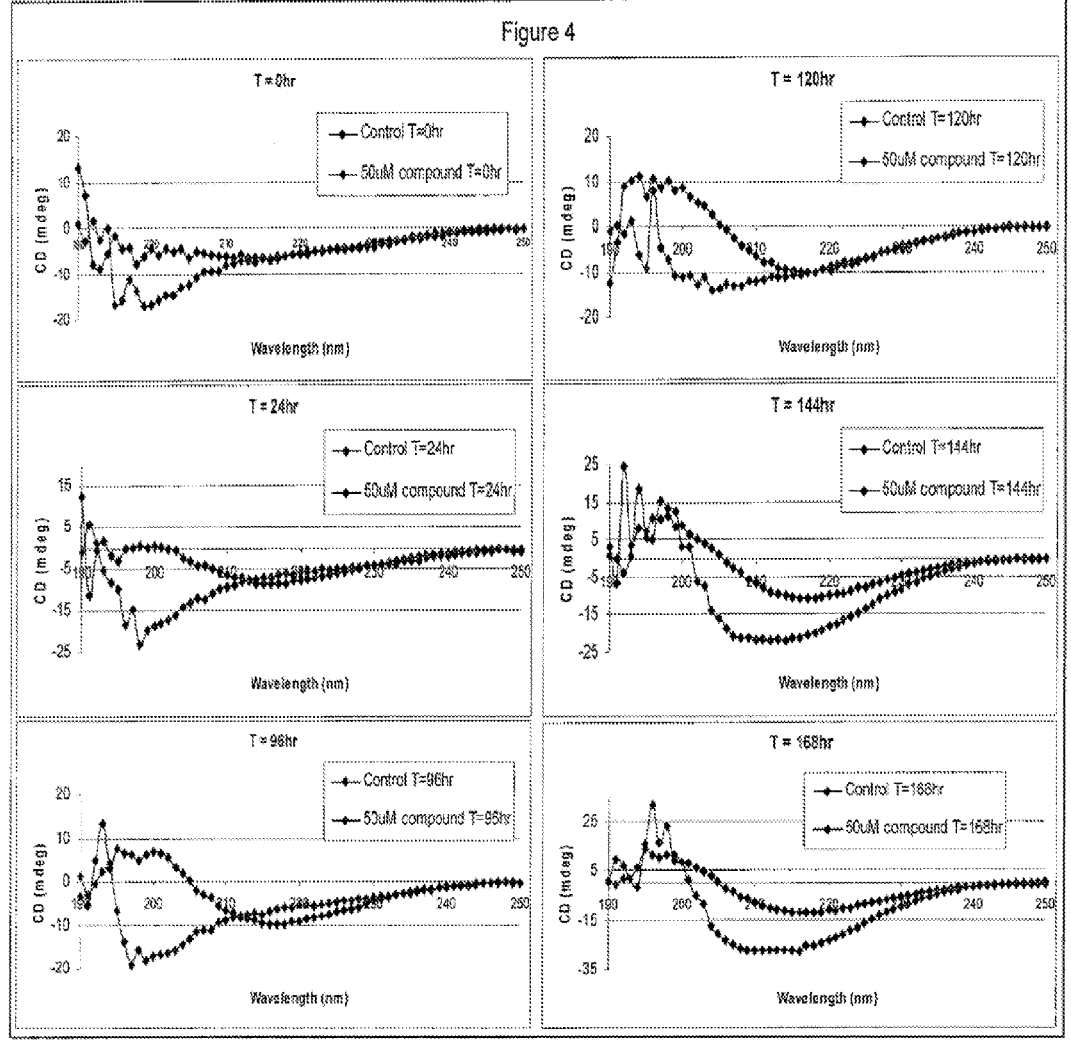

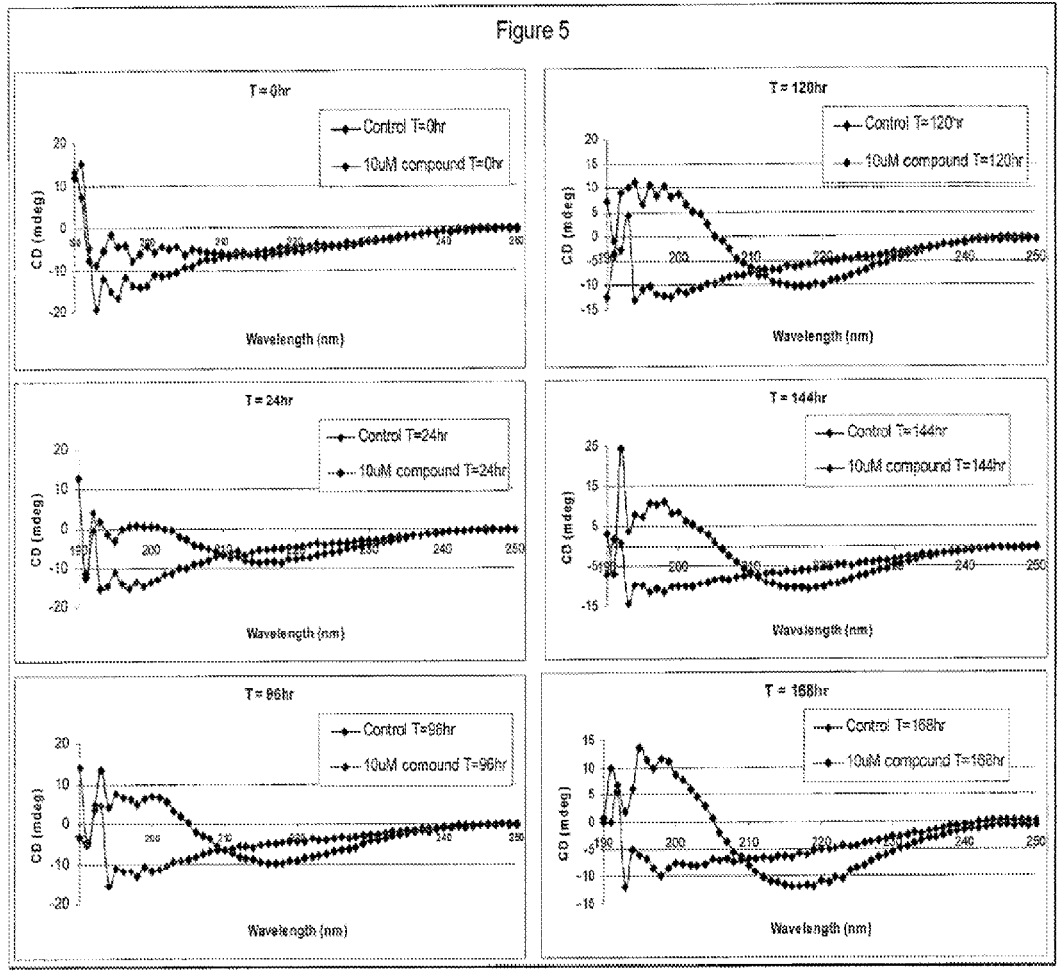

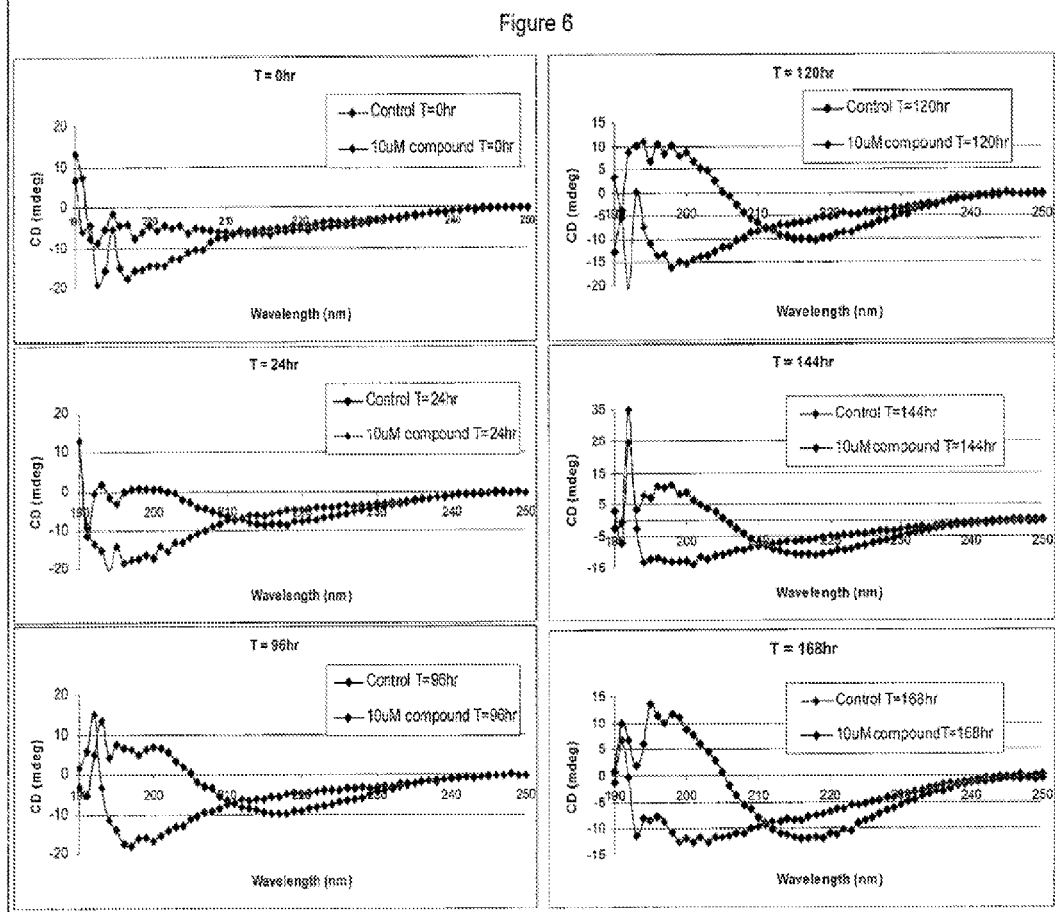

METHODS OF TREATING AMYLOID DISEASE USING ANALOGS OF 1-(4-NITROPHENYL) PIPERAZINE

This application is a National Stage of International Application No. PCT/US2009/055377, filed Aug. 28, 2009, which claims the benefit of U.S. Provisional Patent Application Ser. No. 61/092,845, entitled "Methods of treating amyloid disease using analogs of 1-(4-nitrophenyl)piperazine, filed Aug. 29, 2008; and U.S. Provisional Patent Application Ser. No. 61/092,826, entitled "Methods of identifying inhibitors of amyloid protein aggregation", filed Aug. 29, 2008, the disclosures of which are hereby incorporated by reference in their entirety.

BACKGROUND OF INVENTION

The build-up of amyloid proteins in living tissue, a condition known as amyloidosis, is either the cause or a major factor in the pathology of many so-called amyloid diseases, for example Alzheimer's, Parkinson's, Huntington's, and prion diseases. Historically, aggregations of protein were classified as amyloid if they displayed apple-green birefringence under polarized light when stained with the dyes Congo red or Thioflavin T (ThT) (Sipe and Cohen, 2000, J. Struct. Biol. 130:88-98). That definition of amyloid has been expanded in modern times to apply to any polypeptide which can polymerize in a cross-β sheet conformation in vitro or in vivo, regardless of sequence (Xu, 2007, Amyloid 14:119-31). Certain types of amyloidosis may occur principally in the central nervous system, as with aggregation of beta-amyloid protein in Alzheimer's Disease, alpha-synuclein in Parkinson's Disease, huntingtin protein in Huntington's Disease, and prion protein in Creutzfeldt-Jacob and other prion diseases. Other types of amyloidosis are systemic in nature, as with aggregation of transthyretin in senile systemic amyloidosis.

One generic treatment currently being considered is immunological, based on antibodies that can bind a diverse collection of small amyloid oligomers (Kayed et al, 2003, Science 300:486-489); such work also demonstrates that there is a structural commonality among the oligomers of amyloid proteins, regardless of sequence. However, immunological therapies bring a high risk of potentially fatal adverse reactions due to cascade responses in the subject's own immune system, as a recent failed clinical trial has shown (Gilman et al, 2005, Neurology 64:1553-1562).

A more promising generic treatment, relevant to the present invention, utilizes the traditional approach of small molecules as modulators of disease targets, being amyloids in this case. A wide variety of compounds have shown the ability to inhibit the aggregation of amyloids in vitro, and many such compounds can inhibit the aggregation of beta-amyloid protein as well as other kinds of amyloid (see for example Klabunde et al, 2000, Nat. Struct. Biol. 7:312-321; Green et al, 2003, J. Am. Chem. Soc. 125:13404-13414; Masuda et al, 2006, Biochemistry 45:6085-6094; Ono et al, 2003, J. Neurochem 87:172-181; Tagliavini et al, 2000, J. Mol. Biol. 300: 1309-1322). Some compounds have also been shown to have beneficial in vivo effects, including reducing the size of amyloid plaques and delaying mortality in mouse models of amyloid disease (Chen et al, 2000, Nat. Med. 6:797-801; Imbimbo et al, 2007, Pharmacol. Res. 55:318-328). Of special note is resveratrol, an antioxidant component of red wine and an inhibitor of beta-amyloid aggregation at an effective concentration of 5.6 μM (Riviere et al, 2007, Bioorg. Med. Chem., 15:1160-1167). Accordingly, it is reasonable to expect that compounds which inhibit the aggregation of beta-amyloid protein in vitro may have in vitro and in vivo effects that are beneficial for the treatment of amyloid diseases, particularly with respect to Alzheimer's Disease.

All of the above listed diseases are invariably fatal using current medical practice. In none of these diseases is there any known, widely accepted therapy or treatment that can halt and/or reverse the aggregation of amyloid deposits. As such there remains an urgent need for treatments such as those provided below.

The present invention pertains to methods and compositions useful for treating amyloidosis. The methods of the invention involve administering to a subject a therapeutic compound which inhibits amyloid aggregation. "Inhibition of amyloid aggregation" is intended to encompass prevention of amyloid deposition, inhibition of further amyloid deposition in a subject with ongoing amyloidosis, and reduction of amyloid deposits in a subject with ongoing amyloidosis. Inhibition of amyloid aggregation is determined relative to an untreated subject or relative to the treated subject prior to treatment. Amyloid aggregation is inhibited by interfering with the binding of monomeric and/or oligomeric amyloid protein to other, nearby amyloid protein such that aggregation of amyloid is inhibited. This inhibition of amyloid aggregation may have effects on both chain and step polymerization mechanisms of amyloid proteins, and may affect the aggregation of both heterogeneous and homogeneous amyloid deposits. Examples of amyloid proteins include, but are by no means limited to, beta-amyloid protein, tau protein, alpha-synuclein protein, immunoglobulin light chain protein, insulin, Islet amyloid polypeptide, lysozyme, transthyretin, amyloid A, prion protein, and polyglutamate (huntingtin) protein.

As stated above, resveratrol has been shown to inhibit the aggregation of beta-amyloid protein. The compounds of the present invention were identified using structure-based drug design and virtual screening techniques as having low energy conformations that overlap geometrically and electrostatically with resveratrol and which bind to a model of amyloid aggregation as disclosed in U.S. Provisional Application Ser. No. 61/092,826. More specifically, over 700,000 known, drug-like compounds were investigated computationally for this overlap, and several thousand compounds were identified.

OBJECTS AND SUMMARY OF THE INVENTION

It is an object of the present invention to provide compounds of Formulas Ia, Ib and Ic, pharmaceutically acceptable salts, stereo-isomers, polymorphs, metabolites, pro-drugs and combinations:

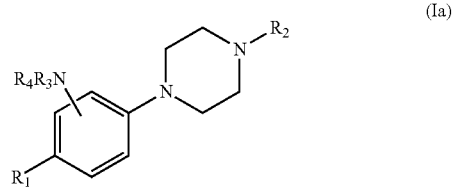

(Ia)

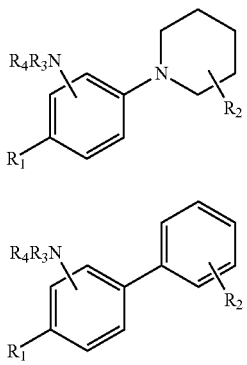

wherein R₁ is selected from the group consisting of H, nitro, carboxylic acid, alkylcarboxylic acid, acetamide connected in either direction, N-(2-ethanol)amine, N-(2-morpholmethyl)amine, amine optionally substituted with one or more alkyl groups, amide optionally substituted with one or more alkyl groups, and alkoxy; R₂ is selected from the group consisting of H, carboxylic acid, alkyl, alkanoyl, alkanesulfonyl, benzenesulfonyl, phenonyl optionally substituted with any one or more of alkoxy, halogen, or alkyl groups, benzyl optionally substituted with any one or more of alkoxy, halogen, or alkyl groups, and amide optionally substituted with any one or more of alkyl or aryl groups; R₃ is selected from the group consisting of H, alkyl, furanylalkyl, thiophenealkyl, alkanoyl, phenyl optionally substituted with any one or more halogen, alkyl, or alkoxy groups, benzyl optionally substituted with any one or more halogen, alkyl, or alkoxy groups, and phenonyl optionally substituted with any one or more halogen, alkyl, or alkoxy groups; and R₄ is selected from the group consisting of H, alkyl, or phenyl optionally substituted with any one or more halogen, alkyl, or alkoxy groups; with the following exceptions with the exceptions that compounds of Formula Ia do not include compounds wherein: i) the NR₃R₄ moiety is connected ortho to the R₁ moiety on the phenyl ring, R₁ is nitro, R₂ is phenonyl, R₄ is H, and R₃ is selected from the group consisting of H, methyl, ethyl, formyl, benzyl, furanylmethyl, tetrahydrofuranylalkyl, 2-methylpropyl, 2,2-dimethylpropyl, and 1-phenyl-propan-2-yl; ii) the NR₃R₄ moiety is connected ortho to the R₁ moiety on the phenyl ring, R₁ is selected from the group consisting of nitro, methoxy, and carboxylic acid, R₂ is selected from the group consisting of methylsulfonyl, methyl, H, and phenonyl optionally substituted with any one or more of alkoxy, halogen or alkyl, R₄ is H, and R₃ is furanylmethyl; iii) the NR₃R₄ moiety is connected ortho to the R₁ moiety on the phenyl ring, R₁ is nitro, R₂ is phenonyl optionally substituted with any one or more halogen, alkyl, or alkoxy groups, R₄ is H, and R₃ is selected from the group consisting of benzyl, 1-phenylethyl, (4-fluorophenyl)methyl, and (4-isopropylphenyl)methyl; iv) R₁ is nitro, R₂ is selected from the group consisting of (methyl)methanonyl, carboxylic acid, alkyl, H, and benzyl, R₃ is selected from the group consisting of benzyl optionally substituted with any one or more of halogen, 1-phenylethyl optionally substituted with any one or more of methoxy, alkyl and H, and R₄ is selected from the group consisting of H and alkyl; v) R₁ is selected from the group consisting of amino, H, alkyl, and methoxy; R₂ is selected from the group consisting of H, alkyl, alkylamide, (methyl)methanonyl, carboxylic acid, and alkylcarboxylic acid; R₃ is selected from the group consisting of H and alkyl; and R₄ is selected from the group consisting of H and alkyl; and yl) R₁ is acetamide, R₂ is methyl, R₃ is benzyl, and R₄ is H. These exceptions should be understood as including pharmaceutically acceptable salts, stereo-isomers, polymorphs, metabolites, pro-drugs and combinations thereof, e.g. esters.

It is another object of the present invention to provide methods useful in the treatment of amyloidosis.

It is yet another object of the present invention to provide methods for administering to a subject a therapeutic compound which inhibits amyloid aggregation.

It is another object of the present invention to provide pharmaceutical compositions for treating amyloidosis. The pharmaceutical compositions include a therapeutic compound of the invention in an amount effective to inhibit amyloid aggregation and a pharmaceutically acceptable excipient or vehicle.

The term "subject" is intended to include living organisms in which amyloidosis can occur. Examples of subjects include humans, monkeys, cows, sheep, goats, dogs, cats, mice, rats, and transgenic species thereof.

It is to be understood that the term "halogen" refers to fluorine, chlorine, bromine, or iodine. The "phenonyl" group does not refer to phenobarbital, but rather refers to a radical ketone bearing a phenyl group on the ketone opposite the radical, i.e. a phenyl ketone radical.

It is further to be understood that the notation indicated by "S/D" in small type next to a bond connected to a symbolic letter is meant to indicate the appropriate bond type, i.e. single or double, based on valence considerations for a given moiety represented by said symbolic letter. For example, an oxygen nucleus generally connects to other nuclei with single bonds; while a nitrogen nucleus might be connected via a single or a double bond, depending on whether the nitrogen also carries a hydrogen or not, respectively.

BRIEF DESCRIPTION OF DRAWINGS

FIG. 3 depicts circular dichroism scans at T=0, 24 hr, 96 hr, 120 hr, 144 hr, and 168 hr for the compound of Example 34, showing that the compound keeps amyloid from entering an aggregated structure.

FIG. 4 depicts circular dichroism scans at T=0, 24 hr, 96 hr, 120 hr, 144 hr, and 168 hr for the compound of Example 25, showing that the compound keeps amyloid from entering an aggregated structure.

FIG. 5 depicts circular dichroism scans at T=0, 24 hr, 96 hr, 120 hr, 144 hr, and 168 hr for the compound of Example 54, showing that the compound keeps amyloid from entering an aggregated structure.

FIG. 6 depicts circular dichroism scans at T=0, 24 hr, 96 hr, 120 hr, 144 hr, and 168 hr for the compound of Example 46, showing that the compound keeps amyloid from entering an aggregated structure.

DETAILED DESCRIPTION OF INVENTION

Compounds

Figure 1:
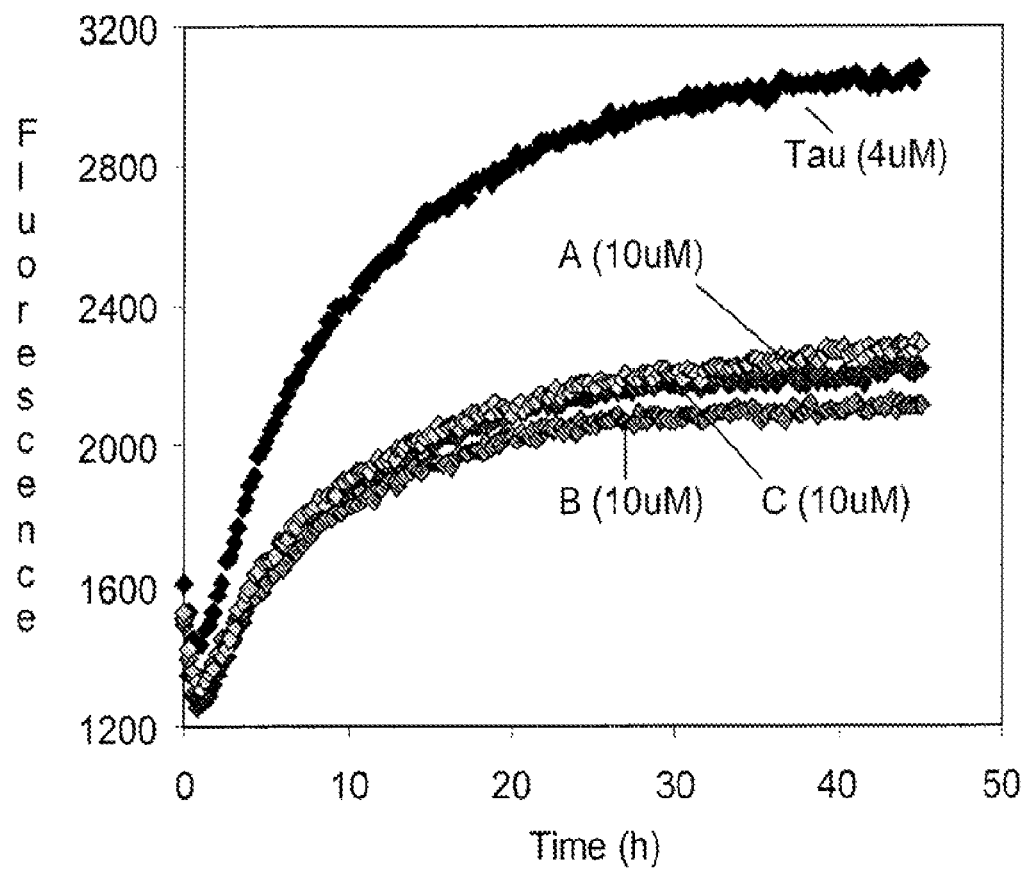
FIG. 1 is a graph over time showing the ability of several compounds of the invention (the compound of example 4 denoted as "A", the compound of example 7 denoted as "B", and the compound of example 6 denoted as "C") to inhibit the aggregation of tau protein (4 µM) at a concentration of 10 µM (control at top; lower is better).
Figure 2:
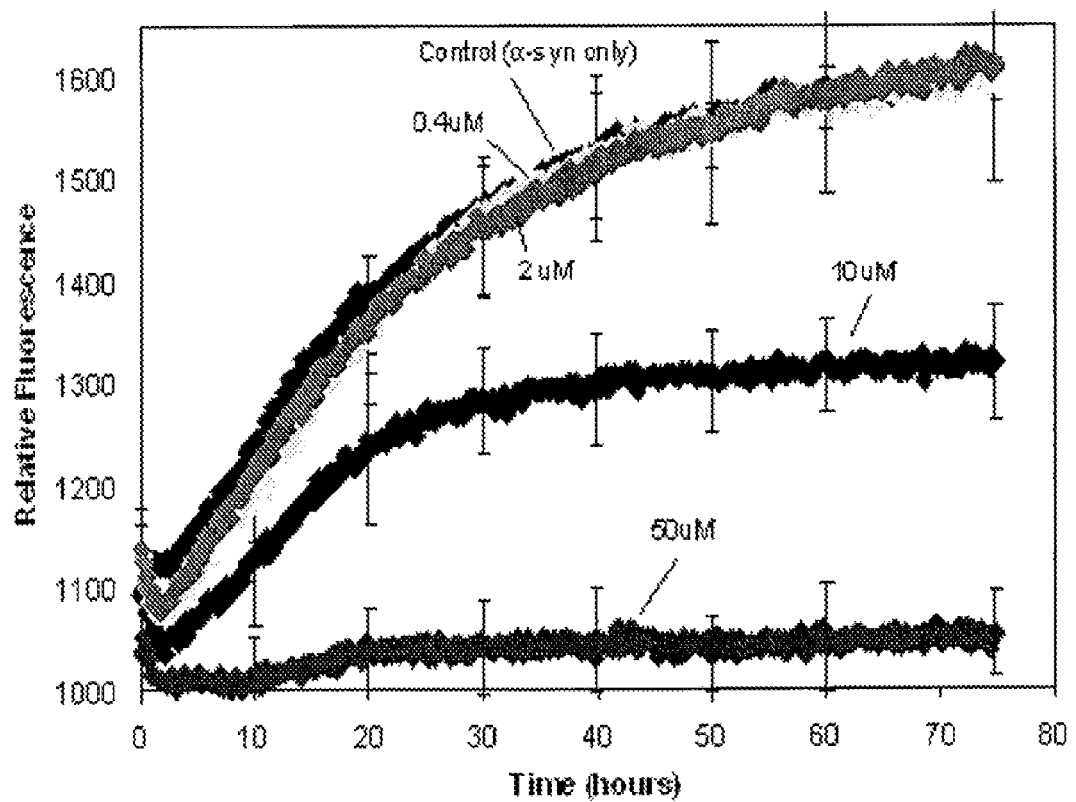
FIG. 2 is a graph over time showing the ability of the compound of example 4 to inhibit the aggregation of alpha-synuclein (6 µM) at various concentrations indicated, with 50% inhibition at 10 µM and full inhibition at 50 µM (control at top; lower is better; error bars shown).

In accordance with the above-mentioned objects, the present invention is directed to compounds of Formulas Ia, Ib, Ic, pharmaceutically acceptable salts, stereo-isomers, polymorphs, metabolites, analogues, pro-drugs and combinations thereof:

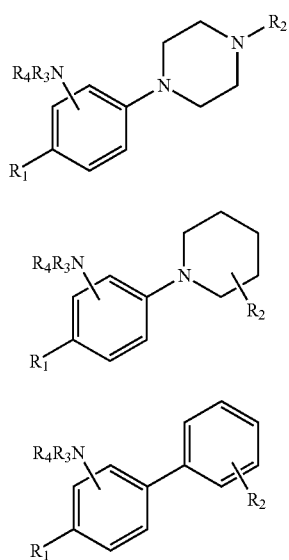

wherein $R_1$ is selected from the group consisting of H, nitro, carboxylic acid, alkylcarboxylic acid, acetamide connected in either direction, N-(2-ethanol)amine, N-(2-morpholmethyl)amine, amine optionally substituted with one or more alkyl groups, amide optionally substituted with one or more alkyl groups, and alkoxy; $R_2$ is selected from the group consisting of H, carboxylic acid, alkyl, alkanoyl, alkanesulfonyl, benzenesulfonyl, phenonyl optionally substituted with any one or more of alkoxy, halogen, or alkyl groups, benzyl optionally substituted with any one or more of alkoxy, halogen, or alkyl groups, and amide optionally substituted with any one or more of alkyl or aryl groups; $R_3$ is selected from the group consisting of H, alkyl, furanylalkyl, thiophenealkyl, alkanoyl, phenyl optionally substituted with any one or more halogen, alkyl, or alkoxy groups, benzyl optionally substituted with any one or more halogen, alkyl, or alkoxy groups, and phenonyl optionally substituted with any one or more halogen, alkyl, or alkoxy groups; and $R_4$ is selected from the group consisting of H, alkyl, or phenyl optionally substituted with any one or more halogen, alkyl, or alkoxy groups; with the exceptions that compounds of Formula Ia do not include compounds wherein: i) the $NR_3R_4$ moiety is connected ortho to the $R_1$ moiety on the phenyl ring, $R_1$ is nitro, $R_2$ is phenonyl, $R_4$ is H, and $R_3$ is selected from the group consisting of H, methyl, ethyl, formyl, benzyl, furanylmethyl, tetrahydrofuranylalkyl, 2-methylpropyl, 2,2-dimethylpropyl, and 1-phenyl-propan-2-yl; ii) the $NR_3R_4$ moiety is connected ortho to the $R_1$ moiety on the phenyl ring, $R_1$ is selected from the group consisting of nitro, methoxy, and carboxylic acid, $R_2$ is selected from the group consisting of methylsulfonyl, methyl, H, and phenonyl optionally substituted with any one or more of alkoxy, halogen or alkyl, $R_4$ is H, and $R_3$ is furanylmethyl; iii) the $NR_3R_4$ moiety is connected ortho to the $R_1$ moiety on the phenyl ring, $R_1$ is nitro, $R_2$ is phenonyl optionally substituted with any one or more halogen, alkyl, or alkoxy groups, $R_4$ is H, and $R_3$ is selected from the group consisting of benzyl, 1-phenylethyl, (4-fluorophenyl)methyl, and (4-isopropylphenyl)methyl; iv) $R_1$ is nitro, $R_2$ is selected from the group consisting of (methyl)methanonyl, carboxylic acid, alkyl, H, and benzyl, $R_3$ is selected from the group consisting of benzyl optionally substituted with any one or more of halogen, 1-phenylethyl optionally substituted with any one or more of methoxy, alkyl and H, and $R_4$ is selected from the group consisting of H and alkyl; v) $R_1$ is selected from the group consisting of amino, H, alkyl, and methoxy; $R_2$ is selected from the group consisting of H, alkyl, alkylamide, (methyl)methanonyl, carboxylic acid, and alkylcarboxylic acid; $R_3$ is selected from the group consisting of H and alkyl; and $R_4$ is selected from the group consisting of H and alkyl; and yl) $R_1$ is acetamide, $R_2$ is methyl, $R_3$ is benzyl, and $R_4$ is H. These exceptions should be understood as including pharmaceutically acceptable salts, stereo-isomers, polymorphs, metabolites, pro-drugs and combinations thereof, e.g. esters.

In certain other embodiments, $R_1$ is selected from the group consisting of nitro, acetamide connected in either direction, N-(2-ethanol)amine, amino optionally substituted with any one or more alkyl groups, and amide optionally substituted with any one or more alkyl groups; $R_2$ is selected from the group consisting of carboxylic acid, amide optionally substituted with any one or more of alkyl, and phenonyl optionally substituted with any one or more of alkoxy or alkyl; $R_3$ is selected from the group consisting of methyl, phenyl optionally substituted with any one or more halogen, alkyl, or alkoxy groups, benzyl optionally substituted with any one or more halogen, alkyl, or alkoxy groups, and phenonyl optionally substituted with any one or more halogen, alkyl, or alkoxy groups; and $R_4$ is selected from the group consisting of H, alkoxy, and alkyl; with the exceptions that compounds of Formula Ia do not include compounds wherein: i) the $NR_3R_4$ moiety is connected ortho to the $R_1$ moiety on the phenyl ring, $R_1$ is nitro, $R_2$ is phenonyl, $R_4$ is H, and $R_3$ is selected from the group consisting of methyl and benzyl; ii) the $NR_3R_4$ moiety is connected ortho to the $R_1$ moiety on the phenyl ring, $R_1$ is nitro, $R_2$ is phenonyl optionally substituted with any one or more of halogen, alkyl, or alkoxy, $R_4$ is H, and $R_3$ is selected from the group consisting of benzyl, (4-fluorophenyl)methyl, and (4-isopropylphenyl)methyl; iii) $R_1$ is nitro, $R_2$ is carboxylic acid, $R_3$ is selected from the group consisting of benzyl optionally substituted with any one or more of halogen and methyl, and $R_4$ is selected from the group consisting of H and alkyl; and iv) $R_1$ is amino, $R_2$ is selected from the group consisting of alkylamide and carboxylic acid, $R_3$ is methyl, and $R_4$ is selected from the group consisting of H and alkyl.

In another embodiments, $R_1$ is selected from the group consisting of nitro, acetamide connected in either direction, N-(2-ethanol)amine, amino optionally substituted with methyl or dimethyl, amide optionally substituted with methyl, ethyl, dimethyl, or diethyl, and methoxy; $R_2$ is selected from the group consisting of phenonyl optionally substituted with any one or more of methoxy, alkyl, or halogen, amide optionally substituted with any one or more of methyl, phenyl, benzyl, or dimethyl, and carboxylic acid; $R_3$ is selected from the group consisting of methyl, phenyl optionally substituted with any one or more of halogen, alkyl, or methoxy, benzyl optionally substituted with any one or more of halogen, alkyl, or methoxy, and phenonyl optionally substituted with any one or more of halogen, alkyl, or methoxy; and $R_4$ is selected from the group consisting of H, methyl, and phenyl optionally substituted with any one or more of halogen, alkyl, or alkoxy; with the exceptions that compounds of Formula Ia do not include compounds wherein: i) the $NR_3R_4$ moiety is connected ortho to the $R_1$ moiety on the phenyl ring, $R_1$ is nitro, $R_2$ is phenonyl, $R_4$ is H, and $R_3$ is selected from the group consisting of methyl and benzyl; ii) the $NR_3R_4$ moiety is connected ortho to the $R_1$ moiety on the phenyl ring, $R_1$ is nitro, $R_2$ is phenonyl optionally substituted with any one or more of methoxy, alkyl, or hydrogen, $R_4$ is H, and $R_3$ is selected from the group consisting of (4-fluorophenyl)methyl and (4-isopropylphenyl)methyl; iii) $R_1$ is nitro, $R_2$ is carboxylic acid, $R_3$ is selected from the group consisting of benzyl optionally substituted with any one or more of halogen and methyl, and $R_4$ is selected from the group consisting of H and methyl; and iv) $R_1$ is amino, $R_2$ is selected from the group consisting of alkylamide and carboxylic acid, $R_3$ is methyl, and $R_4$ is selected from the group consisting of H and methyl.

In certain other embodiments, the present invention is directed to the compound according to Formula Ia, pharmaceutically acceptable salts, stereo-isomers, polymorphs, metabolites, analogues, pro-drugs and combinations thereof:

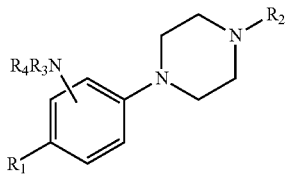

(Ia)

wherein the $NR_3R_4$ moiety is connected ortho to the $R_1$ moiety on the phenyl ring; $R_1$ is selected from the group consisting of nitro, amino optionally substituted with methyl or dimethyl, and amide optionally substituted with methyl, dimethyl, ethyl, or diethyl; $R_2$ is phenonyl optionally substituted with halogen or methoxy; $R_3$ is selected from the group consisting of phenyl optionally substituted with halogen or methoxy and benzyl optionally substituted with halogen or methoxy; and $R_4$ is selected from the group consisting of H, methyl, and phenyl; with the following exception: when $R_1$ is nitro, $R_4$ is H, and $R_3$ is benzyl optionally substituted with fluoro or isopropyl.

In certain other embodiments, the present invention is directed to the compound according to Formula Ia, pharmaceutically acceptable salts, stereo-isomers, polymorphs, metabolites, analogues, pro-drugs and combinations thereof:

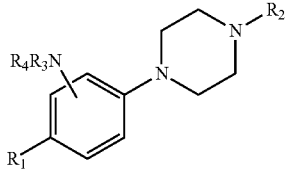

(Ia)

wherein the $NR_3R_4$ moiety is connected ortho to the $R_1$ moiety on the phenyl ring; $R_1$ is selected from the group consisting of nitro, amino optionally substituted with methyl or dimethyl, and amide optionally substituted with methyl, dimethyl, ethyl, or diethyl; $R_2$ is phenonyl optionally substituted with halogen or methoxy; $R_3$ is phenyl optionally substituted with halogen or methoxy; and $R_4$ is selected from the group consisting of H, methyl, and phenyl.

In certain other embodiments, the present invention is directed to the compound according to Formula Ia, pharmaceutically acceptable salts, stereo-isomers, polymorphs, metabolites, analogues, pro-drugs and combinations thereof:

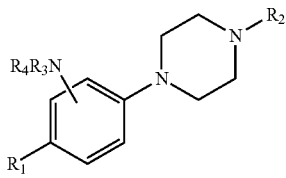

(Ia)

wherein the $NR_3R_4$ moiety is connected ortho to the $R_1$ moiety on the phenyl ring; $R_1$ is selected from the group consisting of nitro, amino optionally substituted with methyl or dimethyl, and amide optionally substituted with methyl, dimethyl, ethyl, or diethyl; $R_2$ is phenonyl optionally substituted with halogen or methoxy; $R_3$ is selected from the group consisting of phenyl optionally substituted with halogen or methoxy and benzyl optionally substituted with halogen or methoxy; and $R_4$ is selected from the group consisting of methyl and phenyl.

In certain other embodiments, the present invention is directed to the compound according to Formula Ia, pharmaceutically acceptable salts, stereo-isomers, polymorphs, metabolites, analogues, pro-drugs and combinations thereof:

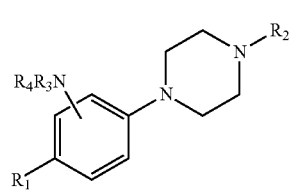

(Ia)

wherein the $NR_3R_4$ moiety is connected ortho to the $R_1$ moiety on the phenyl ring; $R_1$ is selected from the group consisting of amino optionally substituted with methyl or dimethyl, and amide optionally substituted with methyl, dimethyl, ethyl, or diethyl; $R_2$ is phenonyl optionally substituted with halogen or methoxy; $R_3$ is selected from the group consisting of phenyl optionally substituted with halogen or methoxy and benzyl optionally substituted with halogen or methoxy; and $R_4$ is selected from the group consisting of H, methyl, and phenyl.

In yet another embodiment, the present invention is directed to the compound of Formula 1c, pharmaceutically acceptable salts, stereo-isomers, polymorphs, metabolites, analogues, pro-drugs and combinations thereof:

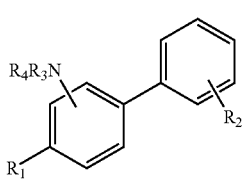

(Ic)

wherein the $NR_3R_4$ moiety is connected ortho to the $R_1$ moiety on the phenyl ring; $R_1$ is selected from the group consisting of nitro, amino optionally substituted with methyl or dimethyl, and amide optionally substituted with methyl, dimethyl, ethyl, or diethyl; the $R_2$ moiety is connected meta with respect to the phenyl ring; $R_2$ is carboxylic acid; $R_3$ is selected from the group consisting of phenyl optionally substituted by any one or more of methoxy or halogen and benzyl optionally substituted by any one or more of methoxy or halogen; and $R_4$ is selected from the group consisting of H and methyl.

In the above description, it is to be understood that "halogen" refers to fluorine, chlorine, bromine, or iodine. The compounds disclosed in Formulas Ia, Ib and Ic should be understood as also accommodating methyl, ethyl, methoxy, fluoro, or chloro groups at any position otherwise occupied by a ring hydrogen. Moreover, $R_3$ and $R_4$ may be used in combination to produce a nitro moiety on the phenyl ring, or to create ring systems such as morpholine, quinoline, or isoquinoline.

In certain preferred embodiments, the present invention is directed to the following compounds, which are encompassed by Formulas Ia, Ib, or Ic: (4-(4-nitro-3-(phenylamino)phenyl) piperazin-1-yl)(phenyl)methanone; 5-(4-dimethylcarbamylpiperazin-1-yl)-2-nitro-N-phenylbenzenamine; N-methyl-5-(4-benzoylpiperazin-1-yl)-2-nitro-N-phenylbenzenamine; (4-(3-(dimethylamino)-4-nitrophenyl)piperazin-1-yl)(phenyl)methanone; N-(2-(4-benzoylpiperazin-1-yl)-5-nitrophenyl)acetamide; 2-(benzylamino)-N,N-dimethyl-4-(4-benzoylpiperazin-1-yl)benzamide; 2-(benzylamino)-N-ethyl-4-(4-benzoylpiperazin-1-yl)benzamide; 3'-(benzylamino)-4'-nitrophenyl-3-carboxylic acid; 3'-(benzylamino)-4'-nitro-N-phenylbiphenyl-3-carboxamide; ethyl-1-(3-(benzylamino)-4-nitrophenyl)piperidine-4-carboxylate; N-(2-(4-benzoylpiperazin-1-yl)-5-nitrophenyl)benzenamine; (4-(4-amino-3-(phenylamino)phenyl)piperazin-1-yl)(phenyl)methanone; 1-(3-(benzylamino)-4-nitrophenyl)piperidine-3-carboxylic acid; 4'-nitro-3'-(phenylamino) biphenyl-3-carboxylic acid; N,N-dimethyl-2-(4-benzoylpiperazin-1-yl)-5-nitrobenzenamine; 4'-amino-3'-(phenylamino) biphenyl-3-carboxylic acid; (4-(3-(N-benzyl-N-phenylamino)-4-aminophenyl)piperazin-1-yl)(phenyl)methanone; (4-(3-(N-methyl-N-phenylamino)-4-(dimethylamino)phenyl) piperazin-1-yl)(phenyl)methanone; (4-(4-(dimethylamino)-3-(phenylamino)phenyl)piperazin-1-yl)(phenyl)methanone; (4-(3-(N-methyl-N-phenylamino)-4-aminophenyl)piperazin-1-yl)(phenyl)methanone; (4-(3-(N-methyl-N-phenylamino)-4-(methylamino)phenyl)piperazin-1-yl)(phenyl)methanone; (4-(4-(methylamino)-3-(phenylamino)phenyl) piperazin-1-yl)(phenyl)methanone; 2-(4-(4-benzoylpiperazin-1-yl)-2-(phenylamino)phenylamino) ethanol; N-benzyl-2-(4-benzoylpiperazin-1-yl)-5-nitrobenzenamine; N-(4-(4-benzoylpiperazin-1-yl)-2-(phenylamino)phenyl)acetamide; and 4-(4-benzoylpiperazin-1-yl)-N-1-(2-morpholinoethyl)-N2-phenylbenzene-1,2-diamine. In certain embodiments, these compounds may be incorporated into a pharmaceutically acceptable dosage form.

In certain other embodiments, the present invention is directed to the following compounds, pharmaceutically acceptable salt, stereo-isomer, polymorph, metabolite, analogue, pro-drug and combinations thereof, selected from the group consisting of (4-(4-nitro-3-(phenylamino)phenyl)piperazin-1-yl)(phenyl)methanone, (4-(3-(methyl(phenyl)amino)-4-nitrophenyl)piperazin-1-yl)(phenyl)methanone, (4-(3-(diphenylamino)-4-nitrophenyl)piperazin-1-yl)(phenyl)methanone, (4-(3-(benzyl(methyl)amino)-4-nitrophenyl)piperazin-1-yl)(phenyl)methanone, (4-(3-(benzyl(phenyl)amino)-4-nitrophenyl)piperazin-1-yl)(phenyl) methanone, (4-(4-amino-3-(phenylamino)phenyl)piperazin-1-yl)(phenyl)methanone, (4-(4-amino-3-(methyl(phenyl) amino)phenyl)piperazin-1-yl)(phenyl)methanone, (4-(4-amino-3-(diphenylamino)phenyl)piperazin-1-yl)(phenyl)methanone, (4-(4-amino-3-(benzyl(phenyl)amino)phenyl) piperazin-1-yl)(phenyl)methanone, (4-(4-amino-3-(benzyl (methyl)amino)phenyl)piperazin-1-yl)(phenyl)methanone, (4-(4-amino-3-(benzylamino)phenyl)piperazin-1-yl)(phenyl)methanone, (4-(3-(benzylamino)-4-(methylamino)phenyl)piperazin-1-yl)(phenyl)methanone, (4-(3-(benzyl(methyl)amino)-4-(methylamino)phenyl)piperazin-1-yl) (phenyl)methanone, (4-(3-(benzyl(phenyl)amino)-4-(methylamino)phenyl)piperazin-1-yl)(phenyl)methanone, (4-(3-(diphenylamino)-4-(methylamino)phenyl)piperazin-1-yl)(phenyl)methanone, (4-(3-(methyl(phenyl)amino)-4-(methylamino)phenyl)piperazin-1-yl)(phenyl)methanone, (4-(4-(methylamino)-3-(phenylamino)phenyl)piperazin-1-yl)(phenyl)methanone, (4-(4-(dimethylamino)-3-(phenylamino)phenyl)piperazin-1-yl)(phenyl)methanone, (4-(4-(dimethylamino)-3-(methyl(phenyl)amino)phenyl) piperazin-1-yl)(phenyl)methanone, (4-(4-(dimethylamino)-3-(diphenylamino)phenyl)piperazin-1-yl)(phenyl) methanone, (4-(3-(benzyl(phenyl)amino)-4-(dimethylamino)phenyl)piperazin-1-yl)(phenyl)methanone, (4-(3-(benzyl(methyl)amino)-4-(dimethylamino)phenyl) piperazin-1-yl)(phenyl)methanone, (4-(3-(benzylamino)-4-(dimethylamino)phenyl)piperazin-1-yl)(phenyl)methanone, 4-(4-benzoylpiperazin-1-yl)-2-(benzylamino)benzamide, 4-(4-benzoylpiperazin-1-yl)-2-(benzyl(methyl)amino)benzamide, 4-(4-benzoylpiperazin-1-yl)-2-(benzyl(phenyl) amino)benzamide, 4-(4-benzoylpiperazin-1-yl)-2-(diphenylamino)benzamide, 4-(4-benzoylpiperazin-1-yl)-2-(methyl (phenyl)amino)benzamide, 4-(4-benzoylpiperazin-1-yl)-2-(phenylamino)benzamide, 4-(4-benzoylpiperazin-1-yl)-N-methyl-2-(phenylamino)benzamide, 4-(4-benzoylpiperazin-1-yl)-N-methyl-2-(methyl(phenyl)amino)benzamide, 4-(4-benzoylpiperazin-1-yl)-2-(diphenylamino)-N-methylbenzamide, 4-(4-benzoylpiperazin-1-yl)-2-(benzyl (phenyl)amino)-N-methylbenzamide, 4-(4-benzoylpiperazin-1-yl)-2-(benzyl(methyl)amino)-N-methylbenzamide, and 4-(4-benzoylpiperazin-1-yl)-2-(benzylamino)-N-methylbenzamide, 4-(4-benzoylpiperazin-1-yl)-N-ethyl-2-(phenylamino)benzamide, 4-(4-benzoylpiperazin-1-yl)-N-ethyl-2-(methyl(phenyl)amino) benzamide, 4-(4-benzoylpiperazin-1-yl)-2-(diphenylamino)-N-ethylbenzamide, 4-(4-benzoylpiperazin-1-yl)-2-(benzyl(phenyl)amino)-N-ethylbenzamide, 4-(4-benzoylpiperazin-1-yl)-2-(benzyl(methyl)amino)-N-ethylbenzamide, 4-(4-benzoylpiperazin-1-yl)-2-(benzylamino)-N-thylbenzamide, 4-(4-benzoylpiperazin-1-yl)-2-(benzylamino)-N,N-dimethylbenzamide, 4-(4-benzoylpiperazin-1-yl)-2-(benzyl(methyl)amino)-N,N-dimethylbenzamide, 4-(4-benzoylpiperazin-1-yl)-2-(benzyl (phenyl)amino)-N,N-dimethylbenzamide, 4-(4-benzoylpiperazin-1-yl)-2-(diphenylamino)-N,N-dimethylbenzamide, 4-(4-benzoylpiperazin-1-yl)-N,N-dimethyl-2-(methyl(phenyl)amino)benzamide, 4-(4-benzoylpiperazin-1-yl)-N,N-dimethyl-2-(phenylamino) benzamide, 4-(4-benzoylpiperazin-1-yl)-2-(benzylamino)-N,N-diethylbenzamide, 4-(4-benzoylpiperazin-1-yl)-2-(benzyl(methyl)amino)-N,N-diethylbenzamide, 4-(4-benzoylpiperazin-1-yl)-2-(benzyl(phenyl)amino)-N,N-diethylbenzamide, 4-(4-benzoylpiperazin-1-yl)-2-(diphenylamino)-N,N-diethylbenzamide, 4-(4-benzoylpiperazin-1-yl)-N,N-diethyl-2-(methyl(phenyl) amino)benzamide, and 4-(4-benzoylpiperazin-1-yl)-N,N-diethyl-2-(phenylamino)benzamide.

The compounds of the present invention may be incorporated into various pharmaceutically acceptable dosage forms, including but not limited to oral and parenteral dosage forms. Oral dosage forms may include tablets, capsules, liquids, and the like. Parenteral dosage forms may include, but are not limited to dosage forms for intravenous, subcutaneous, intramuscular, intraperitoneal, intrarterial, and intradermal administration. The dosage forms of the present invention will contain a therapeutically effective amount of a compound(s) described herein such that the therapeutically effective dose is sufficient to inhibit amyloid aggregation in a subject.

In addition to containing a therapeutically effective amount of a compound(s) described herein, the dosage formulations may also contain pharmaceutically acceptable excipients. For example, the compositions of the present invention may contain a pharmaceutically acceptable diluent, including but not limited to monosaccharides, disaccharides, polyhydric alcohols and mixtures of two or more thereof. Preferred pharmaceutical diluents include, for example, starch, lactose, dextrose, mannitol, sucrose, microcrystalline cellulose, sorbitol, xylitol, fructose, and mixtures of two or more thereof.

In other embodiments, the pharmaceutical diluent is water-soluble, such as lactose, dextrose, mannitol, sucrose, or mixtures of two or more thereof.

Other suitable excipients for use in the compositions of the present invention include, but are not limited to, for example, poly(ethylene-vinyl acetate), copolymers of lactic acid and glycolic acid, poly(lactic acid), gelatin, collagen matrices, polysaccharides, poly(D,L lactide), poly(malic acid), poly (caprolactone), celluloses, albumin, starch, casein, dextran, polyesters, ethanol, mathacrylate, polyurethane, polyethylene, vinyl polymers, glycols, mixtures thereof and the like.

Other excipients may include, but are not limited to, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars and starches. See, for example, Remington: The Science and Practice of Pharmacy, 1995, Gennaro ed.

As will be apparent to one knowledgeable in the art, specific excipients known in the art may be selected based on their properties and release characteristics in view of the intended use. Specifically, the carrier may be pH-sensitive, thermo-sensitive, thermo-gelling, arranged for sustained release or a quick burst. In some embodiments, carriers of different classes may be used in combination for multiple effects, for example, a quick burst followed by sustained release.

In other embodiments, one or more of the compounds in the invention may be encapsulated for delivery. Specifically, the compounds may be encapsulated in biodegradable microspheres, microcapsules, microparticles, or nanospheres. The delivery vehicles may be composed of, for example, hyaluronic acid, polyethylene glycol, poly(lactic acid), gelatin, poly(E-caprolactone), or a poly(lactic-glycolic) acid polymer. Combinations may also be used, as, for example, gelatin nanospheres may be coated with a polymer of poly(lactic-glycolic) acid. As will be apparent to one knowledgeable in the art, these and other suitable delivery vehicles may be prepared according to protocols known in the art and utilized for delivery of the compounds.

It is of note that the compounds of the invention may be combined with permeation enhancers known in the art for improving delivery. Examples of permeation enhancers include, but are by no means limited to those compounds described in U.S. Pat. Nos. 3,472,931; 3,527,864; 3,896,238; 3,903,256; 3,952,099; 4,046,886; 4,130,643; 4,130,667; 4,299,826; 4,335,115; 4,343,798; 4,379,454; 4,405,616; 4,746,515; 4,788,062; 4,820,720; 4,863,738; 4,863,970; and 5,378,730; British Pat. No. 1,011,949; and Idson, 1975, J. Pharm. Sci. 64:901-924.

Methods of Treating Amyloid Diseases

The present invention is also directed to methods of treating amyloid diseases, such as but not limited to Alzheimer's disease, Parkinson's disease, Huntington's disease, and prion diseases (e.g., Creutzfeldt-Jakob disease, variant Creutzfeldt-Jakob disease, Gertsmann-Straussler-Scheineker Syndrome, Fatal Familial Insomnia, and Kuru). The methods include administration of a compound that inhibits the aggregation of an amyloidogenic protein.

In certain embodiments, the methods of the present invention include administration of a therapeutically effective dose of a compound(s) described in Examples Ia, Ib and Ic above for inhibiting amyloid aggregation in a subject.

For example, amyloid diseases may be treated by administering a therapeutically effective dose of a compound including, but not limited to: (4-(4-nitro-3-(phenylamino) phenyl)piperazin-1-yl)(phenyl)methanone; 5-(4-dimethyl-carbamylpiperazin-1-yl)-2-nitro-N-phenylbenzenamine; N-methyl-5-(4-benzoylpiperazin-1-yl)-2-nitro-N-phenyl-benzenamine; (4-(3-(dimethylamino)-4-nitrophenyl)piperazin-1-yl)(phenyl)methanone; N-(2-(4-benzoylpiperazin-1-yl)-5-nitrophenyl)acetamide; 2-(benzylamino)-N,N-dimethyl-4-(4-benzoylpiperazin-1-yl)benzamide; 2-(benzylamino)-N-ethyl-4-(4-benzoylpiperazin-1-yl)benzamide; 3'-(benzylamino)-4'-nitrophenyl-3-carboxylic acid; 3'-(benzylamino)-4'-nitro-N-phenylbiphenyl-3-carboxamide; ethyl-1-(3-(benzylamino)-4-nitrophenyl)piperidine-4-carboxylate; N-(2-(4-benzoylpiperazin-1-yl)-5-nitrophenyl) benzenamine; (4-(4-amino-3-(phenylamino)phenyl) piperazin-1-yl)(phenyl)methanone; 1-(3-(benzylamino)-4-nitrophenyl)piperidine-3-carboxylic acid; 4'-nitro-3'-(phenylamino) biphenyl-3-carboxylic acid; N,N-dimethyl-2-(4-benzoylpiperazin-1-yl)-5-nitrobenzenamine; 4'-amino-3'-(phenylamino) biphenyl-3-carboxylic acid; (4-(3-(N-benzyl-N-phenylamino)-4-aminophenyl)piperazin-1-yl)(phenyl) methanone; (4-(3-(N-methyl-N-phenylamino)-4-(dimethylamino)phenyl)piperazin-1-yl)(phenyl)methanone; (4-(4-(dimethylamino)-3-(phenylamino)phenyl)piperazin-1-yl)(phenyl)methanone; (4-(3-(N-methyl-N-phenylamino)-4-aminophenyl)piperazin-1-yl)(phenyl)methanone; (4-(3-(N-methyl-N-phenylamino)-4-(methylamino)phenyl) piperazin-1-yl)(phenyl)methanone; (4-(4-(methylamino)-3-(phenylamino)phenyl)piperazin-1-yl)(phenyl)methanone; 2-(4-(4-benzoylpiperazin-1-yl)-2-(phenylamino)phenylamino)ethanol; N-benzyl-2-(4-benzoylpiperazin-1-yl)-5-nitrobenzenamine; N-(4-(4-benzoylpiperazin-1-yl)-2-(phenylamino)phenyl)acetamide; and 4-(4-benzoylpiperazin-1-yl)-N1-(2-morpholinoethyl)-N2-phenylbenzene-1,2-diamine.

In certain other embodiments, the methods of the present invention include administration of a therapeutically effective dose of a compound of Formula II, pharmaceutically acceptable salts, stereo-isomers, polymorphs, metabolites, analogues, pro-drugs and combinations thereof:

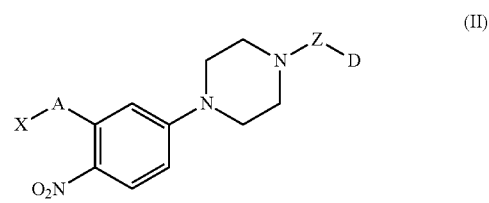

(II)

wherein X is selected from the group consisting of hydrogen, methyl, amine, methoxy, phenyl optionally substituted with up to a total of three methyl and/or methoxy and/or halogen groups, cyclopentane, morpholine, piperidine, N-methylpiperidine, N-ethylpiperidine, (N,N-diethyl)formamide, pyridine, pyrazine, pyrrole, pyrrolidine, furan, thiophene, tetrahydrofuran, pyran, tetrahydroisoquinoline, isoquinoline, quinoline, N-phenylpiperazine optionally substituted with up to a total of three methoxy and/or halogen groups, or N-benzylpiperazine;

A is an optional spacer group, attachable in either direction, selected from the group consisting of —NH—, —NHCH$_2$—, —NHCH$_2$CH$_2$—, —NHCH$_2$CH$_2$O—, and —NHCH$_2$(CH$_3$);

D is selected from the group consisting of methyl, isopropyl, tert-butyl, dimethylamine, morpholine, alcohol, phenyl optionally substituted with up to a total of three methyl and/or ethyl and/or methoxy and/or halogen and/or acetamide and/or ethoxy and/or cyano groups, pyridine, pyrazine, pyrrole, pyrrolidine, furan, thiophene, tetrahydrofuran, and pyran; and Z is an optional spacer group, selected from the group consisting of —CH$_2$—, —SO$_2$—, —SO$_2$CH$_2$—, —CH$_2$C(=O)—, —CH$_2$CH$_2$—, —C(=O)—, and —C(=S)NHC(=O)—.

In a preferred embodiment of the invention, A is absent (thus X is directly connected to the phenyl ring at the position held by A); X is tetrahydroisoquinoline, attached to the phenyl ring by its lone nitrogen; Z is —C(=O)—; and D is methyl. In another preferred embodiment of the invention, A is absent; X is morpholine, attached to the phenyl ring by its lone nitrogen; Z is —CH—; and D is methyl.

In certain other embodiments, the methods of the present invention include administration of a compound of Formula III, pharmaceutically acceptable salts, stereo-isomers, polymorphs, metabolites, analogues, pro-drugs and combinations thereof:

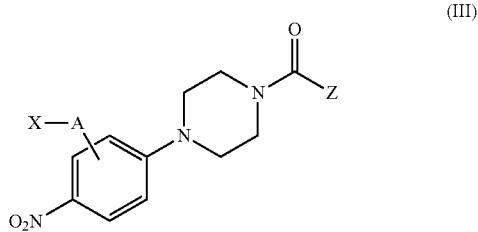

(III)

wherein X is selected from the group consisting of methyl, methylamine, halogen, and phenyl optionally substituted with up to a total of three methyl and/or methoxy and/or halogen groups;

A is an optional spacer group, attachable in either direction, selected from the group consisting of —NH—, —N(CH$_3$)H—, —O—, —OCH$_3$—, —C(=O)NH—, and —NHCH$_2$—; and Z is selected from the group consisting of phenyl optionally substituted with up to a total of three methyl and/or ethyl and/or methoxy and/or halogen and/or acetamide and/or ethoxy and/or cyano groups; excepting those compounds that include X as phenyl and A as —NHCH$_2$—, the nitrogen in said A being connected to the nitro-containing phenyl ring in said formula and the carbon in said A being connected to said X in said formula.

Amyloid diseases may be treated, for example, by administering a therapeutically effective dose of a compound including, but not limited to: [4-[4-nitro-3-(tricyclo[3.3.1.1 3,7]dec-2-ylamino)phenyl]-1-piperazinyl]phenylmethanone, 2-(4-benzoyl-1-piperazinyl)-5-nitrobenzonitrile, [4-[3-[(4-methyl-4H-1,2,4-triazol-3-yl)thio]-4-nitrophenyl]-1-piperazinyl]phenylmethanone, [4-[4-nitro-3-(2-propen-1-ylamino)phenyl]-1-piperazinyl]phenylmethanone, [4-[3-[(2-methylpropyl)amino]-4-nitrophenyl]-1-piperazinyl] phenylmethanone, [4-[4-nitro-3-[[(tetrahydro-2-furanyl)methyl]amino]phenyl]-1-piperazinyl]phenylmethanone, [4-[3-[(2,2-dimethylpropyl)amino]-4-nitrophenyl]-1-piperazinyl]phenylmethanone, [4-[3-(ethylamino)-4-nitrophenyl]-1-piperazinyl]phenylmethanone, [4-(2-methyl-4-nitrophenyl)-1-piperazinyl]phenylmethanone, 5-[[2-(4-benzoyl-1-piperazinyl)-5-nitrophenyl]methylene]-2,4,6(1H,3H,5H)-pyrimidinetrione, [4-[2-(2,5-dimethyl-1H-pyrrol-1-yl)-4-nitrophenyl]-1-piperazinyl]phenylmethanone, [4-[4-nitro-2-(1H-pyrrol-1-yl)phenyl]-1-piperazinyl]phenylmethanone, 2-[5-(4-benzoyl-1-piperazinyl)-2-nitrophenyl]-4-methyl-1(2H)phthalazinone, [4-[3-(methylamino)-4-nitrophenyl]-1-piperazinyl]phenylmethanone, [4-[4-nitro-3-[(3-pyridinylmethyl)amino]phenyl]-1-piperazinyl]phenylmethanone, [4-[3-(3,4-dihydro-2(1H)-isoquinolinyl)-4-nitrophenyl]-1-piperazinyl]phenylmethanone, [4-[4-nitro-3-(1-piperidinyl)phenyl]-1-piperazinyl]phenylmethanone, [4-[4-nitro-2-(trifluoromethyl)phenyl]-1-piperazinyl]phenylmethanone, [4-[4-nitro-3-[(1-phenylethyl)amino]phenyl]-1-piperazinyl]phenylmethanone, [4-[3-(4-morpholinyl)-4-nitrophenyl]-1-piperazinyl]phenylmethanone, [4-[4-nitro-3-[(1-tricyclo[3.3.1.13,7]dec-1-ylethyl)amino]phenyl]-1-piperazinyl]phenylmethanone, [4-[4-nitro-3-[(phenylmethyl)amino]phenyl]-1-piperazinyl]phenylmethanone, [4-[4-nitro-3-[(2-phenylethyl)amino]phenyl]-1-piperazinyl]phenylmethanone, [4-[3-[(2-furanylmethyl)amino]-4-nitrophenyl]-1-piperazinyl]phenylmethanone, [4-[3-(3,5-dimethyl-1H-pyrazol-1-yl)-4-nitrophenyl]-1-piperazinyl]phenylmethanone, [4-[3-(cyclopropylamino)-4-nitrophenyl]-1-piperazinyl]phenylmethanone, [4-(2-chloro-4-nitrophenyl)-1-piperazinyl]phenylmethanone, [4-(2-fluoro-4-nitrophenyl)-1-piperazinyl]phenylmethanone, 1-benzoyl-4-(3-formyl-4-nitrophenyl)piperazine, 1-benzoyl-4-[3-[(2,5-dioxo-4-imidazolidinylidene)methyl]-4-nitrophenyl]piperazine, 1-(3-amino-4-nitrophenyl)-4-benzoylpiperazine, 1-benzoyl-4-(4-nitrophenyl)piperazine, (2,4-dichlorophenyl)[4-[4-nitro-3-[(phenylmethyl)amino]phenyl]-1-piperazinyl]methanone, (5-chloro-2-methoxyphenyl)[4-[4-nitro-3-[(phenylmethyl)amino]phenyl]-1-piperazinyl]methanone, [4-[4-nitro-3-[(phenylmethyl)amino]phenyl]-1-piperazinyl](4-propoxyphenyl)methanone, (3,4-dimethoxyphenyl)[4-[4-nitro-3-[(1-phenylethyl)amino]phenyl]-1-piperazinyl]methanone, (3,4-dimethoxyphenyl)[4-[4-nitro-3-[(phenylmethyl)amino]phenyl]-1-piperazinyl]methanone, (3-chloro-4-methylphenyl) [4-[4-nitro-3-[(phenylmethyl)amino]phenyl]-1-piperazinyl]methanone, (2-methoxy-3-methylphenyl) [4-[4-nitro-3-[(phenylmethyl)amino]phenyl]-1-piperazinyl]methanone, (2-methoxy-3-methylphenyl) [4-[4-nitro-3-[(1-phenylethyl)amino]phenyl]-1-piperazinyl]methanone, [4-(1-methylethoxy)phenyl] [4-[4-nitro-3-[(1-phenylethyl)amino]phenyl]-1-piperazinyl]methanone, [4-(1-methylethoxy)phenyl][4-[4-nitro-3-[(phenylmethyl)amino]phenyl]-1-piperazinyl]methanone, [3-(1-methylethoxy)phenyl][4-[4-nitro-3-[(1-phenylethyl)amino]phenyl]-1-piperazinyl]methanone, [3-(1-methylethoxy)phenyl][4-[4-nitro-3-[(phenylmethyl)amino]phenyl]-1-piperazinyl]methanone, (4-ethylphenyl) [4-[4-nitro-3-[(1-phenylethyl)amino]phenyl]-1-piperazinyl]methanone, (4-ethylphenyl) [4-[4-nitro-3-[(phenylmethyl)amino]phenyl]-1-piperazinyl]methanone, (3-ethoxyphenyl) [4-[4-nitro-3-[(1-phenylethyl)amino]phenyl]-1-piperazinyl]methanone, (3-ethoxyphenyl)[4-[4-nitro-3-[(phenylmethyl)amino]phenyl]-1-piperazinyl]methanone, (3,4-dichlorophenyl) [4-[4-nitro-3-[(1-phenylethyl)amino]phenyl]-1-piperazinyl]methanone, (3,4-dichlorophenyl)[4-[4-nitro-3-[(phenylmethyl)amino]phenyl]-1-piperazinyl]methanone,

[4-(1-methylethyl)phenyl][4-[4-nitro-3-[(1-phenylethyl) amino]phenyl]-1-piperazinyl]methanone, (2-iodophenyl)[4-[4-nitro-3-[(phenylmethyl)amino]phenyl]-1-piperazinyl]methanone, [4-(1,1-dimethylethyl)phenyl][4-[4-nitro-3-[(phenylmethyl)amino]phenyl]-1-piperazinyl]methanone, (3-bromophenyl)[4-[4-nitro-3-[(1-phenylethyl)amino]phenyl]-1-piperazinyl]methanone, [4-[4-nitro-3-[(1-phenylethyl)amino]phenyl]-1-piperazinyl]phenylmethanone, (2-bromophenyl)[4-[4-nitro-3-[(1-phenylethyl)amino]phenyl]-1-piperazinyl]methanone, (4-butoxyphenyl)[4-[4-nitro-3-[(phenylmethyl)amino]phenyl]-1-piperazinyl]methanone, [4-(1-methylethyl)phenyl][4-[4-nitro-3-[(phenylmethyl)amino]phenyl]-1-piperazinyl]methanone, (4-ethoxyphenyl)[4-[4-nitro-3-[(1-phenylethyl)amino]phenyl]-1-piperazinyl]methanone, (2-methylphenyl)[4-[4-nitro-3-[(phenylmethyl)amino]phenyl]-1-piperazinyl]methanone, (2-methylphenyl)[4-[4-nitro-3-[(1-phenylethyl)amino]phenyl]-1-piperazinyl]methanone, (3-fluorophenyl)[4-[4-nitro-3-[(1-phenylethyl)amino]phenyl]-1-piperazinyl]methanone, (3-fluorophenyl)[4-[4-nitro-3-[(phenylmethyl)amino]phenyl]-1-piperazinyl]methanone, (3-methoxyphenyl)[4-[4-nitro-3-[(phenylmethyl)amino]phenyl]-1-piperazinyl]methanone, (3-bromophenyl)[4-[4-nitro-3-[(phenylmethyl)amino]phenyl]-1-piperazinyl]methanone, [4-(1,1-dimethylethyl)phenyl][4-[4-nitro-3-[(1-phenylethyl)amino]phenyl]-1-piperazinyl]methanone, (4-ethoxyphenyl)[4-[4-nitro-3-[(phenylmethyl)amino]phenyl]-1-piperazinyl]methanone, [4-[4-nitro-3-[(phenylmethyl)amino]phenyl]-1-piperazinyl]phenylmethanone, (4-fluorophenyl)[4-[4-nitro-3-[(1-phenylethyl)amino]phenyl]-1-piperazinyl]methanone, (4-chlorophenyl)[4-[4-nitro-3-[(1-phenylethyl)amino]phenyl]-1-piperazinyl]methanone, (4-fluorophenyl)[4-[4-nitro-3-[(phenylmethyl)amino]phenyl]-1-piperazinyl]methanone, (2-chlorophenyl)[4-[4-nitro-3-[(1-phenylethyl)amino]phenyl]-1-piperazinyl]methanone, (4-methylphenyl)[4-[4-nitro-3-[(1-phenylethyl)amino]phenyl]-1-piperazinyl]methanone, [4-[3-[[(4-chlorophenyl)methyl]amino]-4-nitrophenyl]-1-piperazinyl](2-fluorophenyl)methanone, (2-chlorophenyl)[4-[3-[[(4-chlorophenyl)methyl]amino]-4-nitrophenyl]-1-piperazinyl]methanone, (4-bromophenyl)[4-[3-[[(4-chlorophenyl)methyl]amino]-4-nitrophenyl]-1-piperazinyl]methanone, (2-chloro-4,5-difluorophenyl)[4-[4-nitro-3-[(phenylmethyl)amino]phenyl]-1-piperazinyl]methanone, (2-chlorophenyl)[4-[4-nitro-3-[(phenylmethyl)amino]phenyl]-1-piperazinyl]methanone, (4-methylphenyl)[4-[4-nitro-3-[(phenylmethyl)amino]phenyl]-1-piperazinyl]methanone, (2-bromophenyl)[4-[4-nitro-3-[(phenylmethyl)amino]phenyl]-1-piperazinyl]methanone, [4-[3-[[(4-chlorophenyl)methyl]amino]-4-nitrophenyl]-1-piperazinyl](4-methylphenyl)methanone, [4-[3-[[[4-(1-methylethyl)phenyl]methyl]amino]-4-nitrophenyl]-1-piperazinyl](4-methylphenyl)methanone, (3,5-dichloro-4-methoxyphenyl)[4-[3-[[[4-(1-methylethyl)phenyl]methyl]amino]-4-nitrophenyl]-1-piperazinyl]methanone, (2-fluorophenyl)[4-[4-nitro-3-[(phenylmethyl)amino]phenyl]-1-piperazinyl]methanone, (2-fluorophenyl)[4-[3-[[[4-(1-methylethyl)phenyl]methyl]amino]-4-nitrophenyl]-1-piperazinyl]methanone, (4-chlorophenyl)[4-[3-[[[4-(1-methylethyl)phenyl]methyl]amino]-4-nitrophenyl]-1-piperazinyl]methanone, [4-[3-[[(4-chlorophenyl)methyl]amino]-4-nitrophenyl]-1-piperazinyl](3-methylphenyl)methanone, (3-methylphenyl)[4-[4-nitro-3-[(phenylmethyl)amino]phenyl]-1-piperazinyl]methanone, (3-chlorophenyl)[4-[4-nitro-3-[(1-phenylethyl)amino]phenyl]-1-piperazinyl]methanone, (3-chlorophenyl)[4-[3-[[(4-chlorophenyl)methyl]amino]-4-nitrophenyl]-1-piperazinyl]methanone, (2-chloro-4,5-difluorophenyl)[4-[4-nitro-3-[(1-phenylethyl)amino]phenyl]-1-piperazinyl]methanone, (2-chloro-4,5-difluorophenyl)[4-[3-[[(4-chlorophenyl)methyl]amino]-4-nitrophenyl]-1-piperazinyl]methanone, (4-bromophenyl)[4-[4-nitro-3-[(1-phenylethyl)amino]phenyl]-1-piperazinyl]methanone, (3-chlorophenyl)[4-[4-nitro-3-[(phenylmethyl)amino]phenyl]-1-piperazinyl]methanone, (4-methoxyphenyl)[4-[4-nitro-3-[(1-phenylethyl)amino]phenyl]-1-piperazinyl]methanone, [4-[3-[[(4-chlorophenyl)methyl]amino]-4-nitrophenyl]-1-piperazinyl](4-methoxyphenyl)methanone, (4-methoxyphenyl)[4-[4-nitro-3-[(phenylmethyl)amino]phenyl]-1-piperazinyl]methanone, [4-[3-[[(4-chlorophenyl)methyl]amino]-4-nitrophenyl]-1-piperazinyl](2-methoxyphenyl)methanone, (2-methoxyphenyl)[4-[4-nitro-3-[(phenylmethyl)amino]phenyl]-1-piperazinyl]methanone, (4-bromophenyl)[4-[4-nitro-3-[(phenylmethyl)amino]phenyl]-1-piperazinyl]methanone, and (2-bromophenyl)[4-[3-[[(4-chlorophenyl)methyl]amino]-4-nitrophenyl]-1-piperazinyl]methanone, pharmaceutically acceptable salts, stereo-isomers, polymorphs, metabolites, analogues, pro-drugs and combinations thereof. Such compounds are known and have features akin to Formula II.

In certain other embodiments, the methods of the present invention include administration of a therapeutically effective dose of a compound of Formula IV, pharmaceutically acceptable salts, stereo-isomers, polymorphs, metabolites, analogues, pro-drugs and combinations thereof:

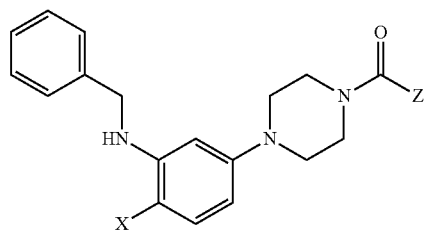

(IV)

wherein X is selected from the group consisting of hydrogen, carboxyl, methyl, cyano, amide, (N,N-dimethyl)amide, halogen, formamide, and methylformamide; and Z is phenyl optionally substituted with up to a total of three methyl and/or ethyl and/or methoxy and/or halogen and/or acetamide and/or ethoxy and/or cyano groups.

In certain other embodiments, amyloid diseases may be treated, for example, by administering a therapeutically effective dose of a compound including, but not limited to: (4-(3-(benzylamino)-2-nitrophenyl)piperazin-1-yl)(phenyl)methanone, (4-(3-(benzylamino)-5 nitrophenyl)piperazin-1-yl)(phenyl)methanone, (4-(5-(benzylamino)-2-nitrophenyl)piperazin-1-yl)(phenyl)methanone, and (4-(7-(benzylamino)benzo[c][1,2,5]oxadiazol-5-yl)piperazin-1-yl)(phenyl)methanone, pharmaceutically acceptable salts, stereo-isomers, polymorphs, metabolites, analogues, pro-drugs and combinations thereof. Such compounds vary from Formula IV by slightly altering the position of the nitro group or by incorporating a bioisosteric equivalent of nitro into a ring system, and as such are in the scope of the methods of the present invention.

In certain other embodiments, the methods of the present invention include administration of a therapeutically effective dose of a compound of Formula V, pharmaceutically acceptable salts, stereo-isomers, polymorphs, metabolites, analogues, pro-drugs and combinations thereof:

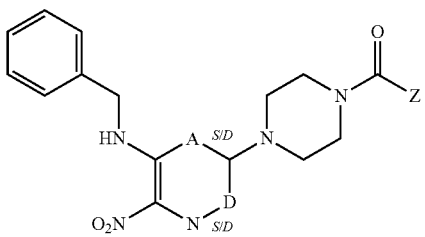

(V)

wherein A and D are each independently carbon, nitrogen, NH, oxygen, or sulfur; and Z is phenyl optionally substituted with up to a total of three methyl and/or ethyl and/or methoxy and/or halogen and/or acetamide and/or ethoxy and/or cyano groups.

In certain other embodiments, the methods of the present invention include administration of a therapeutically effective dose of a compound of Formula VI, pharmaceutically acceptable salts, stereo-isomers, polymorphs, metabolites, analogues, pro-drugs and combinations thereof:

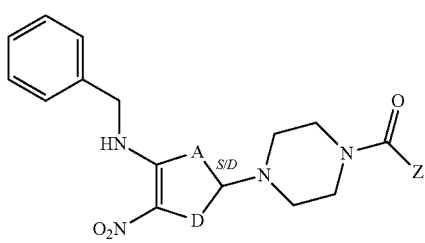

(VI)

wherein A is carbon, nitrogen, NH, oxygen, or sulfur;
D is oxygen or sulfur; and Z is phenyl optionally substituted with up to a total of three methyl and/or ethyl and/or methoxy and/or halogen and/or acetamide and/or ethoxy and/or cyano groups.

In certain embodiments, amyloid diseases may be treated, for example, by administering a therapeutically effective dose of a compound including, but not limited to: 1-(3-(benzylamino)-4-nitrophenyl)-N-phenylpiperidine-4-carboxamide, 1-(3-(benzylamino)-4-nitrophenyl)-N-phenylpiperidine-3-carboxamide, 1-(3-(benzylamino)-4-nitrophenyl)-N-phenylpiperidine-2-carboxamide, (4-(3-(benzylamino)-4-nitrophenyl)piperidin-1-yl)(phenyl)methanone, (3-(3-(benzylamino)-4-nitrophenyl)piperidin-1-yl)(phenyl)methanone, (2-(3-(benzylamino)-4-nitrophenyl)piperidin-1-yl)(phenyl)methanone, N-(2((3-(benzylamino)-4-nitrophenyl)(methyl)amino)ethyl)-N-methylbenzamide, N-(2((3-(benzylamino)-4-nitrophenyl)(methyl)amino)phenyl)-N-methylbenzamide, and 3'-(benzylamino)-4'-nitro-N-phenylbiphenyl-4-carboxamide, pharmaceutically acceptable salts, stereo-isomers, polymorphs, metabolites, analogues, pro-drugs and combinations thereof. Such compounds vary from Formula IV by containing minor alterations from the central piperazine ring; as such, we consider them to be in the scope of the methods of the invention.

In yet another embodiment, amyloid diseases may be treated, for example, by administering a therapeutically effective dose of a compound including, but not limited to: N-[2-nitro-5-[4-[(2-nitrophenyl)sulfonyl]-1-piperazinyl]phenyl]-a-methylbenzenemethanamine, N-[5-[4-[[4-(methylthio)phenyl]sulfonyl]-1-piperazinyl]-2-nitrophenyl]benzenemethanamine, N-[5-[4-[(3,4-dimethylphenyl)sulfonyl]-1-piperazinyl]-2-nitrophenyl]benzenemethanamine, N-[5-[4-[(3,4-dimethylphenyl)sulfonyl]-1-piperazinyl]-2-nitrophenyl]-a-methylbenzenemethanamine, N-[5-[4-[(4-fluorophenyl)sulfonyl]-1-piperazinyl]-2-nitrophenyl]-a-methylbenzenemethanamine, N-[2-nitro-5-[4-[(2-nitrophenyl)sulfonyl]-1-piperazinyl]phenyl]benzenemethanamine, N-[5-[4-[(4-fluorophenyl)sulfonyl]-1-piperazinyl]-2-nitrophenyl]benzenemethanamine, N-[5-[4-[(3,4-dichlorophenyl)sulfonyl]-1-piperazinyl]-2-nitrophenyl]benzenemethanamine, N-[5-[4-[(3,4-dichlorophenyl)sulfonyl]-1-piperazinyl]-2-nitrophenyl]-a-methylbenzenemethanamine, N-[5-[4-[(3-fluoro-4-methoxyphenyl)sulfonyl]-1-piperazinyl]-2-nitrophenyl]benzenemethanamine, N-[5-[4-[(3,4-dimethoxyphenyl)sulfonyl]-1-piperazinyl]-2-nitrophenyl]-a-methylbenzenemethanamine, N-[5-[4-[(3,4-dimethoxyphenyl)sulfonyl]-1-piperazinyl]-2-nitrophenyl]benzenemethanamine, N-[5-[4-[[4-(methylthio)phenyl]sulfonyl]-1-piperazinyl]-2-nitrophenyl]-a-methylbenzenemethanamine, N-[5-[4-[(3-fluoro-4-methoxyphenyl)sulfonyl]-1-piperazinyl]-2-nitrophenyl]-a-methylbenzenemethanamine, N-[5-[4-[(4-bromophenyl)sulfonyl]-1-piperazinyl]-2-nitrophenyl]-a-methylbenzenemethanamine, N-[4-[[4-[4-nitro-3-[(1-phenylethyl)amino]phenyl]-1-piperazinyl]sulfonyl]phenyl]benzenemethanamine, N-[4-[[4-[4-nitro-3-[(phenylmethyl)amino]phenyl]-1-piperazinyl]sulfonyl]phenyl]benzenemethanamine, 4-chloro-N-[5-[4-[(4-chlorophenyl)sulfonyl]-1-piperazinyl]-2-nitrophenyl]benzenemethanamine, 4-chloro-N-[2-nitro-5-[4-(phenylsulfonyl)-1-piperazinyl]phenyl]benzenemethanamine, N-[5-[4-[(4-chlorophenyl)sulfonyl]-1-piperazinyl]-2-nitrophenyl]-4-(1-methylethyl)benzenemethanamine, N-[2-nitro-5-[4-(phenylsulfonyl)-1-piperazinyl]phenyl]benzenemethanamine, N-[5-[4-[(4-chlorophenyl)sulfonyl]-1-piperazinyl]-2-nitrophenyl]benzenemethanamine, 4-(1-methylethyl)-N-[2-nitro-5-[4-(phenylsulfonyl)-1-piperazinyl]phenyl]benzenemethanamine, N-[5-[4-[(4-methylphenyl)sulfonyl]-1-piperazinyl]-2-nitrophenyl]benzenemethanamine, N-[5-[4-[(4-chlorophenyl)sulfonyl]-1-piperazinyl]-2-nitrophenyl]-a-methylbenzenemethanamine, N-[5-[4-[(4-methylphenyl)sulfonyl]-1-piperazinyl]-2-nitrophenyl]-a-methylbenzenemethanamine, 4-(1-methylethyl)-N-[5-[4-[(4-methylphenyl)sulfonyl]-1-piperazinyl]-2-nitrophenyl]benzenemethanamine, N-[2-nitro-5-[4-(phenylsulfonyl)-1-piperazinyl]phenyl]-a-methylbenzenemethanamine, N-[5-[4-[(4-bromophenyl)sulfonyl]-1-piperazinyl]-2-nitrophenyl]-4-chlorobenzenemethanamine, N-[5-[4-[(4-bromophenyl)sulfonyl]-1-piperazinyl]-2-nitrophenyl]benzenemethanamine, 4-chloro-N-[5-[4-[(4-methylphenyl)sulfonyl]-1-piperazinyl]-2-nitrophenyl]benzenemethanamine, and N-[2-nitro-5-(1-piperazinyl)phenyl]benzenemethanamine, pharmaceutically acceptable salts, stereo-isomers, polymorphs, metabolites, analogues, pro-drugs and combinations thereof. Such compounds are known and have features akin to Formula II and which generally include —SO$_2$— as Z in said formula; we therefore consider such compounds to be in the scope of the present invention.

The methods for treating amyloid diseases require administration of the compositions of the present invention to a subject to be treated using known procedures, at dosages and for periods of time effective to inhibit amyloid aggregation in the subject. An effective amount of the therapeutic compound necessary to achieve a therapeutic effect may vary according to factors such as the amount of amyloid already deposited at the clinical site in the subject, the age, sex, and weight of the subject, and the ability of the therapeutic compound to inhibit amyloid aggregation in the subject. Dosage regimens can be adjusted to provide the optimum therapeutic response. For example, several divided doses can be administered daily or the dose may be proportionally reduced as indicated by the exigencies of the therapeutic situation. A non-limiting example of an effective dose range for a therapeutic compound of the invention is between 0.05 and 500 mg/kg of body weight per day. As a non-limiting example, the compounds in the invention may be arranged to be delivered at a concentration of about 100 nM to about 5 mM; or 1 µM to about 5 mM; or 10 µM to 5 mM; or 100 µM to 5 mM. As will be appreciated by one of skill in the art, this may be the effective concentration, that is, a sufficient dosage is administered such that a concentration within one of the envisioned ranges is attained at the required site.

When administered in therapeutically effective doses, the compounds of the present invention inhibit amyloid aggregation in a subject by at least about 20%, more preferably by at least about 40%, even more preferably by at least about 60%, and still more preferably by at least about 80% relative to untreated subjects.

The ability of a compound to inhibit amyloid aggregation can be evaluated in an animal model system that may be predictive of efficacy in inhibiting amyloid aggregation in human diseases. Alternatively, the ability of a compound to inhibit amyloid aggregation can be evaluated by examining the ability of the compound to inhibit the aggregation of an amyloid protein in a binding assay, e.g. the Thioflavin T (ThT) assay as used in Example 70 below.

Many of the therapeutic compounds can be synthesized from combinatorial "building block" techniques known in the art or by utilizing standard coupling reactions upon commercially available starting materials.

The invention is further illustrated by the following examples which should not be construed as further limiting the subject invention. The contents of all references and published patent applications cited throughout this application are hereby incorporated by reference. A demonstration of efficacy of the therapeutic compounds of the present invention in the ThT assay is predicative of efficacy in humans. Unless otherwise mentioned, terms and abbreviations used below are meant to have their meaning as understood by a practitioner skilled in the art.

EXAMPLES

SCHEME 1: Examples 1-15

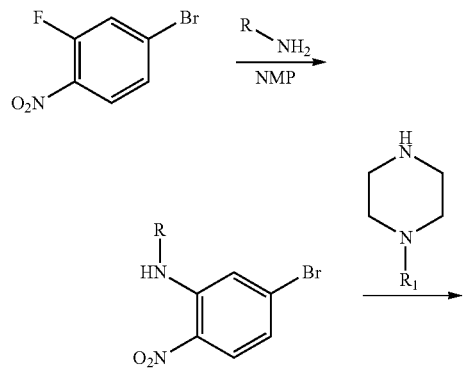

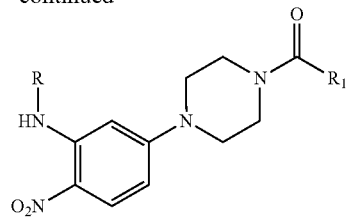

The following compounds were synthesized as intermediates for this scheme:

Example 1

5-bromo-2-nitro-N-propylbenzenamine

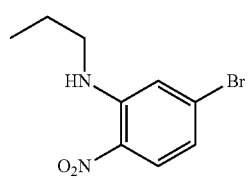

To a solution of 4-bromo-2-fluoro-1-nitrobenzene (0.5 g, 2.29 mmol) and diisopropyl ethyl amine (1.38 mL, 3.44 mmol) in NMP (5 mL) was added propylamine (0.22 mL, 2.7 mmol). The solution was stirred for 14 h to which was slowly added $H_2O$ (5 mL). The resulting yellow precipitate was filtered, washed with 2 mL of water, subjected to high vacuum for drying for 14 h to furnish 5-bromo-2-nitro-N-propylbenzenamine (520 mg, 2.18 mmol), 92% yield, which was used without further purification.

Example 2

N-phenyl-5-bromo-2-nitrobenzenamine

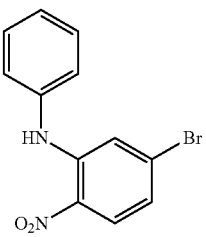 [SMILES: O=[N+]([O-])c1ccc(Br)cc1Nc1ccccc1]

To a solution of 4-bromo-2-fluoro-1-nitrobenzene (1.0 g, 4.58 mmol) and diisopropyl ethylamine (1.1 mL, 6.87 mmol) in NMP (10 mL) was added aniline (0.51 g, 5.49 mmol). The solution was stirred for 14 h to which was slowly added $H_2O$ (5 mL). The resulting yellow precipitate was filtered, washed with 5 mL of water, dried (high vacuum, 14 h) to furnish N-phenyl-5-bromo-2-nitrobenzenamine (1.2 g), 90% yield. $^1$H NMR (500 MHz, CDCl$_3$): δ 6.92 (dd, J=2 Hz, 1H), 7.35 (m, 5H), 7.51 (m, 1H) 8.11 (d, J=9.0 Hz, 1H), 9.55 (bs, 1H).

Example 3

(4-(3-(benzylamino)-4-nitrophenyl)piperazin-1-yl)(phenyl)methanone

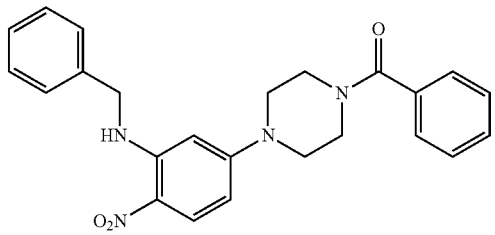 [SMILES: O=C(c1ccccc1)N1CCN(c2ccc([N+](=O)[O-])c(NCc3ccccc3)c2)CC1]

A solution of N-benzyl-5-bromo-2-nitrobenzenamine (50 mg, 0.16 mmol) and phenyl(piperazin-1-yl)methanone (93 mg, 0.48 mmol) in NMP (1 mL) was heated to 110° C. for 16 h. The solution was cooled to room temperature to which was slowly added H$_2$O (5 mL). The resulting yellow precipitate was filtered, washed with 2 mL of water, dried (high vacuum, 14 h) to furnish (4-(3-(benzylamino)-4-nitrophenyl)piperazin-1-yl)(phenyl)methanone (520 mg, 2.18 mmol), 92% yield. $^1$H NMR (500 MHz, CDCl$_3$) d (ppm) 8.85 (m, 1H), 8.14 (d, J=9.5 Hz, 1H), 7.51-7.3 (m, 10H), 6.24 (dd, J=2.5 Hz, 10 Hz, 1H), 5.88 (d, J=2.5 Hz, 1H), 4.55 (d, J=5 Hz, 2H) 3.9-3.2 (m, 8H).+ESI HRMS (calcd for C$_{24}$H$_{24}$N$_4$O$_3$Na, M+Na) 439.1746, found 439.1741

Example 4

N-benzyl-5-(4-methylpiperazin-1-yl)-2-nitrobenzenamine

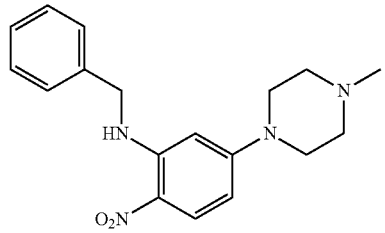 [SMILES: CN1CCN(c2ccc([N+](=O)[O-])c(NCc3ccccc3)c2)CC1]

A solution of N-benzyl-5-bromo-2-nitrobenzenamine (100 mg, 0.32 mmol) and 1-methylpiperazine (65 mg, 0.65 mmol) in NMP (1 mL) was heated to 110° C. for 16 h. The solution was cooled to room temperature to which was slowly added H$_2$O (5 mL). The resulting yellow precipitate was filtered, washed with 2 mL of water, dried (high vacuum, 14 h) to furnish N-benzyl-5-(4-methylpiperazin-1-yl)-2-nitrobenzenamine (73 mg, 0.22 mmol), 69% yield. $^1$H NMR (500 MHz, DMSO-D6) d (ppm) 8.81 (m, 1H), 7.90 (d, J=9.5 Hz, 1H), 7.44-7.34 (m, 4H), 7.30-7.25 (m, 1H), 6.41 (dd, J=2.5 Hz, 10 Hz, 1H), 5.97 (d, J=2.5 Hz, 1H), 4.58 (d, J=6 Hz, 2H) 3.4-3.2 (m, 4H), 2.34 (m, 4H), 2.19 (s, 3H).+ESI HRMS (calcd for C$_{18}$H$_{23}$N$_4$O$_2$, M+1) 327.1821, found 327.1816

Example 5

1-(4-(3-(benzylamino)-4-nitrophenyl)piperazin-1-yl)ethanone

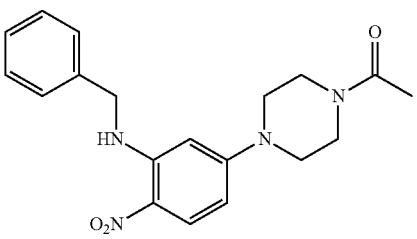 [SMILES: CC(=O)N1CCN(c2ccc([N+](=O)[O-])c(NCc3ccccc3)c2)CC1]

A solution of N-benzyl-5-bromo-2-nitrobenzenamine (100 mg, 0.32 mmol) and 1-(piperazin-1-yl)ethanone (83 mg, 0.65 mmol) in NMP (1 mL) was heated to 110° C. for 16 h, cooled then diluted with H$_2$O (15 mL) and extracted with ethyl acetate (2×15 mL). The organics were washed with brine (8 mL), dried (Na$_2$SO$_4$) then filtered and concentrated in vacuo. The residue was subjected flash silica column chromatography (100% ethyl acetate) to furnish 1-(4-(3-(benzylamino)-4-nitrophenyl)piperazin-1-yl)ethanone (mg, 0.22 mmol) as a yellow solid (71 mg, 0.19 mmol) 61% yield. $^1$H NMR (500 MHz, DMSO-D6) d (ppm) 8.83 (m, 1H), 7.93 (d, J=9.5 Hz, 1H), 7.39 (m, 4H), 7.28 (m, 1H), 6.40 (dd, J=2.5 Hz, 10 Hz, 1H), 5.96 (d, J=2.5 Hz, 1H), 4.58 (d, J=6 Hz, 2H) 3.50-3.29 (m, 8H), 2.34 (s, 3H).+ESI HRMS (calcd for C$_{19}$H$_{22}$N$_4$NaO$_3$, M+Na) 377.1590, found 377.1584

Example 6

(4-(4-nitro-3-(propylamino)phenyl)piperazin-1-yl)(phenyl)methanone

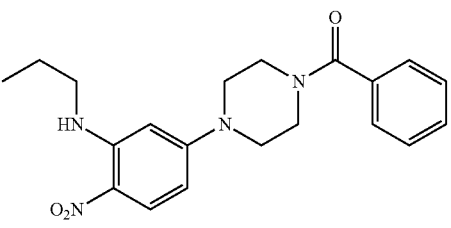 [SMILES: CCCNc1cc(N2CCN(C(=O)c3ccccc3)CC2)ccc1[N+](=O)[O-]]

A solution of 5-bromo-2-nitro-N-propylbenzenamine (250 mg, 1.02 mmol) and phenyl(piperazin-1-yl)methanone (578 mg, 3.06 mmol) in NMP (2 mL) was heated to 110° C. for 16 h. The solution was cooled to room temperature to which was slowly added H$_2$O (5 mL). The resulting yellow precipitate was filtered, washed with 2 mL of water, dried (high vacuum, 14 h) to furnish (4-(4-nitro-3-(propylamino)phenyl)piperazin-1-yl)(phenyl)methanone (520 mg, 2.18 mmol), 56% yield. $^1$H NMR (500 MHz, DMSO-D6) d (ppm) 8.83 (m, 1H), 7.93 (d, J=9.5 Hz, 1H), 7.50-7.45 (m, 5H), 6.41 (dd, J=2.5 Hz, 10 Hz, 1H), 6.00 (d, J=2.5 Hz, 1H), 3.72-3.40 (m, 8H), 3.29 (q, J=7 Hz, 2H), 1.66 (m, 2H), 0.96 (t, J=7 Hz, 3H).+ESI HRMS (calcd for C$_{20}$H$_{24}$N$_4$NaO, M+Na) 391.1746. found 391.1741

Example 7

(4-(4-nitro-3-(phenylamino)phenyl)piperazin-1-yl)(phenyl)methanone

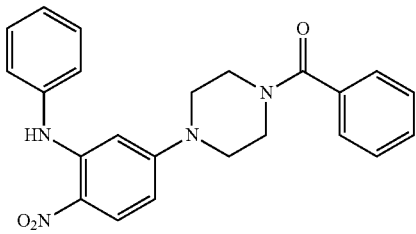

A solution of N-(5-bromo-2-nitrophenyl)benzenamine (200 mg, 0.68 mmol) and phenyl(piperazin-1-yl)methanone (257 mg, 1.36 mmol) in NMP (1.5 mL) was heated to 110° C. for 16 h. The solution was cooled to room temperature to which was slowly added $H_2O$ (5 mL). The resulting yellow precipitate was filtered, washed with 2 mL of water, dried (high vacuum, 14 h) to furnish (4-(4-nitro-3-(phenylamino)phenyl)piperazin-1-yl)(phenyl)methanone (187 mg, 0.46 mmol), 68% yield. $^1$H NMR (500 MHz, CDCl$_3$) d (ppm) 3.10-3.61 (m, 8H), 6.34 (dd, J=2.6, 9.7 Hz, 1H), 6.41 (d, J=2.6 Hz, 1H), 7.24-7.48 (m, 10H), 8.19 (d, J=9.7 Hz, 1H), 9.86 (s, 1H). $^{13}$C NMR (125 MHz, CDCl$_3$): d (ppm) 171.0, 155.7, 145.8, 139.3, 135.5, 130.6, 130.2, 129.4, 129.1, 127.6, 126.1, 125.0, 106.2, 96.9, 46.7, 29.9.

Example 8

2-nitro-N-phenyl-5-(piperazin-1-yl)aniline

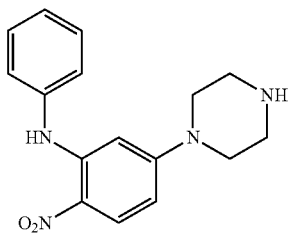 [SMILES: O=[N+]([O-])c1ccc(N2CCNCC2)cc1Nc1ccccc1]

A solution of N-(5-bromo-2-nitrophenyl)benzenamine (250 mg, 0.85 mmol) and piperazine (366 mg, 4.26 mmol) in NMP (1 mL) was heated to 110° C. for 16 h. The solution whole cooled to room temperature to which was slowly added $H_2O$ (5 mL). The resulting yellow precipitate was filtered, washed with 10 mL of water, dried (high vacuum, 14 h) to furnish 2-nitro-N-phenyl-5-(piperazin-1-yl)aniline (165 mg, 0.55 mmol), 65% yield. $^1$H NMR (500 MHz, CDCl$_3$) d (ppm) 9.89 (s, 1H), 8.15 (d, J=9.0 Hz, 1H), 7.45 (m, 2H), 7.34 (d, J=7.0 Hz, 2H), 7.25 (t, J=7.0 Hz, 1H), 6.43 (d, J=2.5 Hz, 1H), 6.35 (dd, 2.5 Hz, 9.75 Hz, 1H), 3.29 (m, 4H), 2.92 (m, 4H).+ESI HRMS (calcd for $C_{16}H_{19}N_4O_2$, M+1) 299.1508, found 391.150

Example 9

(4-(4-nitro-3-phenoxyphenyl)piperazin-1-yl)(phenyl)methanone

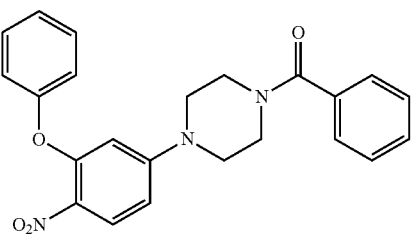 [SMILES: O=C(c1ccccc1)N1CCN(c2ccc([N+](=O)[O-])c(Oc3ccccc3)c2)CC1]

A solution of 4-bromo-2-fluoro-1-nitrobenzene (0.6 g, 2.75 mmol) phenol (0.28 g, 3.02 mmol) and cesium carbonate (1.8 g, 5.5 mmol) in NMP (6 mL) was heated at 70° C. for 12 h, cooled then diluted with $H_2O$ (15 mL) and extracted with ethyl acetate (3×10 mL). The organics were washed with brine (8 mL), dried ($Na_2SO_4$) then filtered and concentrated in vacuo. The colorless solid was dissolved in NMP (2 mL) to which was added phenyl(piperazin-1-yl)methanone (1.0 g, 5.5 mmol) and the solution was heated to 110° C. for 16 h. The mixture was cooled and then diluted with $H_2O$ (15 mL) and extracted with ethyl acetate (3×10 mL). The organics were washed with brine (8 mL), dried ($Na_2SO_4$) then filtered and concentrated in vacuo. The residue was subjected to silica gel column chromatography (20% ethyl acetate/hexane) to furnish (4-(4-nitro-3-phenoxyphenyl)piperazin-1-yl)(phenyl)methanone (0.72 g, 1.8 mmol) as a yellow gum, 65% yield. $^1$H NMR (500 MHz, CDCl$_3$) d (ppm) 8.11 (d, J=9.5 Hz, 1H), 7.51-7.47 (m, 5H), 7.39 (t, J=8.0 Hz, 2H), 7.18 (t, J=7.5 Hz, 1H), 7.05 (m, 2H), 6.64 (dd, J=2.5 Hz, 9.5 Hz, 1H), 6.35 (d, J=2.5 Hz, 1H), 4.1-3.1 (m, 8H).+ESI HRMS (calcd for $C_{23}H_{21}N_3NaO_4$, M+Na) 426.1430, found 426.1424

Example 10

2-nitro-N-phenyl-5-(piperidin-1-yl)benzenamine

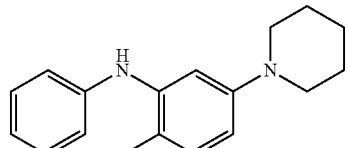

A solution of 4-bromo-2-fluoro-1-nitrobenzene (10.0 g, 45 mmol), diisopropanylethylamine (15.8 ml, 90 mmol) and aniline (5.0 ml, 54 mmol) in 100 ml 1-methylpyrrolidin-2-one (NMP) was heated at 100° C. for 16 hours. The solution was cooled to room temperature and added 1,000 ml water. The result red precipitate was filtered and washed with water (100 ml), dried under high vacuum to obtain 5-bromo-2-nitro-N-phenylbenzenamine (10.3 g, 77%). A solution of 5-bromo-2-nitro-N-phenylbenzenamine (0.50 g, 1.7 mmol) and piperidine (0.67 ml, 6.8 mmol) in 10 ml NMP was heated at 100° C. for 16 hours. The reaction was quenched with 100 ml water. The mixture was extracted with ethyl acetate (3×20 ml) and dried over anhydrous sodium sulfate. 2-Nitro-N-phenyl-5-(piperidin-1-yl)benzenamine (0.50 g, 100%) was obtained by flash column chromatograph (30% acetyl acetate in hexanes). $^1$H NMR (500 MHz, CDCl$_3$) δ (ppm) 1.66 (m, 6H), 3.33 (t, J=5.8 Hz, 4H), 6.34 (dd, J=2.6, 9.7 Hz, 1H), 6.42 (d, J=2.6 Hz, 1H), 7.23-7.46 (m, 5H), 8.14 (d, J=9.7 Hz, 1H), 9.93 (s, 1H). $^{13}$C NMR (125 MHz, CDCl$_3$): δ (ppm) 24.8, 25.4, 48.7, 95.6, 106.4, 124.8, 125.6, 129.4, 130.1, 139.7, 146.0, 156.0.

Example 11

5-morpholino-2-nitro-N-phenylbenzenamine

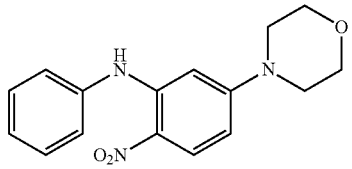 [SMILES: O=[N+]([O-])c1ccc(N2CCOCC2)cc1Nc1ccccc1]

A solution of 5-bromo-2-nitro-N-phenylbenzenamine (0.50 g, 1.7 mmol) and morpholine (0.59 g, 6.8 mmol) in 15 ml NMP was heated at 100° C. for 16 hours. The reaction was quenched with 100 ml water. The mixture was extracted with ethyl acetate (3×30 ml) and dried over anhydrous sodium sulfate. 5-Morpholino-2-nitro-N-phenylbenzenamine (0.42 g, 80%) was obtained by flash column chromatograph (30% acetyl acetate in hexanes). $^1$H NMR (500 MHz, CDCl$_3$) δ (ppm) 3.26 (t, J=5.2 Hz, 4H), 3.81 (t, J=5.2 Hz, 4H), 6.37 (d, J=2.7, 9.7 Hz, 1H), 6.45 (d, J=2.7 Hz, 1H), 7.25-7.47 (m, 5H), 8.18 (d, J=9.7 Hz, 1H), 9.87 (s, 1H). $^{13}$C NMR (125 MHz, CDCl$_3$): δ (ppm) 47.5, 66.7, 96.6, 105.9, 125.0, 126.0, 129.4, 130.2, 139.4, 145.8, 156.0.

Example 12

5-(4-methylpiperazin-1-yl)-2-nitro-N-phenylbenzenamine hydrochloride

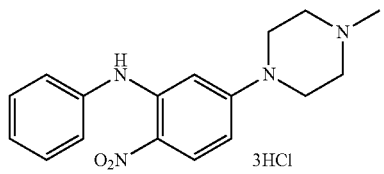

A solution of 5-bromo-2-nitro-N-phenylbenzenamine (1.0 g, 3.4 mmol) and 1-methylpiperazine (1.50 ml, 13.6 mmol) in 15 ml NMP was heated at 100° C. for 16 hours. The reaction was quenched with 100 ml water. The mixture was extracted with ethyl acetate (3×30 ml) and dried over anhydrous sodium sulfate. 5-(4-methylpiperazin-1-yl)-2-nitro-N-phenylbenzenamine (0.50 g, 49%) was obtained by flash column chromatograph (10% ethanol in dichloromethane). 5-(4-methylpiperazin-1-yl)-2-nitro-N-phenylbenzenamine hydrochloride was made by bubbling HCl gas in its ethyl ether solution and crystallized. $^1$H NMR (500 MHz, DMSO-d$_6$) δ (ppm) 2.75 (s, 3H), 3.03 (dd, J=12.9, 12.0 Hz, 2H), 3.29 (dd, J=11.9, 12.9 Hz, 2H), 3.42 (d, J=12.0 Hz, 2H), 3.90 (d, J=12.9, Hz, 2H), 6.48 (d, J=1.5 Hz, 1H), 6.65 (dd, J=2.6, 9.7 Hz, 1H), 7.2 (m, 1H), 7.23-7.45 (m, 4H), 8.06 (d, J=9.7 Hz, 1H), 9.72 (s, 1H), 11.27 (s, 1H). $^{13}$C NMR (125 MHz, DMSO-d$_6$): δ (ppm) 40.0, 43.4, 51.5, 96.7, 106.8, 123.5, 124.9, 128.3, 129.6, 138.9, 144.2, 154.5.

Example 13

N$^1$,N$^1$-dimethyl-4-nitro-N$^3$-phenylbenzene-1,3-diamine

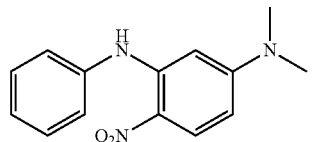

A solution of 5-bromo-2-nitro-N-phenylbenzenamine (0.2 g, 0.68 mmol) and 2.0 M dimethylamine in tetrahydrofuran (1.3 ml, 2.7 mmol) in 10 ml NMP was heated at 100° C. for 16 hours. The reaction was quenched with 100 ml water. The mixture was extracted with ethyl acetate (3×30 ml) and dried over anhydrous sodium sulfate. N$^1$,N$^1$-dimethyl-4-nitro-N$^3$-phenylbenzene-1,3-diamine (0.17 g, 100%) was obtained by flash column chromatograph (30% ethyl acetate in hexanes). $^1$H NMR (500 MHz, CDCl$_3$) δ (ppm) 3.02 (s, 6H), 6.21 (d, J=2.6 Hz, 1H), 6.23 (s, 1H), 7.22-7.45 (m, 5H), 8.17 (d, J=2.6 Hz, 1H), 9.96 (s, 1H). $^{13}$C NMR (125 MHz, CDCl$_3$): δ (ppm) 40.5, 93.6, 104.8, 124.9, 125.4, 129.5, 130.0, 139.8, 145.9, 155.5.

Example 14

N-(5-(4-benzoylpiperazin-1-yl)-2-nitrophenyl)acetamide

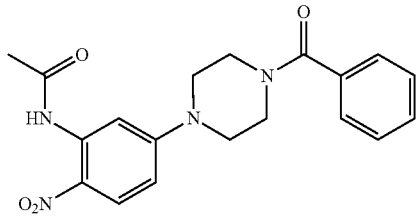 [SMILES: CC(=O)Nc1cc(N2CCN(C(=O)c3ccccc3)CC2)ccc1[N+](=O)[O-]]

A solution of 5-bromo-2-nitrobenzenamine (0.5 g, 2.3 mmol), acetyl chloride (0.18 ml, 2.5 mmol) and potassium carbonate (0.64 g, 4.6 mmol) was stirred at 0° C. for 2 hours. The mixture was washed with water (2×10 ml) and dried over anhydrous sodium sulfate before removing the solvents. Crude N-(5-bromo-2-nitrophenyl)acetamide (0.40 g, 70%) was obtained after removing of the solvents. A solution of N-(5-bromo-2-nitrophenyl)acetamide (0.3 g, 1.1 mmol) and benzoyl piperazine (0.44 g, 2.3 mml) was stirred at 105° C. under argon atmosphere for 16 hours. The reaction was quenched with 500 ml water and extracted with ethyl acetate (2×10 ml). N-(5-(4-benzoylpiperazin-1-yl)-2-nitrophenyl) acetamide (0.4 g, 93%) was obtained after flash column chromatograph (50% ethyl acetate in hexanes). $^1$H NMR (500 MHz, CDCl$_3$) δ (ppm) 2.31 (s, 3H), 3.40-3.57 (m, 8H), 6.56

(dd, J=2.8, 9.7 Hz, 1H), 7.48 (m, 5H), 8.21 (d, J=9.7 Hz, 1H), 8.38 (d, J=9.7 Hz, 1H), 11.0 (s, 1H). $^{13}$C NMR (125 MHz, CDCl$_3$): δ (ppm) 26.4, 47.1, 47.3, 61.4, 103.8, 108.5, 127.2, 127.6, 129.0, 129.1, 130.7, 135.5, 138.3, 155.7, 170.1, 171.1

Example 15

(4-(3-(dimethylamino)-4-nitrophenyl)piperazin-1-yl)(phenyl)methanone

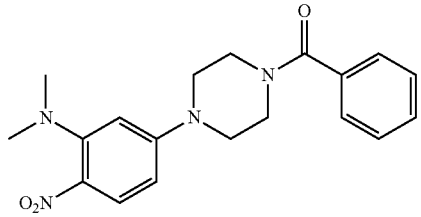 [SMILES: CN(C)c1cc(N2CCN(C(=O)c3ccccc3)CC2)ccc1[N+](=O)[O-]]

A solution of 4-bromo-2-fluoro-1-nitrobenzene (1.0 g, 4.5 mmol) and 2.0 M dimethylamine ethanol solution (6.9 ml, 13.6 mmol) in 20 ml NMP was stirred at room temperature for 16 hours. The solution was added 200 ml water. The solids (1.03 g, 90%) were filtered dried under high vacuum. A solution of 5-bromo-N,N-dimethyl-2-nitrobenzenamine (0.2 g, 0.8 mmol), benzoyl piperazine (0.19 g, 1.0 mml), Tris(dibenzylideneacetone)dipalladium (9 mg), BINAP (38 mg) and cesium carbonate (0.24 g, 1.2 mmol) in 20 ml NMP was stirred at 100° C. under argon atmosphere for 16 hours. The reaction was cooled to room temperature before filtration. (4-(3-(dimethylamino)-4-nitrophenyl)piperazin-1-yl)(phenyl)methanone (0.06 g, 20%) was obtained after flash column chromatograph (50% ethyl acetate in hexanes). $^1$H NMR (500 MHz, CDCl$_3$) δ (ppm) 2.93 (s, 6H), 3.40-3.57 (m, 8H), 6.26 (d, J=2.6 Hz, 1H), 6.35 (dd, J=2.6, 9.6 Hz, 1H), 7.48 (m, 5H), 7.98 (d, J=9.6 Hz, 1H).

SCHEME 2: Examples 16-19

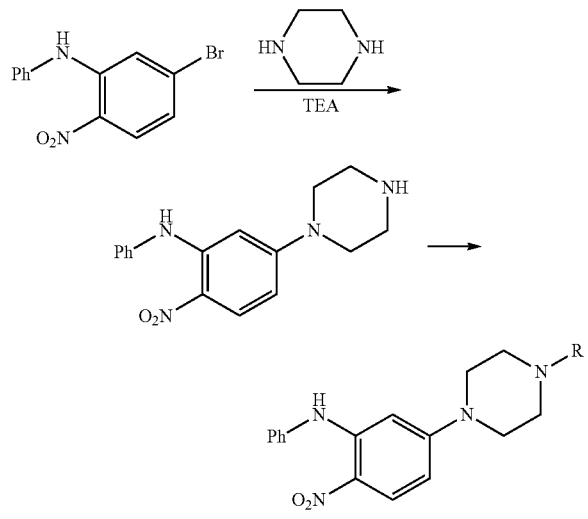

The following exemplary compounds were obtained using this scheme:

Example 16

N-(5-(4-benzylpiperazin-1-yl)-2-nitrophenyl)benzenamine

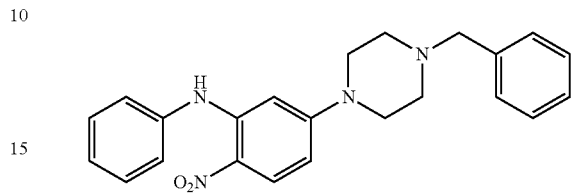

A solution of 5-bromo-2-nitro-N-phenylbenzenamine (4.0 g, 13.6 mmol) and piperazine (4.7 g, 54.6 mmol) in 40 ml NMP was heated at 100° C. for 16 hours. The reaction was quenched with 100 ml water. The mixture was extracted with ethyl acetate (3×30 ml) and dried over anhydrous sodium sulfate. 2-Nitro-N-phenyl-5-(piperazin-1-yl)benzenamine (3.5 g, 86%) was obtained by flash column chromatograph (10% methanol in dichoromethane). A solution of 2-nitro-N-phenyl-5-(piperazin-1-yl)benzenamine (0.5 g, 1.7 mmol), benzyl bromide (0.2 g, 1.7 mmol) and triethylamine (0.60 ml, 4.19 mmol) in 20 ml dichloromethane was stirred at 0° C. for 2 hours. The mixture was washed with water (2×10 ml) and dried over anhydrous sodium sulfate before removing the solvents. N-(5-(4-benzylpiperazin-1-yl)-2-nitrophenyl)benzenamine (0.30 g, 43%) was obtained by flash column chromatograph (50% ethyl acetate in hexanes). $^1$H NMR (500 MHz, CDCl$_3$) δ (ppm) 2.54 (t, J=5.0 Hz, 4H), 3.32 (t, J=2.0 Hz, 4H), 3.56 (s, 2H), 6.34 (dd, J=9.7, 2.1 Hz, 1H), 6.42 (d, J=2.5 Hz, 1H), 7.22-7.44 (m, 9H), 8.14 (d, J=9.7 Hz, 1H), 9.90 (s, 1H). $^{13}$C NMR (125 MHz, CDCl$_3$): δ (ppm) 47.3, 53.0, 63.3, 96.2, 106.2, 124.9, 125.8, 127.8, 128.9, 129.3, 129.6, 130.1, 138.0, 139.5, 145.9, 156.1.

Example 17

N-(2-nitro-5-(4-tosylpiperazin-1-yl)phenyl)benzenamine

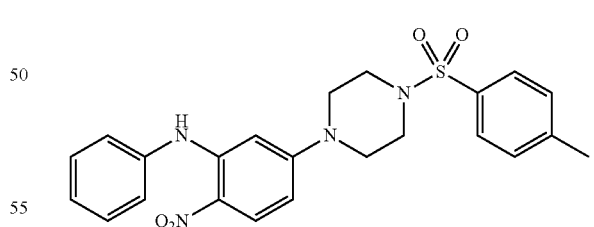

A solution of 2-nitro-N-phenyl-5-(piperazin-1-yl)benzenamine (0.5 g, 1.7 mmol), 4-methylbenzene-1-sulfonyl chloride (0.32 g, 1.7 mmol) and triethylamine (0.60 ml, 4.2 mmol) in 20 ml dichloromethane was stirred at 0° C. for 2 hours. The mixture was washed with water (2×10 ml) and dried over anhydrous sodium sulfate before removing the solvents. N-(2-nitro-5-(4-tosylpiperazin-1-yl)phenyl)benzenamine (0.30 g, 40%) was obtained by flash column chromatograph (50% ethyl acetate in hexanes). $^1$H NMR (500 MHz, CDCl$_3$) δ (ppm) 2.46 (s, 3H), 3.24 (t, J=4.5 Hz, 4H), 3.42 (t, J=4.5 Hz, 4H), 6.42 (d, J=9.6 Hz, 1H), 6.64 (s, 1H), 7.28-7.65 (m, 9H), 8.14 (d, J=9.5 Hz, 1H), 9.90 (s, 1H). $^{13}$C NMR (125 MHz, CDCl$_3$): δ (ppm) 22.0, 45.5, 48.4, 48.5, 99.5, 99.6, 125.0, 106.8, 126.4, 128.2, 129.6, 130.3, 130.4, 132.7, 138.9, 144.8, 145.6.

Example 18

5-(4-methansulfonylpiperazin-1-yl)-2-nitro-N-phenylbenzenamine

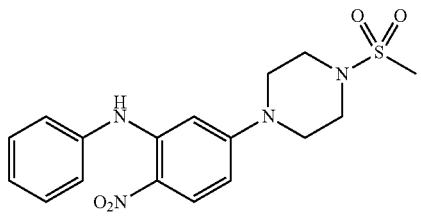 [SMILES: CS(=O)(=O)N1CCN(c2ccc([N+](=O)[O-])c(Nc3ccccc3)c2)CC1]

A solution of 2-nitro-N-phenyl-5-(piperazin-1-yl)benzenamine (0.30 g, 1.0 mmol), methanesulfonyl chloride (0.08 ml, 1.0 mmol) and triethylamine (0.32 ml, 4.0 mmol) in 20 ml dichloromethane was stirred at 0° C. for 2 hours. The mixture was washed with water (2×10 ml) and dried over anhydrous sodium sulfate before removing the solvents. 5-(4-methansulfonylpiperazin-1-yl)-2-nitro-N-phenylbenzenamine (0.20 g, 52%) was obtained by flash column chromatograph (30% ethyl acetate in hexanes). $^1$H NMR (500 MHz, DMSO-d$_6$) δ (ppm) 2.90 (s, 3H), 3.20 (t, J=5.3 Hz, 4H), 3.42 (t, J=5.3 Hz, 4H), 6.46 (d, J=3.6, 1H), 6.62 (dd, J=3.6, 9.7 Hz, 1H), 7.21-7.46 (m, 5H), 8.05 (d, J=9.7 Hz, 1H), 9.74 (s, 1H). $^{13}$C NMR (125 MHz, DMSO-d$_6$): δ (ppm) 34.2, 44.7, 45.9, 95.9, 106.6, 123.5, 124.8, 128.3, 129.6, 138.9, 144.3, 154.9.

Example 19

5-(4-dimethylcarbamylpiperazin-1-yl)-2-nitro-N-phenylbenzenamine

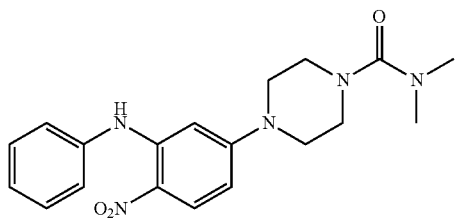 [SMILES: CN(C)C(=O)N1CCN(c2ccc([N+](=O)[O-])c(Nc3ccccc3)c2)CC1]

A solution of 2-nitro-N-phenyl-5-(piperazin-1-yl)benzenamine (0.30 g, 1.0 mmol), dimethylcarbamic chloride (0.09 ml, 1.0 mmol) and triethylamine (0.16 ml, 2.0 mmol) in 20 ml dichloromethane was stirred at 0° C. for 2 hours. The mixture was washed with water (2×10 ml) and dried over anhydrous sodium sulfate before removing the solvents. 5-(4-dimethylcarbamylpiperazin-1-yl)-2-nitro-N-phenylbenzenamine (0.35 g, 95%) was obtained by flash column chromatograph (50% ethyl acetate in hexanes). $^1$H NMR (500 MHz, CDCl$_3$) δ (ppm) 2.88 (s, 6H), 3.31 (dd, J=1.5, 6.4 Hz, 4H), 3.42 (dd, J=1.5, 6.4 Hz, 4H), 6.34 (dd, J=2.6, 9.6 Hz, 1H), 6.41 (d, J=2.6 Hz, 1H), 7.26-7.47 (m, 5H), 8.17 (d, J=9.6 Hz, 1H), 9.88 (s, 1H). $^{13}$C NMR (125 MHz, CDCl$_3$): δ (ppm) 38.9, 46.6, 47.0, 60.9, 96.5, 106.2, 125.0, 126.0, 129.4, 130.2, 139.4, 145.9, 156.0, 164.8.

SCHEME 3: Examples 20-21

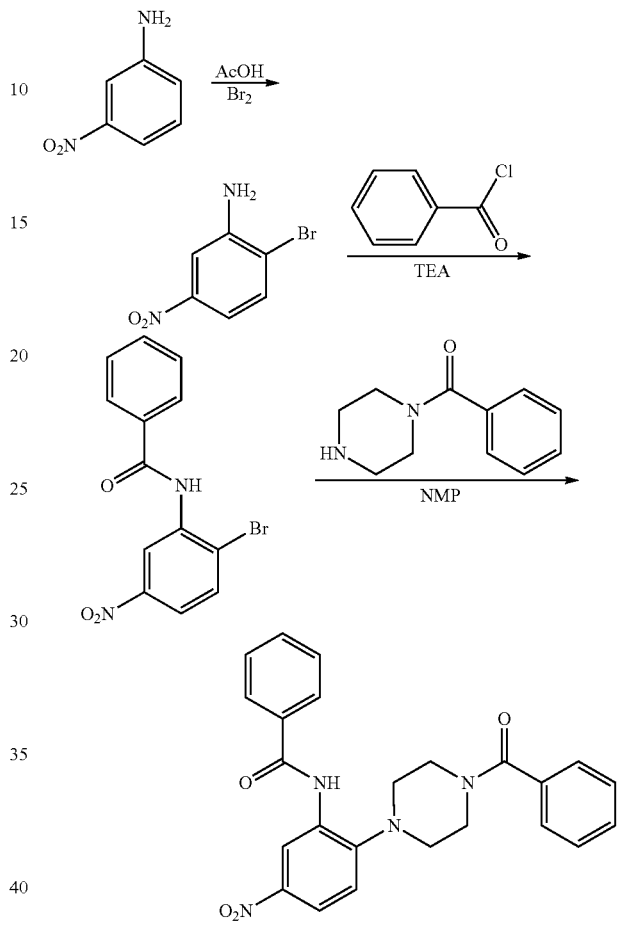

The following exemplary compound was obtained using this scheme:

Example 20

N-(2(4-benzoylpiperazin-1-yl)-5-nitrophenyl)benzamide

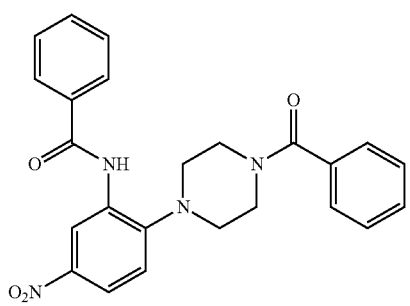 [SMILES: O=C(Nc1cc([N+](=O)[O-])ccc1N1CCN(C(=O)c2ccccc2)CC1)c1ccccc1]

To a solution of 3-nitroaniline (0.5 g, 3.6 mmol) in 10 ml acetic acid added bromine (0.2 ml, 4.0 mmol) and stirred at 0° C. for 1 hour. The solution was filtered after recovering to room temperature to obtain 2-bromo-5-nitrobenzenamine (0.32 g, 40%) as a powder. A solution of 2-bromo-5-nitrobenzenamine (0.4 g, 1.8 mmol), sodium hydroxide (0.14 g, 3.6 mmol) and benzoyl chloride (0.24 ml, 2.0 mmol) in 20 ml THF was stirred for 2 hours in icy water bath. The reaction was quenched and washed with water (3×20 ml). The mixture was dried over anhydrous sodium sulfate. The crude N-(2-bromo-5-nitrophenyl)benzamide (0.3 g, 50%) was obtained after evaporation of the solvents. $^1$H NMR (500 MHz, CDCl$_3$) δ (ppm) 7.65 (m, 2H), 7.68 (m, 1H), 7.80 (d, J=8.8 Hz, 1H), 7.94 (dd, J=8.8, 2.7 Hz, 1H), 8.00 (m, 2H), 8.62 (s, 1H), 9.55 (d, J=2.7 Hz, 1H).

N-(2-bromo-5-nitrophenyl)benzamide (0.3 g, 0.9 mmol) and benzoylpiperazine (0.53 g, 3.00 mmol) were dissolved in 15 NMP and heated at 125° C. for 16 hours. The reaction was quenched with 100 ml water after cooling to room temperature. The mixture was extracted with 50 ml acetyl acetate and washed by water (3×20 ml). N-(2-(4-benzoylpiperazin-1-yl)-5-nitrophenyl)benzamide (0.20 g, 50%) was obtained after flash column chromatograph (50% ethyl acetate in hexanes). $^1$H NMR (500 MHz, CDCl$_3$) δ (ppm) 3.06 (s, br, 4H), 3.85 (d, br, 4H), 7.31 (d, J=8.8 Hz, 1H), 7.48 (m, 5H), 7.62 (m, 2H), 7.65 (m, 1H), 7.95 (d, J=7.1 Hz, 2H), 8.06 (dd, J=2.6, 8.8 Hz, 1H), 9.12 (s, 1H), 9.47 (d, J=2.6 Hz, 1H). $^{13}$C NMR (125 MHz, CDCl$_3$): δ (ppm) 52.4, 115.9, 119.9, 121.0, 127.3, 127.6, 129.2, 129.7, 130.7, 133.0, 134.2, 134.5, 135.5, 145.9, 146.7, 165.3, 171.2.

The following exemplary compound was synthesized using a related scheme:

SCHEME 4: Examples 22-25

Example 21

N-methyl-5-(4-benzoylpiperazin-1-yl)-2-nitro-N-phenylbenzenamine

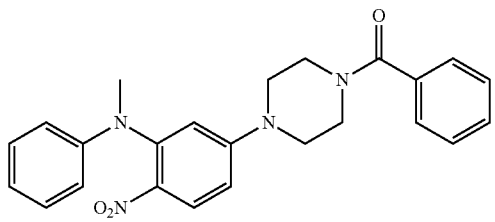

A solution of 5-(4-benzoylpiperazin-1-yl)-2-nitro-N-phenylbenzenamine (2.0 g, 5.00 mmol), methyl iodide (0.31 ml, 5.00 mmol) and sodium hydroxide (0.26 g, 6.5 mmol) in 25 ml DMF was stirred at 0° C. for 2 hours. 100 ml water was added to the mixture to quench the run, and the mixture was extracted with ethyl acetate (2×20 ml). The extraction was washed with water (3×30 ml) and dried over anhydrous sodium sulfate. N-methyl-5-(4-benzoylpiperazin-1-yl)-2-nitro-N-phenylbenzenamine (1.8 g, 90%) was obtained after remove of solvents. $^1$H NMR (500 MHz, CDCl$_3$) δ (ppm) 3.38 (s, 3H), 3.37-3.87 (m, 8H), 6.72 (m, 4H), 6.84 (m, 1H), 7.21 (m, 2H), 7.45 (m, 5H), 8.07 (d, J=9.9 Hz, 1H). $^{13}$C NMR (125 MHz, CDCl$_3$): δ (ppm) 40.5, 47.7, 47.9, 111.1, 114.6, 115.3, 119.8, 127.6, 129.1, 129.2, 129.6, 130.7, 135.6, 137.3, 145.4, 148.4, 155.1, 171.0.

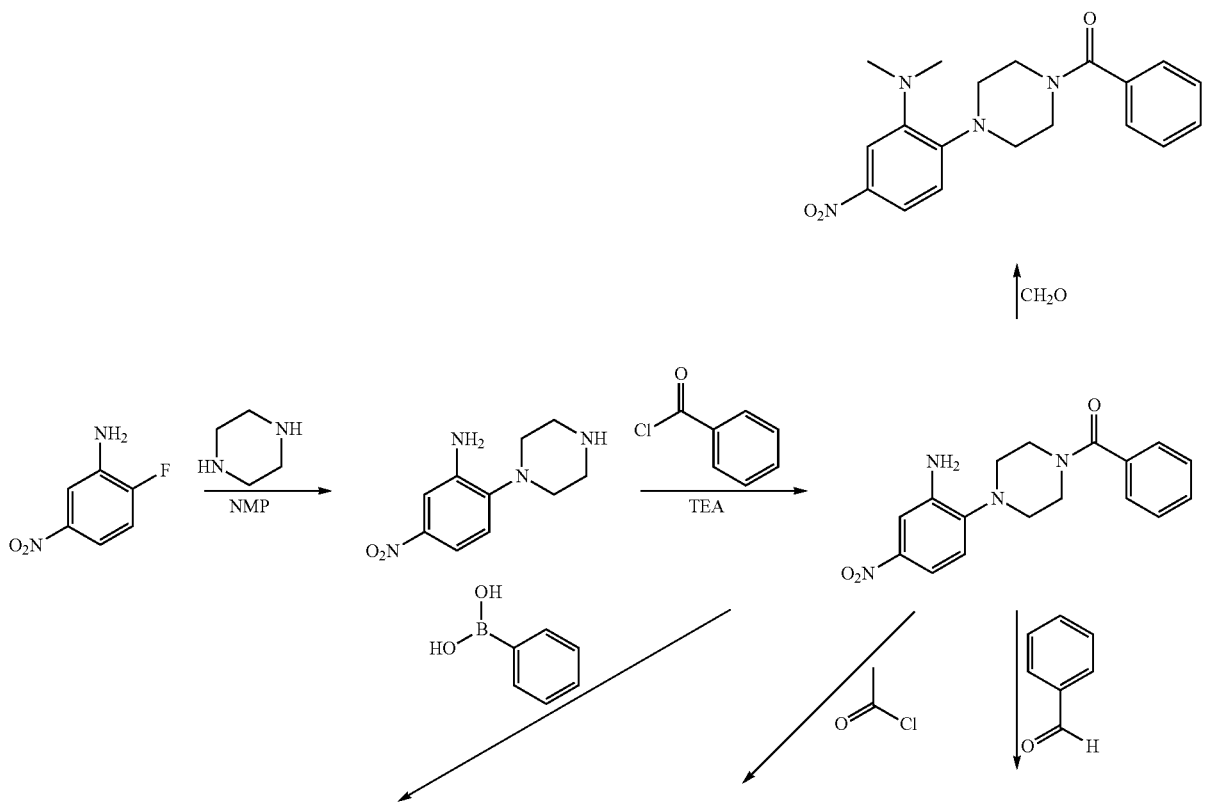

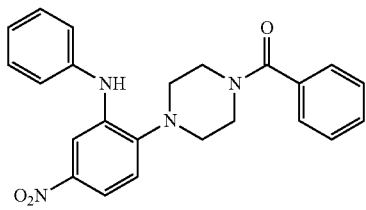 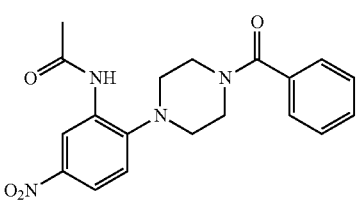 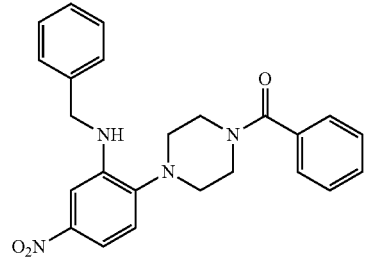

The following exemplary compounds were synthesized using this scheme:

Example 22

N-(2-(4-benzoylpiperazin-1-yl)-5-nitrophenyl)acetamide

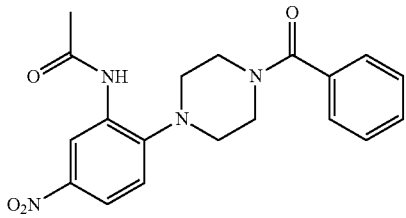 [SMILES: CC(=O)Nc1cc([N+](=O)[O-])ccc1N1CCN(C(=O)c2ccccc2)CC1]

A solution of 2-fluoro-5-nitrobenzenamine (0.50 g, 3.2 mmol) and piperazine (0.83 g, 9.6 mmol) in 15 ml NMP was heated at 100° C. for 16 hours. The reaction was quenched with 100 ml water. Red solids were filtered and dried under high vacuum. 5-Nitro-2-(piperazin-1-yl)benzenamine (0.50 g, 70%) was obtained by crystallization in acetyl acetate and hexanes. $^1$H NMR (500 MHz, DMSO-$d_6$) δ (ppm) 2.23 (s, 1H), 2.86 (m, 8H), 5.26 (s, 2H), 6.98 (d, J=8.7 Hz, 1H), 7.45 (dd, J=8.7, 2.8 Hz, 1H), 7.54 (d, J=8.7 Hz, 1H).

A solution of 5-nitro-2-(piperazin-1-yl)benzenamine (2.4 g, 10.7 mmol), benzoyl chloride (1.2 ml, 12.8 mmol) and triethylamine (6.0 ml, 42.7 mmol) in 40 ml DCM was stirred at 0° C. for 2 hours. The mixture was washed with water (2×10 ml) and dried over anhydrous sodium sulfate before removing the solvents. (4-(2-Amino-4-nitrophenyl)piperazin-1-yl)(phenyl)methanone (3.0 g, 86%) was obtained by flash column chromatograph (40% ethyl acetate in hexanes). A solution of (4-(2-amino-4-nitrophenyl)piperazin-1-yl)(phenyl)methanone (0.3 g, 0.9 mmol), acetyl chloride (0.065 ml, 0.9 mmol) and sodium hydroxide (0.037 g, 0.9 mmol) in 20 ml THF was stirred at 0° C. for 2 hours. The mixture was concentrated. N-(2-(4-benzoylpiperazin-1-yl)-5-nitrophenyl)acetamide (0.11 g, 32%) was obtained by flash column chromatograph (65% ethyl acetate in hexanes). $^1$H NMR (500 MHz, CDCl$_3$) δ (ppm) 2.29 (s, 3H), 3.00 (s, br, 4H), 3.84 (s, br, 4H), 7.23 (d, J=8.8 Hz, 1H), 7.47-7.51 (m, 5H), 8.00 (dd, J=8.6, 2.6 Hz, 1H), 8.16 (s, br, 1H), 9.24 (s, 1H). $^{13}$C NMR (125 MHz, CDCl$_3$): δ (ppm) 25.3, 52.3, 116.0, 119.9, 120.8, 127.6, 129.2, 130.7, 135.6, 171.2.

Example 23

N-benzyl-2-(4-benzoylpiperazin-1-yl)-5-nitrobenzenamine

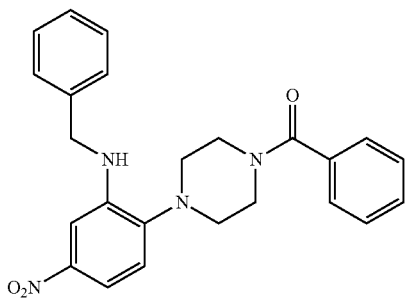 [SMILES: O=C(c1ccccc1)N1CCN(c2ccc([N+](=O)[O-])cc2NCc2ccccc2)CC1]

A solution of (4-(2-amino-4-nitrophenyl)piperazin-1-yl)(phenyl)methanone (0.4 g, 1.2 mmol) and benzaldehyde (0.18 ml, 1.8 mmol) in 15 ml dichloroethane was stirred for 10 min, followed by the addition of sodium triacetoxyborohydride (0.78 g, 3.68 mmol). The mixture was stirred overnight under argon atmosphere. The reaction was quenched with water and extracted with ethyl acetate (3×20 ml), followed by drying over anhydrous sodium sulfate. N-benzyl-2-(4-benzoylpiperazin-1-yl)-5-nitrobenzenamine (0.1 g, 19%) was obtained by flash column chromatograph (50% ethyl acetate in hexanes). $^1$H NMR (500 MHz, CDCl$_3$) δ (ppm) 3.00-3.60 (d, br, 8H), 4.44 (d, J=5.5 Hz, 2H), 5.04 (t, J=5.5 Hz, 1H), 7.06 (d, J=8.6 Hz, 1H), 7.34-7.65 (m, 11H), 7.67 (dd, J=8.6, 2.5 Hz, 1H). $^{13}$C NMR (125 MHz, CDCl$_3$): δ (ppm) 48.6, 51.3, 105.5, 113.6, 119.3, 127.6, 127.7, 128.2, 129.1, 129.4, 130.5, 135.9, 138.7, 143.4, 144.3, 146.0, 171.1.

Example 24

N-(2-(4-benzoylpiperazin-1-yl)-5-nitrophenyl)benzenamine

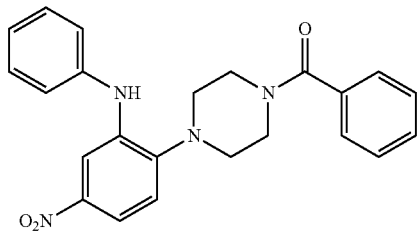 [SMILES: O=C(c1ccccc1)N1CCN(c2ccc([N+](=O)[O-])cc2Nc2ccccc2)CC1]

A suspension of (4-(2-amino-4-nitrophenyl)piperazin-1-yl)(phenyl)methanone (0.4 g, 1.2 mmol), copper acetate (0.45 g, 2.5 mmol), potassium phosphate (0.26 g, 1.2 mmol), 18-C-6 (31 mg, 0.12 mmol), 4 Å molecular sieves (1.0 g) and phenylboronic acid and pyridine complex (1.4 g, 3.7 mmol) in 30 ml dry dichloromethane was stirred at room temperature overnight. The reaction was quenched with 20 ml water. The mixture was filtered and extracted with ethyl acetate (3×20 ml), followed by drying over anhydrous sodium sulfate. N-(2-(4-benzoylpiperazin-1-yl)-5-nitrophenyl)benzenamine (0.11 g, 20%) was obtained by flash column chromatograph (50% ethyl acetate in hexanes). $^1$H NMR (500 MHz, CDCl$_3$) δ (ppm) 3.08 (s, br, 4H), 3.70 (s, br, 4H), 6.43 (s, 1H), 7.12-7.75 (m, 11H), 7.77 (d, J=2.4 Hz, 1H), 8.09 (s, 1H). $^{13}$C NMR (125 MHz, CDCl$_3$): δ (ppm) 51.4, 108.9, 115.8, 120.2, 120.7, 123.8, 127.6, 128.5, 129.1, 130.3, 130.5, 135.8, 139.1, 141.1, 145.5, 145.9, 171.1.

Example 25

N,N-dimethyl-2-(4-benzoylpiperazin-1-yl)-5-nitrobenzenamine

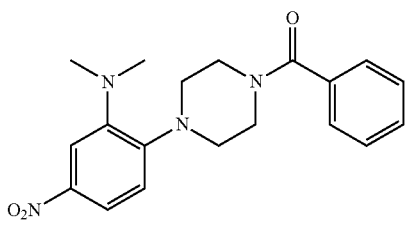 [SMILES: CN(C)c1cc([N+](=O)[O-])ccc1N1CCN(C(=O)c2ccccc2)CC1]

A solution of (4-(2-amino-4-nitrophenyl)piperazin-1-yl)(phenyl)methanone (0.4 g, 1.2 mmol) and 30 ml formaldehyde ether solution extracted from 30 ml 37% water formaldehyde solution in 20 ml acetic acid was stirred for 10 min, followed by the addition of sodium cyanoborohydride (0.13 g, 2.5 mmol). The mixture was stirred for 3 hours under argon atmosphere. The reaction was quenched with water and extracted with ethyl acetate (3×15 ml), followed by drying over anhydrous sodium sulfate. (4-(2-(Dimethylamino)-4-nitrophenyl)piperazin-1-yl)(phenyl)methanone (0.3 g, 69%) was obtained by flash column chromatograph (50% ethyl acetate in hexanes). $^1$H NMR (500 MHz, CDCl$_3$) δ (ppm) 2.88 (s, 6H), 3.30 (s, br, 4H), 3.68 (s, br, 2H), 4.00 (s, br, 2H), 6.90 (d, J=8.8 Hz, 1H), 7.47-7.50 (m, 5H), 7.82 (d, J=2.6 Hz, 1H), 7.87 (dd, J=8.8, 2.6 Hz, 1H). $^{13}$C NMR (125 MHz, CDCl$_3$): δ (ppm) 41.8, 49.2, 114.5, 118.1, 118.6, 127.6, 129.1, 130.4, 136.0, 143.4, 145.6, 149.5, 170.9.

SCHEME 5: Examples 26-31

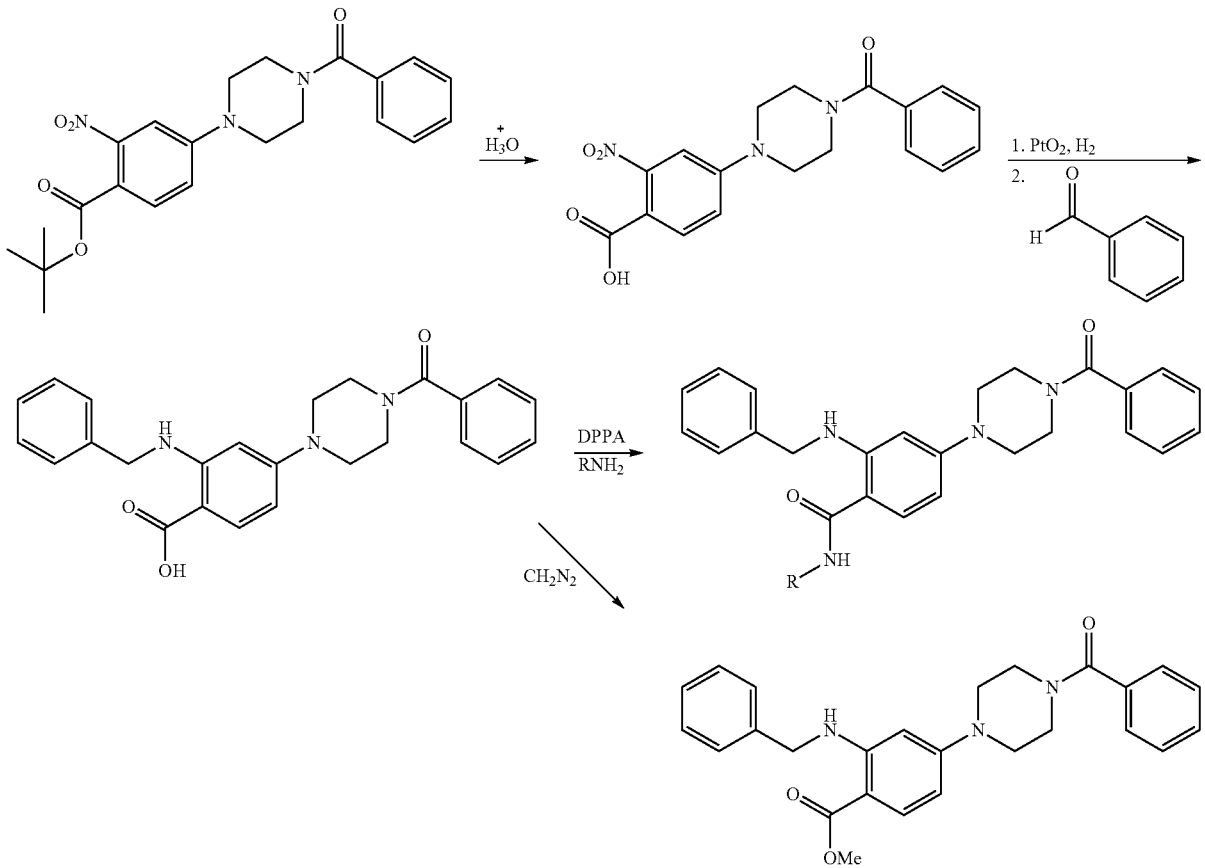

Example 26

2-(benzylamino)-N-methyl-4-(4-benzoylpiperazin-1-yl)benzamide

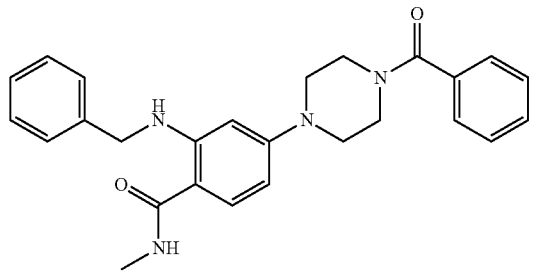 [SMILES: CNC(=O)c1ccc(N2CCN(C(=O)c3ccccc3)CC2)cc1NCc1ccccc1]

A solution of tert-butyl 4-(4-benzoylpiperazin-1-yl)-2-nitrobenzoate (0.5 g, 1.2 mmol), 2.0 ml anisol and 30 ml 4 M hydrochloric acid solution was refluxed for 16 hours, followed by evaporation of all the solvents by high vacuum. $^1$H NMR (500 MHz, DMSO-$d_6$) δ (ppm) 3.48 (d, br, 8H), 7.15 (dd, J=8.9, 2.5 Hz, 1H), 7.31 (d, J=2.5 Hz, 1H), 7.48 (m, 5H), 7.75 (d, J=8.9 Hz, 1H), 13.2 (s, 1H).

The obtained 4-(4-benzoylpiperazin-1-yl)-2-nitrobenzoic acid (0.40 g, 93%) was dissolved in 30 ml ethanol and 10 ml THF, followed by the addition of platinum oxide (20 mg, 5%) and stirred under hydrogen gas for 16 hours. The reaction was filtered with the aid of celite. 2-amino-4-(4-bezoylpiperazin-1-yl)benzoic acid (0.24 g, 70%) was obtained after removing of solvents. To a solution of 2-amino-4-(4-bezoylpiperazin-1-yl)benzoic acid (0.2 g, 0.6 mmol) and benzaldehyde (0.14 ml, 1.3 mmol) added sodium triacetoxyborohydride (0.4 g, 1.8 mmol) and stirred under argon atmosphere overnight. The reaction was quenched with 10 ml water and extracted with ethyl acetate (3×20 ml), followed by drying it over anhydrous sodium sulfate. 2-(benzylamino)-4-(4-benzoylpiperazin-1-yl)benzoic acid (0.11 g, 40%) was obtained after concentration. $^1$H NMR (500 MHz, CDCl$_3$) δ (ppm) 3.25-3.88 (m, br, 8H), 4.48 (s, 2H), 6.20 (d, J=2.3 Hz, 1H), 6.22 (dd, J=2.3, 9.1 Hz, 1H), 7.30-7.45 (m, 10H), 7.48 (d, J=9.1 Hz, 1H), 8.25 (s, 1H), 10.65 (s, 1H).

A solution of 2-(benzylamino)-4-(4-benzoylpiperazin-1-yl)benzoic acid (80 mg, 0.2 mmol), 2 M methylamine THF solution (0.96 ml, 1.9 mmol), triethylamine (0.08 ml, 0.57 mmol) and diphenylphosphoryl azide (0.045 ml, 0.2 mmol) in 15 ml THF was stirred for 16 hours. The run was quenched with 1 ml water and all the solvents were evaporated under vacuum. 2-(benzylamino)-N-methyl-4-(4-benzoylpiperazin-1-yl)benzamide (30 mg, 36%) was obtained by flash column chromatograph (60% ethyl acetate in hexanes). $^1$H NMR (500 MHz, CDCl$_3$) δ (ppm) 2.97 (d, 3H), 3.14-3.25 (d, br, 4H), 3.65 (s, br, 2H), 3.72 (s, br, 2H), 4.42 (d, 2H), 6.01 (d, J=2.3 Hz, 2H), 6.15 (dd, J=2.3, 8.7 Hz, 1H), 7.26-7.49 (m, 10H), 8.52 (s, 1H). $^{13}$C NMR (125 MHz, CDCl$_3$): δ (ppm) 26.9, 47.8, 48.9, 98.3, 103.4, 107.5, 127.5, 127.6, 129.0, 129.1 130.4, 136.0, 139.7, 151.6, 154.3, 170.6, 170.9.

Example 27

2-(benzylamino)-N,N-dimethyl-4-(4-benzoylpiperazin-1-yl)benzamide

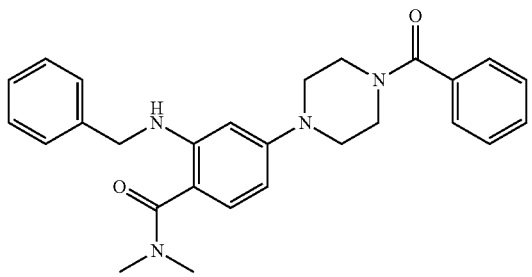 [SMILES: CN(C)C(=O)c1ccc(N2CCN(C(=O)c3ccccc3)CC2)cc1NCc1ccccc1]

A solution of 2-(benzylamino)-4-(4-benzoylpiperazin-1-yl)benzoic acid (80 mg, 0.2 mmol), 2 M dimethylamine THF solution (0.38 ml, 0.78 mmol), tiethylamine (0.08 ml, 0.57 mmol) and diphenylphosphoryl azide (0.045 ml, 0.2 mmol) in 15 ml THF was stirred for 16 hours. The run was quenched with 1 ml water and all the solvents were evaporated under vacuum. 2-(benzylamino)-N,N-dimethyl-4-(4-benzoylpiperazin-1-yl)benzamide (50 mg, 60%) was obtained by flash column chromatograph (60% ethyl acetate in hexanes). $^1$H NMR (500 MHz, DMSO-$d_6$) δ (ppm) 2.95 (d, 6H), 3.15-3.20 (s, br, 4H), 3.62 (s, br, 2H), 3.70 (s, br, 2H), 4.38 (d, 2H), 6.22 (d, J=2.2 Hz, 1H), 6.24 (dd, J=2.2, 8.3 Hz, 1H), 7.00 (dd, J=2.5, 8.4 Hz, 1H), 7.32-7.48 (m, 10H), 8.82 (s, 1H). $^{13}$C NMR (125 MHz, CDCl$_3$): δ (ppm) 30.1, 30.8, 48.1, 48.9, 49.4, 99.5, 103.7, 111.1, 120.7, 126.6, 127.6, 127.7, 129.0, 129.1, 130.3, 130.5, 130.6, 136.0, 139.6, 149.5, 153.4, 170.8, 172.3.

Example 28

2-(benzylamino)-4-(4-bezoylpiperazin-1-yl)benzamide

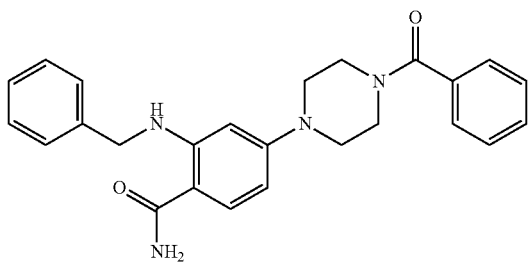 [SMILES: NC(=O)c1ccc(N2CCN(C(=O)c3ccccc3)CC2)cc1NCc1ccccc1]

A solution of 2-(benzylamino)-4-(4-benzoylpiperazin-1-yl)benzoic acid (80 mg, 0.2 mmol), 2 M ammonia ethanol solution (0.60 ml, 1.2 mmol), tiethylamine (0.08 ml, 0.57 mmol) and diphenylphosphoryl azide (0.045 ml, 0.2 mmol) in 15 ml THF was stirred for 16 hours. The run was quenched with 1 ml water and all the solvents were evaporated under vacuum. 2-(benzylamino)-4-(4-bezoylpiperazin-1-yl)benzamide (40 mg, 40%) was obtained by flash column chromatograph (60% ethyl acetate in hexanes), and its hydrochloride was made by bubbling HCL gas in ether solution. $^1$H NMR (500 MHz, DMSO-d$_6$) δ (ppm) 3.28-3.670 (br, 8H), 4.43 (s, 2H), 5.00 (s, 1H), 6.06 (s, 1H), 6.24 (d, J=8.2 Hz, 1H), 7.00 (s, 1H), 7.12-7.65 (m, 13H), 7.67 (d, J=8.8 Hz, 1H). $^{13}$C NMR (125 MHz, DMSO-d$_6$): δ (ppm) 43.5, 46.0, 95.3, 102.7, 127.0, 127.3, 128.3, 128.4, 128.5, 128.6, 129.6, 132.4, 136.0, 139.3, 151.7, 154.2, 167.0, 168.9.

Example 29

2-(benzylamino)-N-ethyl-4-(4-benzoylpiperazin-1-yl)benzamide

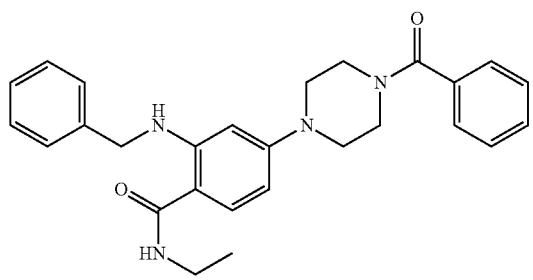 [SMILES: CCNC(=O)c1ccc(N2CCN(C(=O)c3ccccc3)CC2)cc1NCc1ccccc1]

A solution of 2-(benzylamino)-4-(4-benzoylpiperazin-1-yl)benzoic acid (50 mg, 0.12 mmol), ethylamine hydrochloride (36 mg, 0.36 mmol), DIPEA (0.20 ml, 1.2 mmol) and diphenylphosphoryl azide (0.026 ml, 0.12 mmol) in 15 ml THF was stirred for 16 hours. The run was quenched with 1 ml water and all the solvents were evaporated under vacuum. 2-(benzylamino)-N-ethyl-4-(4-benzoylpiperazin-1-yl)benzamide (15 mg, 33%) was obtained by flash column chromatograph (60% ethyl acetate in hexanes), and its hydrochloride was made by bubbling HCL gas in ether solution. $^1$H NMR (500 MHz, DMSO-d$_6$) δ (ppm) 1.10 (t, J=7.2 Hz, 3H), 3.19-3.47 (m, br, 10H), 4.40 (s, 2H), 6.43 (t, J=8.3 Hz, 2H), 7.27-7.59 (m, 13H), 8.26 (s, 1H). $^{13}$C NMR (125 MHz, DMSO-d$_6$): δ (ppm) 14.8, 33.6, 47.5, 127.0, 127.2, 127.8, 128.4, 128.5, 129.4, 129.6, 135.7, 168.3, 169.0.

Example 30 methyl 2-(benzylamino)-4-(4-benzoylpiperazin-1-yl)benzoate

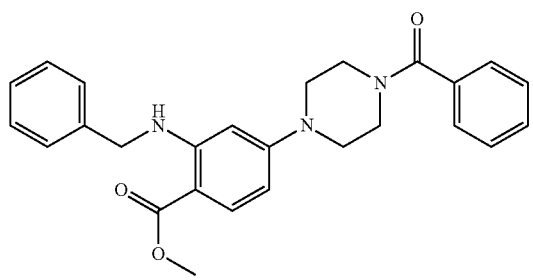 [SMILES: COC(=O)c1ccc(N2CCN(C(=O)c3ccccc3)CC2)cc1NCc1ccccc1]

A solution of 2-(benzylamino)-4-(4-benzoylpiperazin-1-yl)benzoic acid (100 mg, 0.24 mmol) in 15 ml DCM was cooled to 0° C. under argon atmosphere, followed by the addition of triethylsilyldiazomethane (0.12 ml, 0.24 mmol). The run was quenched with 1 ml water and all the solvents were evaporated under vacuum. Methyl 2-(benzylamino)-4-(4-benzoylpiperazin-1-yl)benzoate (30 mg, 30%) was obtained by flash column chromatograph (50% ethyl acetate in hexanes), and its hydrochloride was made by bubbling HCL gas in ether solution. $^1$H NMR (500 MHz, DMSO-d$_6$) δ (ppm) 3.31-3.68 (m, br, 11H), 4.42 (s, 2H), 6.06 (d, J=1.8 Hz, 1H), 6.25 (dd, J=1.8, 9.1 Hz, 1H), 7.26-7.48 (m, 10H), 7.64 (d, J=9.1 Hz, 1H), 8.06 (s, 3H). $^{13}$C NMR (125 MHz, DMSO-d$_6$): δ (ppm) 46.1, 51.0, 95.3, 100.4, 102.8, 127.0, 127.4, 128.4, 128.5, 129.6, 132.4, 135.7, 139.3, 151.7, 154.6, 167.8, 169.1.

Example 31

2-(benzylamino)-N,N-diethyl-4-(4-benzoylpiperazin-1-yl)benzamide

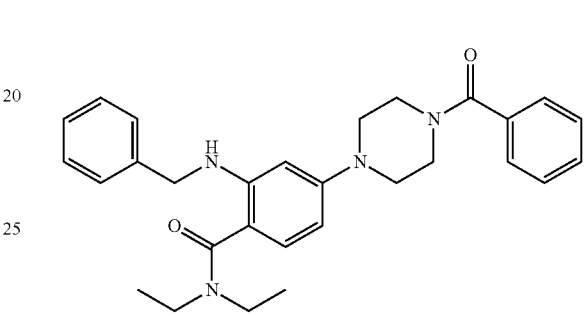

A solution of 2-(benzylamino)-4-(4-benzoylpiperazin-1-yl)benzoic acid (80 mg, 0.2 mmol), diethylamine (0.10 ml, 1.0 mmol), triethylamine (0.13 ml, 1.0 mmol) and diphenylphosphoryl azide (0.045 ml, 0.2 mmol) in 15 ml THF was stirred for 16 hours. The run was quenched with 1 ml water and all the solvents were evaporated under vacuum. 2-(benzylamino)-N,N-diethyl-4-(4-benzoylpiperazin-1-yl)benzamide (20 mg, 22%) was obtained by flash column chromatograph (50% ethyl acetate in hexanes), and its hydrochloride was made by bubbling HCL gas in ether solution. $^1$H NMR (500 MHz, MeOD) δ (ppm) 1.23 (t, J=6.8 Hz, 6H), 3.50-4.02 (s, br, 12H), 4.63 (s, 2H), 7.38-7.54 (m, 13H).

SCHEME 6: Examples 32-33

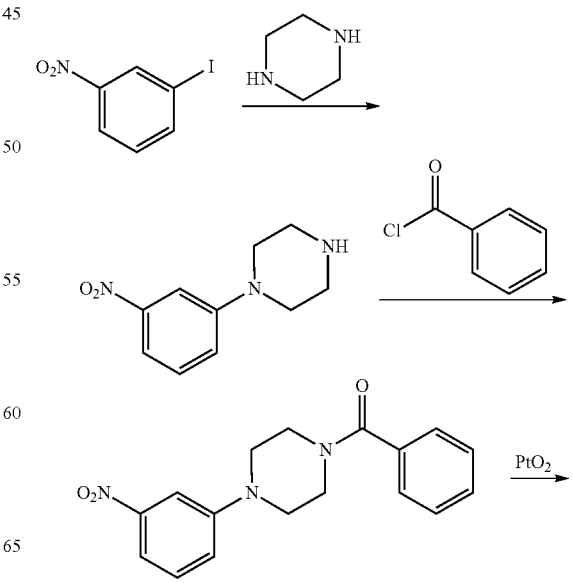

-continued

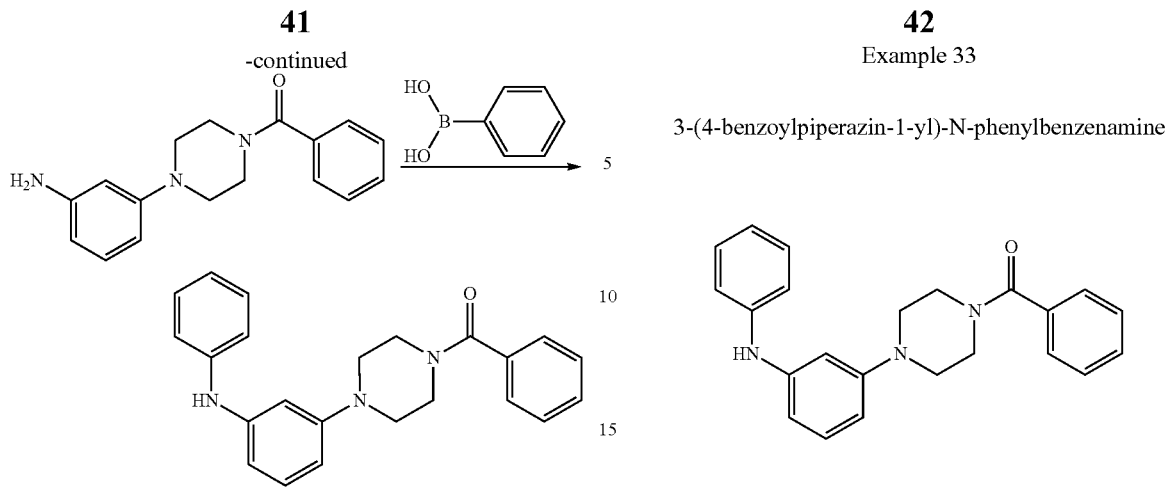

The following exemplary compounds were prepared using this scheme:

Example 32

(4-(3-aminophenyl)piperazin-1-yl)(phenyl)methanone

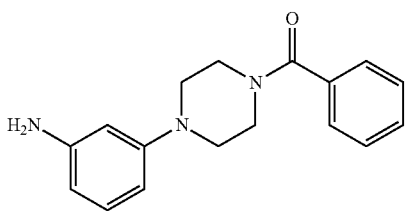

A solution of 3-iodo-nitrobenzene (3.0 g, 12.0 mmol), piperazine (1.6 g, 18.1 mmol), copper (I) iodide (0.23 ml, 1.2 mmol) and potassium carbonate (3.3 g, 24.1 mmol) in 40 ml DMSO was stirred at 45° C. for 16 hours. The run was quenched with 10 ml water and extracted with ethyl acetate (3×30 ml). The extraction was washed with water (2×30 ml) and dried over anhydrous sodium sulfate. 1-(3-Nitrophenyl) piperazine hydrochloride (2.0 g, 80%) was obtained when bubbling the HCl gas in ether solution. A solution of 1-(3-nitrophenyl)piperazine (1.50 g, 7.2 mmol), benzoyl chloride, and triethylamine (5.0 ml, 36.1 mmol) was stirred at 0° C. for 2 hours. The mixture was washed with water (2×30 ml) and dried over anhydrous sodium sulfate. (4-(3-Nitrophenyl)piperazin-1-yl)(phenyl)methanone (1.2 g, 73%) was obtained by flash column chromatograph (50% ethyl acetate in hexanes). The obtained (4-(3-nitrophenyl)piperazin-1-yl)(phenyl) methanone (1.2 g, 3.8 mmol) was dissolved in 30 ml ethanol and 10 ml THF, followed by the addition of platinum oxide (0.12 mg, 10%) and stirred under hydrogen gas for 16 hours. The reaction was filtered with the aid of celite. (4-(3-aminophenyl)piperazin-1-yl)(phenyl)methanone (0.81 g, 80%) was obtained by flash column chromatograph (90% ethyl acetate in hexanes), and its hydrochloride was made by bubbling HCl gas in ether solution. $^1$H NMR (500 MHz, DMSO-$d_6$) δ (ppm) 3.25 (s, br, 4H), 3.53 (d, br, 4H), 6.83 (dd, J=1.2, 7.7 Hz, 1H), 6.99 (s, 1H), 7.04 (d, J=8.4 Hz, 1H), 7.34 (t, J=8.2 Hz, 1H), 7.44-7.48 (m, 5H), 10.35 (s, br, 2H). $^{13}$C NMR (125 MHz, DMSO-$d_6$): δ (ppm) 42.4, 48.1, 110.0, 112.8, 115.1, 120.2, 127.1, 127.2, 128.4, 129.6, 129.9, 130.2, 135.7, 151.0, 169.1.

Example 33

3-(4-benzoylpiperazin-1-yl)-N-phenylbenzenamine

A suspension of (4-(3-aminophenyl)piperazin-1-yl)(phenyl)methanone (0.5 g, 1.8 mmol), copper acetate (0.65 g, 3.6 mmol), triethylamine (1.7 ml, 12.4 mmol), 4 Å molecular sieves (0.5 g) and phenylboronic acid and pyridine complex (0.70 g, 1.8 mmol) in 30 ml dry dichloromethane was stirred at room temperature overnight. The reaction was quenched with 20 ml water extracted with dichloromethane (3×40 ml), followed by drying over anhydrous sodium sulfate. 3-(4-Benzoylpiperazin-1-yl)-N-phenylbenzenamine (0.42 g, 66%) was obtained by flash column chromatograph (50% ethyl acetate in hexanes). $^1$H NMR (500 MHz, CDCl$_3$) δ (ppm) 3.20 (d, br, 4H), 3.65 (d, br, 4H), 5.73 (s, 1H), 6.54 (dd, J=8.0, 1.6 Hz, 1H), 6.67 (m, 2H), 6.97 (t, J=7.4 Hz, 1H), 7.11 (dd, J=8.6, 1.0 Hz, 2H), 7.28 (t, J=8.0 Hz, 1H), 7.44 (m, 2H), 7.48 (m, 5H). $^{13}$C NMR (125 MHz, CDCl$_3$): δ (ppm) 50.0, 50.1, 50.3, 106.5, 110.0, 110.7, 118.6, 121.6, 127.6, 129.0, 129.8, 130.3, 130.5, 136.1, 143.5, 144.7, 152.6, 170.9.

SCHEME 7: Examples 34-44

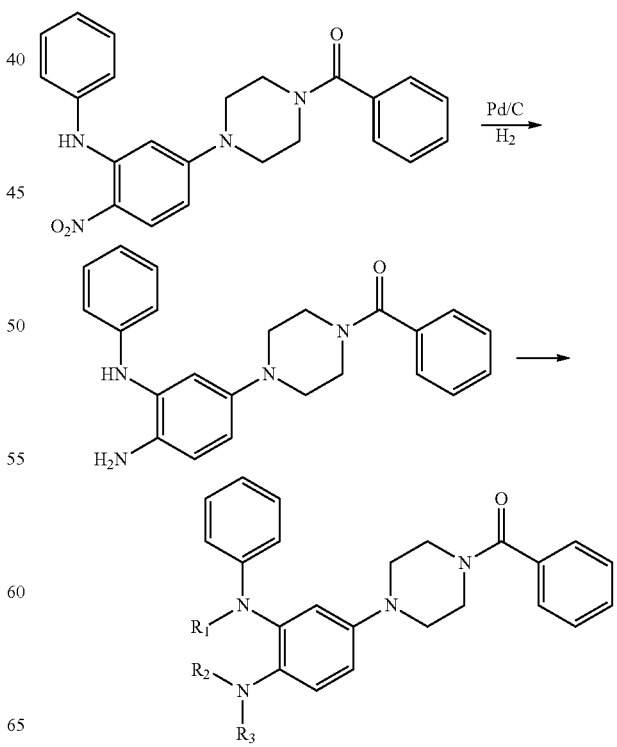

The following exemplary compounds were prepared using this scheme:

Example 34

(4-(4-(dimethylamino)-3-(phenylamino)phenyl)piperazin-1-yl)(phenyl)methanone

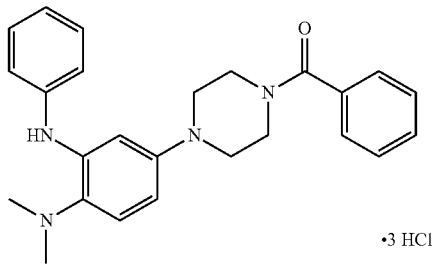 [SMILES: CN(C)c1ccc(N2CCN(C(=O)c3ccccc3)CC2)cc1Nc1ccccc1]

·3 HCl

To a stirred solution of (4-(3-(benzyl(phenyl)amino)-4-(dimethylamino)phenyl)piperazin-1-yl)(phenyl)methanone (0.49 g, 1 mmol) in ethanol (10 ml), 10% Pd—C was added under argon. The resulting mixture was stirred under $H_2$ atmosphere at room temperature for 10 h. After completion of reaction (by TLC) it was filtered through celite, evaporated under vacuum to get the crude product. Flash chromatography gave (4-(4-(dimethylamino)-3-(phenylamino)phenyl) piperazin-1-yl)(phenyl)methanone which was isolated finally as trihydrochloride salt (0.39 g), 86% yield. $^1$H NMR (500 MHz, DMSO): δ 3.26 (s, 6H), 3.4 (bs, 4H), 4.2 (bs, 2H), 4.4 (s, 2H), 7.15 (t, J=7, 7.5 Hz 2H), 7.26 (d, J=7.6 Hz 2H), 7.29 (s, 2H), 7.42 (t, J=7.5, 8 Hz, 2H), 7.51 (m, 7H).

HRMS (ESI) calculated for $C_{25}H_{29}N_4O$: 401.2336, Found: 401.2346.

Example 35

(4-(4-amino-3-(phenylamino)phenyl)piperazin-1-yl)(phenyl)methanone

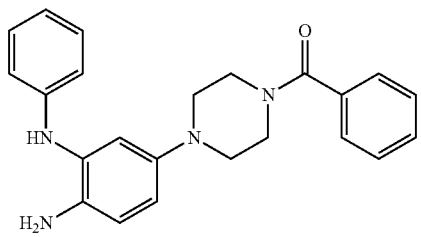

A suspension of 5-(4-benzoylpiperazin-1-yl)-2-nitro-N-phenylbenzenamine (0.8 g, 2.0 mmol), and palladium on carbon (40 mg, 5%) in 40 ml ethanol was stirred at room temperature under hydrogen atmosphere overnight. The mixture was filtered with the aid of celite. (4-(4-amino-3-(phenylamino)phenyl)piperazin-1-yl)(phenyl)methanone (0.60 g, 80%) was obtained by flash column chromatograph (60% ethyl acetate in hexanes), ant its hydrochloride was made by bubbling HCl gas in ether solution. $^1$H NMR (500 MHz, DMSO-$d_6$) δ (ppm) 3.24 (s, br, 4H), 3.53 (s, br, 2H), 3.80 (s, br, 2H), 6.81 (d, J=8.1 Hz, 1H), 6.87 (t, J=7.3 Hz, 1H), 7.26-7.49 (m, 11H), 8.56 (s, br, 1H). $^{13}$C NMR (125 MHz, DMSO-$d_6$): δ (ppm) 49.4, 107.5, 110.4, 116.6, 120.1, 124.9, 127.0, 128.4, 129.3, 129.6, 135.5, 137.6, 143.1, 169.0.

Example 36

N-(4(4-benzoylpiperazin-1-yl)-2-(phenylamino)phenyl) acetamide

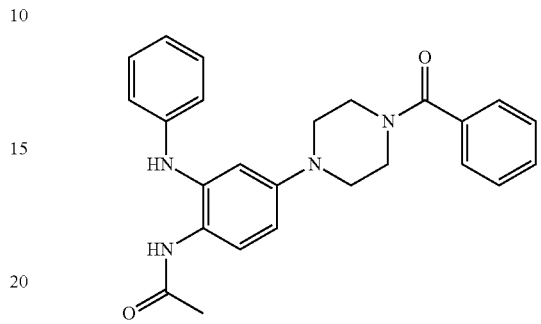

A solution of (4-(4-amino-3-(phenylamino)phenyl)piperazin-1-yl)(phenyl)methanone (0.7 g, 1.9 mmol), acetyl chloride (0.13 ml, 1.9 mmol) and potassium carbonate (0.31 g, 2.3 mmol) in 20 ml THF was stirred at 0° C. for 2 hours. The mixture was washed with water (2×10 ml) and dried over anhydrous sodium sulfate before removing the solvents. N-(4-(4-benzoylpiperazin-1-yl)-2-(phenylamino)phenyl)acetamide (0.40 g, 51%) was obtained after flash column chromatograph (ethyl acetate). $^1$H NMR (500 MHz, CDCl$_3$) δ (ppm) 2.15 (s, 3H), 3.03-3.95 (m, 8H), 5.93 (s, 1H), 6.66 (dd, J=2.6, 8.8 Hz, 1H), 6.92 (m, 4H), 7.26 (m, 2H), 7.44 (s, 1H), 7.46 (m, 5H), 7.53 (d, J=8.8 Hz, 1H). $^{13}$C NMR (125 MHz, CDCl$_3$): δ (ppm) 24.5, 50.2, 110.8, 112.6, 117.3, 121.0, 123.9, 125.3, 127.6, 129.0, 129.9, 130.0, 130.1, 130.3, 136.0, 137.0, 144.6, 150.0, 169.6, 170.9.

Example 37

(4-(3-(N-benzyl-N-phenylamino)-4-aminophenyl) piperazin-1-yl)(phenyl)methanone

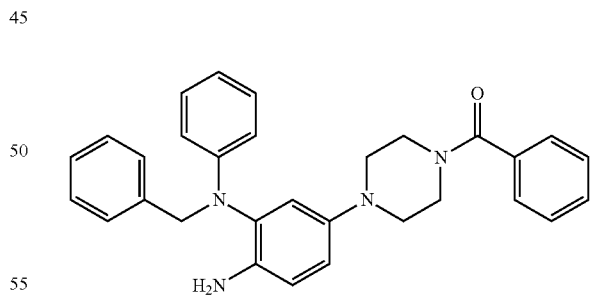

A suspension of 5-(4-benzoylpiperazin-1-yl)-2-nitro-N-phenylbenzenamine (1.0 g, 2.5 mmol), benzylbromide (0.3 ml, 2.5 mmol), potassium hydroxide (0.18 g, 3.2 mmol) and tetra-butyl ammonium iodide (0.05 g, 0.25 mmol) in 40 ml toluene was stirred at room temperature overnight. The red solids were filtered to get N-benzyl-5-(4-benzoylpiperazin-1-yl)-2-nitro-N-phenylbenzenamine (1.1 g, 90%). $^1$H NMR (500 MHz, DMSO-$d_6$) δ (ppm) 3.40-3.58 (m, br, 8H), 4.94 (s, 2H), 6.30 (d, J=8.0 Hz, 2H), 6.73 (t, J=7.2 Hz, 1H), 6.88 (d, J=9.2 Hz, 2H), 7.09-7.48 (m, 12H), 7.98 (d, J=8.9 Hz, 1H).

A suspension of N-benzyl-5-(4-benzoylpiperazin-1-yl)-2-nitro-N-phenylbenzenamine (1.2 g, 2.4 mmol), 2 M copper sulfate solution (10 ml, 2.0 mmol), and sodium borohydride (0.46 g, 12.2 mmol) in 40 ml ethanol was stirred at room temperature overnight. The run was quenched with additional 20 ml water, and it was extracted with acetyl acetate (3×20 ml). (4-(3-(N-benzyl-N-phenylamino)-4-aminophenyl)piperazin-1-yl)(phenyl)methanone (0.8 g, 71%) was obtained by flash column chromatograph (50% ethyl acetate in hexanes). $^1$H NMR (500 MHz, CDCl$_3$) δ (ppm) 3.29 (d, br, 4H), 3.56 (s, br, 4H), 3.93 (s, 2H), 4.88 (s, 2H), 6.68 (d, J=7.9 Hz, 2H), 6.80 (m, 4H), 7.19 (dd, J=7.4, 8.7 Hz, 2H), 7.25-7.45 (m, 5H), 7.47 (s, 5H). $^{13}$C NMR (125 MHz, CDCl$_3$): δ (ppm) 51.6, 51.8, 51.9, 56.1, 114.2, 117.8, 118.1, 118.4, 119.5, 127.4, 127.5, 127.6, 128.9, 129.0, 129.7, 130.0, 133.9, 136.2, 138.8, 139.5, 145.1, 148.2, 170.8.

Example 38

(4-(3-(N-methyl-N-phenylamino)-4-(dimethylamino)phenyl)piperazin-1-yl)(phenyl)methanone

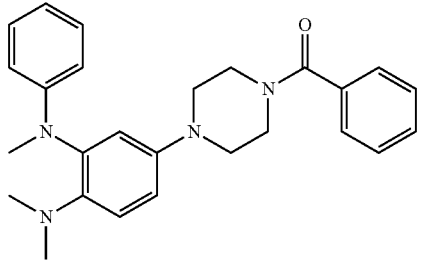 [SMILES: CN(C)c1ccc(N2CCN(C(=O)c3ccccc3)CC2)cc1N(C)c1ccccc1]

A suspension of 5-(4-benzoylpiperazin-1-yl)-N-1-phenylbenzene-1,2-diamine (0.2 g, 0.5 mmol), 20 ml formaldehyde ether solution extracted from 30 ml formaldehyde water, and sodium t-butoxide (0.20 g, 1.1 mmol) in 20 ml 1,2-dichloroethane was stirred at room temperature for 6 hours. Sodium triacetoxyborohydride (0.45 g, 2.2 mmol) was added and stirred overnight before quenching with 10 ml water. The mixture was extracted with ethyl acetate (3×20 ml) and dried over anhydrous sodium sulfate. (4-(3-(N-methyl-N-phenylamino)-4-(dimethylamino)phenyl)piperazin-1-yl)(phenyl)methanone (0.1 g, 50%) was obtained by flash column chromatograph (50% ethyl acetate in hexanes). $^1$H NMR (500 MHz, CDCl$_3$) δ (ppm) 2.71 (s, 6H), 3.00 (s, br, 2H), 3.15 (s, br, 2H), 3.21 (s, 3H), 3.56 (s, br, 2H), 3.93 (s, br, 2H), 6.75-6.81 (m, 5H), 7.00 (d, J=9.5 Hz, 1H), 7.22 (m, 2H), 7.46 (m, 5H). $^{13}$C NMR (125 MHz, CDCl$_3$): δ (ppm) 37.8, 43.2, 51.2, 140.7, 114.0, 115.4, 117.5, 119.0, 119.6, 127.6, 129.0, 129.3, 130.2, 136.1, 144.1, 146.5, 149.0, 170.8.

Example 39

(4-(4-(dimethylamino)-3-(phenylamino)phenyl)piperazin-1-yl)(phenyl)methanone

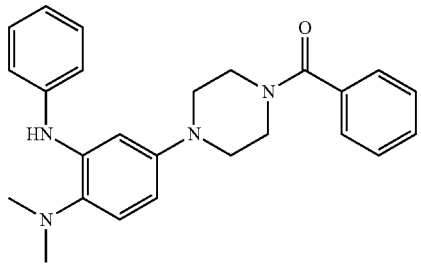 [SMILES: CN(C)c1ccc(N2CCN(C(=O)c3ccccc3)CC2)cc1Nc1ccccc1]

A suspension of 5-(4-benzoylpiperazin-1-yl)-N-1-phenylbenzene-1,2-diamine (0.2 g, 0.5 mmol), paraformaldehyde (0.2 g, 66.7 mmol), and triethylamine (0.2 ml) in 20 ml of 1,2-dichloroethane was stirred at room temperature for 6 hours. Sodium triacetoxyborohydride (0.45 g, 2.2 mmol) was added and stirred overnight before quenching with 10 ml water. The mixture was extracted with ethyl acetate (3×20 ml) and dried over anhydrous sodium sulfate. (4-(4-(dimethylamino)-3-(phenylamino)phenyl)piperazin-1-yl)(phenyl)methanone (0.04 g, 19%) was obtained by flash column chromatograph (50% ethyl acetate in hexanes). $^1$H NMR (500 MHz, CDCl$_3$) δ (ppm) 2.67 (s, 6H), 3.10 (d, br, 4H), 3.59 (s, br, 2H), 3.94 (s, br, 2H), 6.45 (dd, J=8.6, 2.7 Hz, 1H), 6.74 (s, 1H), 6.99 (m, 2H), 7.08 (d, J=8.6 Hz, 1H), 7.21 (d, J=8.5 Hz, 2H), 7.36 (m, 2H), 7.46 (s, 5H). $^{13}$C NMR (125 MHz, CDCl$_3$): δ (ppm) 45.0, 50.8, 51.0, 103.9, 108.5, 119.1, 120.9, 121.5, 127.6, 129.0, 129.9, 130.2, 136.2, 136.6, 139.4, 143.3, 148.6, 170.8.

Example 40

(4-(3-(N-methyl-N-phenylamino)-4-aminophenyl)piperazin-1-yl)(phenyl)methanone

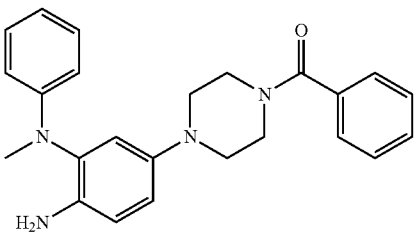

A suspension of N-methyl-5-(4-benzoylpiperazin-1-yl)-2-nitro-N-phenylbenzenamine (0.5 g, 1.2 mmol), and platinum oxide (25 mg, 5%) in 20 ml ethanol was stirred at room temperature under hydrogen atmosphere overnight. The mixture was filtered with the aid of celite. (4-(3-(N-methyl-N-phenylamino)-4-aminophenyl)piperazin-1-yl)(phenyl)methanone (0.42 g, 90%) was obtained by flash column chromatograph (60% ethyl acetate in hexanes). $^1$H NMR (500 MHz, CDCl$_3$) δ (ppm) 2.98 (d, br, 4H), 3.24 (s, 3H), 3.58 (s, br, 2H), 3.63 (s, br, 2H), 3.94 (s, br, 2H), 6.68 (d, J=7.9 Hz, 2H), 6.73 (d, J=2.2 Hz, 1H), 6.82 (m, 3H), 7.23 (m, 2H), 7.45 (s, 5H). $^{13}$C NMR (125 MHz, CDCl$_3$): δ (ppm) 39.1, 51.8, 113.9, 117.4, 117.8, 118.1, 118.2, 129.0, 129.6, 127.6, 130.2, 135.3, 136.2, 138.8, 145.2, 149.2, 170.8.

Example 41

(4-(3-(N-methyl-N-phenylamino)-4-(methylamino)phenyl)piperazin-1-yl)(phenyl)methanone

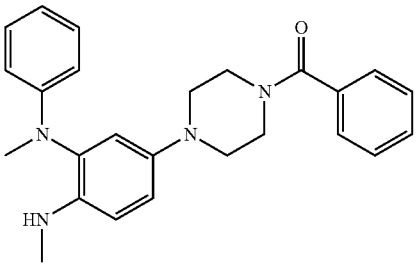 [SMILES: CNc1ccc(N2CCN(C(=O)c3ccccc3)CC2)cc1N(C)c1ccccc1]

A suspension of 5-(4-benzoylpiperazin-1-yl)-N-1-phenyl-benzene-1,2-diamine (0.2 g, 0.5 mmol), paraformaldehyde (0.023 g, 0.78 mmol), and 5 drops of acetic acid in 20 ml 1,2-dichloroethane was stirred at room temperature for 5 hours. Sodium triacetoxyborohydride (0.55 g, 2.6 mmol) was added and stirred overnight before quenching with 10 ml water. The mixture was extracted with ethyl acetate (3×20 ml) and dried over anhydrous sodium sulfate. (4-(3-(N-methyl-N-phenylamino)-4-(methylamino)phenyl)piperazin-1-yl)(phenyl)methanone (0.13 g, 63%) was obtained by flash column chromatograph (45% ethyl acetate in hexanes). $^1$H NMR (500 MHz, DMSO-d$_6$) δ (ppm) 2.76 (s, 3H), 3.16 (s, 3H), 3.40 (s, br, 4H), 3.69 (s, br, 4H), 6.57 (d, J=8.1 Hz, 2H), 6.72 (t, J=7.2 Hz, 1H), 7.20 (m, 3H), 7.50 (m, 7H). $^{13}$C NMR (125 MHz, DMSO-d$_6$): δ (ppm) 15.2, 39.1, 64.9, 113.6, 114.5, 117.6, 127.0, 127.1, 128.9, 128.6, 126.0, 129.7, 129.8, 135.2, 148.9, 169.1.

Example 42

(4-(4-(methylamino)-3-(phenylamino)phenyl)piper-azin-1-yl)(phenyl)methanone

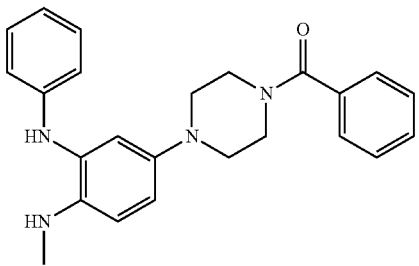 [SMILES: CNc1ccc(N2CCN(C(=O)c3ccccc3)CC2)cc1Nc1ccccc1]

A suspension of 5-(4-benzoylpiperazin-1-yl)-N1-phenyl-benzene-1,2-diamine (0.2 g, 0.54 mmol), paraformaldehyde (0.025 g, 1.01 mmol), and 6 drops of acetic acid in 10 ml 1,2-dichloroethane was stirred at room temperature for 5 hours. Sodium triacetoxyborohydride (0.45 g, 2.2 mmol) was added and stirred overnight before quenching with 10 ml water. The mixture was extracted with ethyl acetate (3×20 ml) and dried over anhydrous sodium sulfate. ((4-(4-(Methylamino)-3-(phenylamino)phenyl)piperazin-1-yl)(phenyl)methanone (0.021 g, 10%) was obtained by flash column chromatograph (50% ethyl acetate in hexanes). $^1$H NMR (500 MHz, CDCl$_3$) δ (ppm) 2.86 (s, 3H), 2.97 (s, br, 4H), 3.58 (s, br, 2H), 3.94 (s, br, 3H), 5.18 (s, 1H), 6.88 (m, 6H), 7.25 (m, 2H), 7.47 (m, 6H).

Example 43

2-(4-(4-benzoylpiperazin-1-yl)-2-(phenylamino)phenylamino)ethanol

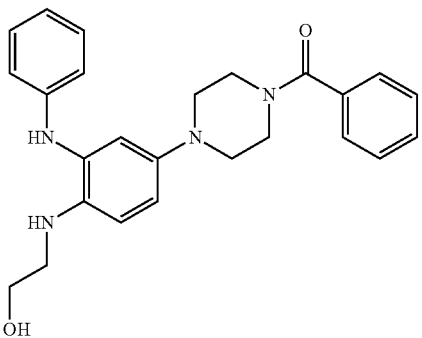 [SMILES: O=C(c1ccccc1)N1CCN(c2ccc(NCCO)c(Nc3ccccc3)c2)CC1]

A suspension of 5-(4-benzoylpiperazin-1-yl)-N-1-phenyl-benzene-1,2-diamine (0.3 g, 0.8 mmol), ethylene carbonate (0.11 g, 1.2 mmol), and potassium hydroxide (4.5 mg, 0.08 mmol) in 15 ml DMF was stirred at 150° C. under argon atmosphere for 16 hours. The run was quenched with 20 ml water and extracted with ethyl acetate (2×20 ml) after cooling to room temperature. The extraction was washed with water (3×20 ml) and dried over anhydrous sodium sulfate. 2-(4-(4-Benzoylpiperazin-1-yl)-2-(phenylamino)phenylamino)ethanol (0.034 g, 10%) was obtained by flash column chromatograph (ethyl acetate). $^1$H NMR (500 MHz, CDCl$_3$) δ (ppm) 3.00 (m, br, 5H), 3.61 (s, br, 2H), 3.96 (s, br, 2H), 4.05 (t, J=4.7 Hz, 2H), 4.12 (t, J=4.7 Hz, 2H), 6.74 (d, J=2.2 Hz, 1H), 6.81 (dd, J=2.2, 8.6 Hz, 1H), 7.09 (d, J=8.6 Hz, 1H), 7.45 (m, 6H), 7.57 (m, 4H). $^{13}$C NMR (125 MHz, CDCl$_3$): δ (ppm) 45.1, 52.4, 62.1, 100.2, 108.9, 112.6, 125.1, 126.6, 127.6, 128.4, 129.0, 130.1, 130.3, 130.8, 134.8, 136.0, 147.8, 154.9, 170.9.

Example 44

4-(4-benzoylpiperazin-1-yl)-N-1-(2-morpholinoet-hyl)-N-2-phenylbenzene-1,2-diamine

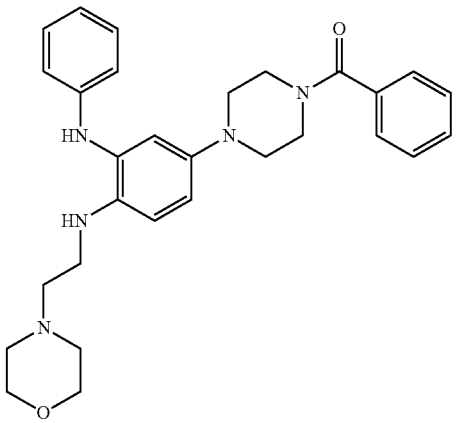 [SMILES: O=C(c1ccccc1)N1CCN(c2ccc(NCCN3CCOCC3)c(Nc3ccccc3)c2)CC1]

A suspension of 5-(4-benzoylpiperazin-1-yl)-N-1-phenyl-benzene-1,2-diamine (0.5 g, 1.3 mmol), 4-(2-chloroethyl)morpholine hydrochloride (0.37 ml, 2.0 mmol), potassium hydroxide (0.23 g, 4.0 mmol) and tetra-butyl ammonium iodide (0.05 g, 0.13 mmol) in 40 ml toluene was refluxed under argon atmosphere overnight. The run was quenched with 20 ml water after cooling to room temperature. The mixture was extracted with acetyl acetate (3×20 ml) and dried over anhydrous sodium sulfate. 4-(4-Benzoylpiperazin-1-yl)-N1-(2-morpholinoethyl)-N2-phenylbenzene-1,2-diamine (0.4 g, 61%) was obtained by flash column chromatograph (10% acetone in ethyl acetate). $^1$H NMR (500 MHz, CDCl$_3$) δ (ppm) 2.50 (s, br, 4H), 2.67 (t, J=6.6 Hz, 2H), 3.00 (d, br, 4H), 3.57 (s, br, 2H), 3.70 (t, J=4.5 Hz, 4H), 3.76 (t, J=6.6 Hz, 2H), 3.91 (s, br, 3H), 6.64 (d, J=8.1 Hz, 2H), 6.71 (d, J=1.5 Hz, 1H), 6.78 (t, J=7.3 Hz, 1H), 6.81 (d, J=8.8 Hz, 2H), 7.20 (dd, J=7.3, 8.5 Hz, 2H), 7.45 (m, 5H). $^{13}$C NMR (125 MHz, CDCl$_3$): δ (ppm) 48.9, 51.8, 51.9, 54.4, 56.7, 67.4, 113.8, 117.5, 118.0, 119.2, 119.5, 127.6, 129.0, 129.7, 130.2, 133.8, 136.1, 139.9, 145.0, 148.1, 170.84.

SCHEME 8: Example 45

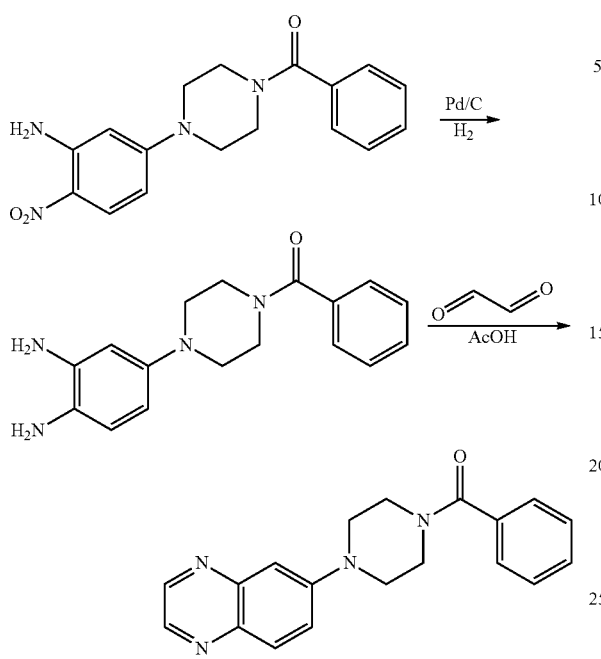

The following exemplary compounds were synthesized using this scheme:

Example 45 phenyl(4-(quinoxalin-6-yl)piperazin-1-yl)methanone

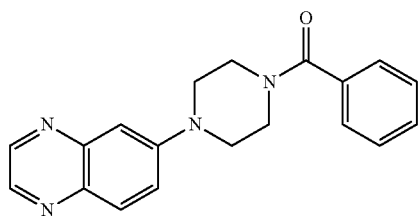 [SMILES: O=C(c1ccccc1)N1CCN(c2ccc3nccnc3c2)CC1]

A suspension of (4-(3-amino-4-nitrophenyl)piperazin-1-yl)(phenyl)methanone (2.0 g, 9.0 mmol), 5 ml acetic acid and palladium on carbon (100 mg, 5%) in 50 ml ethanol was stirred at room temperature under hydrogen atmosphere overnight. The mixture was filtered with the aid of celite. Crude (4-(3,4-diaminophenyl)piperazin-1-yl)(phenyl)methanone (1.2 g, 41%) was obtained after removing of solvents. A suspension of (4-(3,4-diaminophenyl)piperazin-1-yl)(phenyl)methanone (0.2 g, 0.67 mmol), acetic acid (0.23 ml, 4.0 mmol) and 40% oxalaldehyde (0.14 ml, 1.0 mmol) in 40 ml acetonitrile was stirred at 50° C. under argon atmosphere overnight. The reaction was quenched with the 5 ml water and extracted with ethyl acetate (3×40 ml). The extraction was concentrated after drying over anhydrous sodium sulfate. Phenyl(4-(quinoxalin-6-yl)piperazin-1-yl)methanone (0.060 g, 28%) was obtained by flash column chromatograph (10% acetone in ethyl acetate). $^1$H NMR (500 MHz, CDCl$_3$) δ (ppm) 3.37 (d, br, 4H), 3.69 (s, br, 2H), 4.01 (s, br, 2H), 7.30 (d, J=2.7 Hz, 1H), 7.48 (m, 5H), 7.50 (dd, J=9.3, 2.7 Hz, 1H), 7.56 (d, J=9.3 Hz, 1H), 8.65 (d, J=1.9 Hz, 1H), 8.73 (d, J=1.9 Hz, 1H). $^{13}$C NMR (125 MHz, CDCl$_3$): δ (ppm) 49.1, 49.3, 110.8, 123.0, 127.6, 29.0, 130.4, 130.5, 1135.7, 139.0, 142.6, 144.9, 151.9, 145.6, 170.9.

SCHEME 9: Examples 46-56

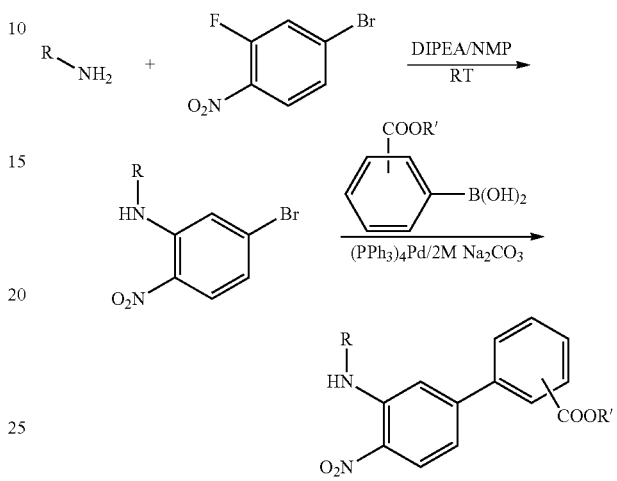

The following exemplary compounds were synthesized using this scheme:

Example 46

4'-nitro-3'-(phenylamino) biphenyl-3-carboxylic acid

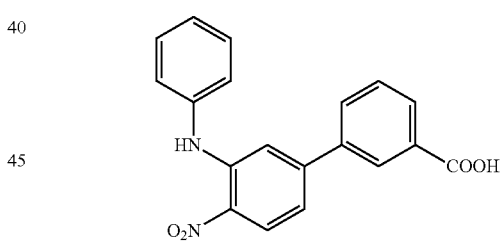

To a solution of N-Phenyl-5-bromo-2-nitrobenzenamine (0.9 g, 3.2 mmol) and 3-carboxyphenylboronic acid (0.64 g, 3.92 mmol) in Toluene: EtOH: H$_2$O (8:8:1) was added K$_2$CO$_3$ (1.4 g, 9.78 mmol). After stirring reaction for 15 min under argon tetrakis (triphenylphosphine) palladium (0.184 mg, 0.016 mol) was added, resulting mixture was then heated at 100° C. for 12 h. The reaction mixture was cooled to room temperature and diluted with ethyl acetate and extracted three times with water. The aqueous layer was then acidified with 2M HCl to get 4'-nitro-3'-(phenylamino) biphenyl-3-carboxylic acid (0.8. g), 84% yield. $^1$H NMR (500 MHz, DMSO): δ 7.23 (m, 2H), 7.44 (m, 4H), 7.61 (t, J=7.7 Hz, 1H), 7.83 (d, J=7.7 Hz, 1H), 8.00 (d, J=7.7 Hz 1H), 8.07 (s, 1H), 8.25 (d, J=9 Hz, 1H), 9.50 (s, 1H), 13.15 (bs, 1H). HRMS (ESI) calculated for C$_{19}$H$_{14}$N$_2$NaO$_4$: 357.0846, Found: 357.0816.

Example 47

4'-amino-3'-(phenylamino) biphenyl-3-carboxylic acid

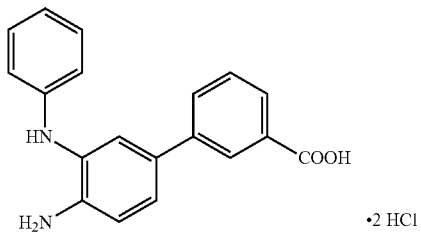 [SMILES: Nc1ccc(-c2cccc(C(=O)O)c2)cc1Nc1ccccc1]

To stirred solution 4'-nitro-3'-(phenylamino) biphenyl-3-carboxylic acid (0.5 g, 1.5 mmol) in methanol (5 mL) $PtO_2.H_2O$ (30 mg, 0.0149 mmol) was added. The resulting mixture was stirred under H2 atmosphere at room temperature for 10 h. After completion of reaction (by TLC) it was filtered through celite, evaporated under vacuum to get the crude product. Flash chromatography gave 4'-amino-3'-(phenylamino) biphenyl-3-carboxylic acid which was isolated finally as dihydrochloride salt (0.4 g) 88% yield. $^1$H NMR (500 MHz, DMSO): δ 6.87 (t, J=7 Hz, 1H), 7.02 (d, J=6.5 Hz, 2H), 7.32 (m, 4H), 7.59 (m, 2H), 7.84 (d, J=7.8 Hz 1H), 7.91 (d, J=7.5 Hz, 1H), 8.09 (s, 1H). HRMS (ESI) calculated for $C_{19}H_{17}N_2O_2$: 305.1285, Found: 305.1279.

Example 48

3'-(benzylamino)-4'-nitrophenyl-2-carboxylic acid

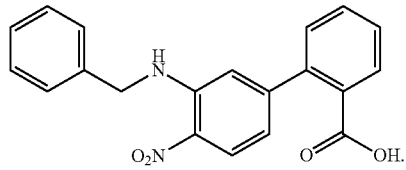

To a solution of N-benzyl-5-bromo-2-nitrobenzenamine (0.5 g, 1.6 mmol) and 2-carbaethoxyphenylboronic acid (0.31 g, 2.4 mmol) in DME (5 mL) was added 2M $Na_2CO_3$ solution (2.5 ml, 4.8 mmol). After stirring reaction for 15 min under argon tetrakis (triphenylphosphine) palladium (0.092 mg, 0.08 mol) was added, resulting mixture was then heated at 80° C. for 20 h. It was then filtered through celite, evaporated under vacuum to get crude product. Flash column chromatography gave ethyl 3'-(benzylamino)-4'-nitrophenyl-2-carboxylate (0.38 g) in 62% yield; it was used for further reaction without purification.

To stirred solution of ethyl 3'-(benzylamino)-4'-nitrophenyl-2-carboxylate (0.4 g, 1.06 mmol) in THF:$H_2O$ (3:1) was added lithium hydroxide (0.235 g, 10.6 mmol) at room temperature. The resulting mixture was stirred for 5 h, solvent was evaporated and residue was dissolved in water washed with dichloromethane. The aqueous layer was then neutralise with 2M HCl to get yellow solid 3'-(benzylamino)-4'-nitrophenyl-2-carboxylic acid (0.33 g), 90% yield. $^1$H NMR (500 MHz, DMSO): δ 4.65 (d, J=6 Hz, 2H), 6.63 (dd, J=1.7 Hz, 1H), 6.89 (d, J=1.5 Hz, 1H), 7.26 (m, 2H), 7.38 (m, 4H), 7.52 (ddd, J=1.2 Hz, 1H), 7.58 (ddd, J=1.4, 1.3, 1H), 7.78 (d, J=1.2, 1.15 Hz, 1H), 8.00 (d, J=8.8 Hz, 1H), 8.7 (t, J=5.6, 5.8 Hz, 1H), 12.95 (bs, 1H). HRMS (ESI) calculated for $C_{20}H_{16}N_2NaO_4$: 371.1002, Found: 371.0986.

Example 49

3' benzylamino)-4'-nitro-N-phenylbiphenyl-2-carboxamide

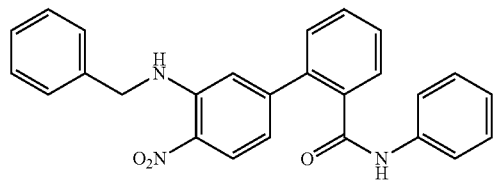 [SMILES: O=C(Nc1ccccc1)c1ccccc1-c1ccc([N+](=O)[O-])c(NCc2ccccc2)c1]

To a solution of 3'-(benzylamino)-4'-nitrophenyl-2-carboxylic acid (0.1 g, 0.28 mmol) and aniline (0.025 mL, 0.28 mmol) in DMF (5 mL) was added diisopropylethylamine (0.07 mL, 0.42 mmol) under argon. The mixture cooled to 0° C., HATU (0.1 gm, 0.28 mmol) was added at that temperature and then stirred at room temperature for 4 h. After completion of reaction (by TLC), $H_2O$ (5 mL) was added drop by drop. The resulting yellow precipitate was filtered, washed with 2 mL of water, dried (high vacuum, 14 h) to furnish 3'-(benzylamino)-4'-nitro-N-phenylbiphenyl-2-carboxamide (0.1 g), 92% yield. $^1$H NMR (500 MHz, DMSO): 4.47 (d, J=5.85 Hz, 2H), 6.76 (dd, J=1.7 Hz, 1H), 6.96 (d, J=1.5 Hz, 1H), 7.10 (t, J=7.4 Hz, 1H), 7.28 (m, 3H), 7.35 (m, 5H), 7.58 (m, 5H), 8.10 (d, J=9 Hz, 1H), 8.60 (t, J=5.9 Hz, 1H), 10.44 (bs, 1H). HRMS (ESI) calculated for $C_{26}H_{21}N_3NaO_3$: 446.1475, Found: 446.1485.

Example 50

N-benzyl-3' benzylamino)-4'-nitrobiphenyl-2-carboxamide

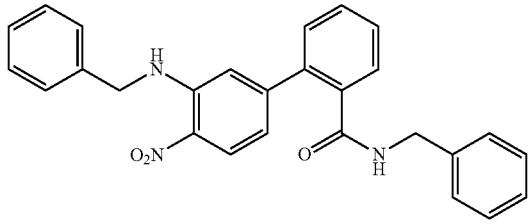 [SMILES: O=C(NCc1ccccc1)c1ccccc1-c1ccc([N+](=O)[O-])c(NCc2ccccc2)c1]

To a solution of 3'-(benzylamino)-4'-nitrophenyl-2-carboxylic acid (0.1 g, 0.28 mmol) and benzylamine (0.030 mL, 0.28 mmol) in DMF (5 mL) was added diisopropylethylamine (0.07 mL, 0.42 mmol) under argon. The mixture cooled to 0° C., HATU (0.1 gm, 0.28 mmol) was added at that temperature and then stirred at room temperature for 4 h. After completion of reaction (by TLC), $H_2O$ (5 mL) was added drop by drop. The resulting yellow precipitate was filtered, washed with 2 mL of water, dried (high vacuum, 14 h) to furnish N-benzyl-3'-(benzylamino)-4'-nitrophenyl-2-carboxamide (0.11 g), 90% yield. $^1$H NMR (500 MHz, DMSO): 4.29 (d, J=6.0 Hz, 2H), 4.49 (d, J=5.9 Hz, 2H), 6.63 (dd, J=1.6 Hz, 1H), 6.87 (d, J=1.5 Hz, 1H), 7.10 (m, 1H), 7.18

(m, 3H), 7.27 (m, 2H) 7.38 (m, 5H), 7.50 (m, 3H), 7.99 (d, J=8.8 Hz, 1H), 8.60 (t, J=5.9 Hz, 1H), 8.77 (t, J=6.4 Hz, 1H). HRMS (ESI) calculated for C$_{27}$H$_{23}$N$_3$NaO$_3$: 460.1632, Found: 460.1614.

Example 51

3'-(benzylamino)-4'-nitrophenyl-4-carboxylic acid

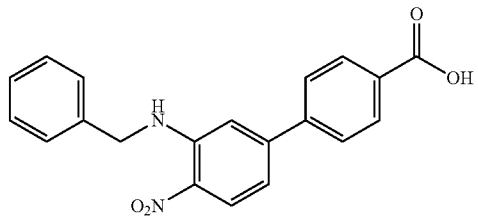 [SMILES: O=C(O)c1ccc(-c2ccc([N+](=O)[O-])c(NCc3ccccc3)c2)cc1]

To a solution of N-benzyl-5-bromo-2-nitrobenzenamine (0.5 g, 1.6 mmol) and 2-carbaethoxyphenylboronic acid (0.31 g, 2.4 mmol) in DME (5 mL) was added 2M Na$_2$CO$_3$ solution (2.5 ml, 4.8 mmol). After stirring reaction for 15 min under argon tetrakis (triphenylphosphine) palladium (0.092 mg, 0.08 mol) was added, resulting mixture was then heated at 80° C. for 20 h. It was then filtered through celite, evaporated under vacuum to get crude product. Flash column chromatography gave ethyl 3'-(benzylamino)-4'-nitrophenyl-4-carboxylate (0.49 g) in 80% yield; it was used for further reaction without purification.

To stirred solution of ethyl 3'-(benzylamino)-4'-nitrophenyl-4-carboxylate (0.4 g, 1.06 mmol) in THF:H$_2$O (3:1) was added lithium hydroxide (0.235 g, 10.6 mmol) at room temperature. The resulting mixture was stirred for 5 h, solvent was evaporated and residue was dissolved in water washed with dichloromethane. The aqueous layer was then neutralise with 2M HCl to get yellow solid 3'-(benzylamino)-4'-nitrophenyl-4-carboxylic acid (0.35 g), 94% yield $^1$H NMR (500 MHz, DMSO): 4.77 (d, J=6 Hz, 2H), 7.03 (dd, J=1.7 Hz, 1H), 7.18 (d, J=1.5 Hz, 1H), 7.26 (t, J=7.3 Hz, 1H), 7.38 (t, J=7.5, 7.7 Hz, 2H), 7.45 (d, J=7.4 Hz, 2H), 7.7 (d, J=8.3 Hz, 2H), 8.00 (m, 2H), 8.19 (d, J=8.9 Hz, 1H), 8.77 (t, J=5.6, 5.8 Hz, 1H), 13.00 (bs, 1H). HRMS (ESI) calculated for C$_{20}$H$_{16}$N$_2$NaO$_4$: 371.1002, Found: 371.0979.

Example 52

3' benzylamino)-4'-nitro-N-phenylbiphenyl-4-carboxamide

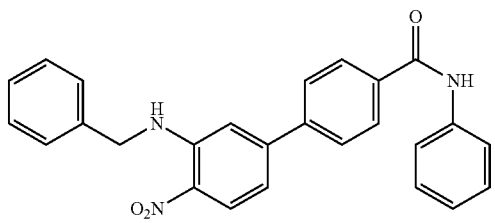 [SMILES: O=C(Nc1ccccc1)c1ccc(-c2ccc([N+](=O)[O-])c(NCc3ccccc3)c2)cc1]

To a solution of 3'-(benzylamino)-4'-nitrophenyl-4-carboxylic acid (0.1 g, 0.28 mmol) and aniline (0.025 mL, 0.28 mmol) in DMF (5 mL) was added diisopropylethylamine (0.07 mL, 0.42 mmol) under argon. The mixture cooled to 0° C., HATU (0.1 gm, 0.28 mmol) was added at that temperature and then stirred at room temperature for 4 h. After completion of reaction (by TLC), H$_2$O (5 mL) was added drop by drop. The resulting yellow precipitate was filtered, washed with 2 mL of water, dried (high vacuum, 14 h) to furnish 3'-(benzylamino)-4'-nitro-N-phenylbiphenyl-4-carboxamide (0.1 g), 92% yield. $^1$H NMR (500 MHz, DMSO): δ 4.78 (d, J=5.95 Hz, 2H), 7.05 (dd, J=1.8 Hz, 1H), 7.12 (m, 1H), 7.19 (d, J=1.8 Hz, 1H), 7.27 (m, 1H), 7.38 (m, 4H), 7.46 (d, J=7.1 Hz, 2H), 7.78 (m, 4H), 8.05 (m, 2H), 8.21 (d, J=8.9 Hz, 1H), 8.8 (t, J=5.6, 5.8 Hz, 1H), 10.3 (bs, 1H). HRMS (ESI) calculated for C$_{26}$H$_{21}$N$_3$NaO$_3$: 446.1475, Found: 446.1454.

Example 53

N-benzyl-3'-(benzylamino)-4'-nitrobiphenyl-4-carboxamide

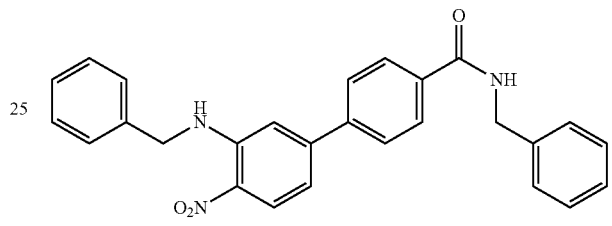

To a solution of 3'-(benzylamino)-4'-nitrophenyl-4-carboxylic acid (0.1 g, 0.28 mmol) and benzylamine (0.030 mL, 0.28 mmol) in DMF (5 mL) was added diisopropylethylamine (0.07 mL, 0.42 mmol) under argon. The mixture cooled to 0° C., HATU (0.1 gm, 0.28 mmol) was added at that temperature and then stirred at room temperature for 4 h. After completion of reaction (by TLC), H$_2$O (5 mL) was added drop by drop. The resulting yellow precipitate was filtered, washed with 2 mL of water, dried (high vacuum, 14 h) to furnish N-benzyl-3'-(benzylamino)-4'-nitrobiphenyl-4-carboxamide (0.1 g), 85% yield. $^1$H NMR (500 MHz, DMSO): 4.51 (d, J=6 Hz, 2H), 4.78 (d, J=5.95 Hz, 2H), 7.05 (dd, J=1.8, 1.9 Hz, 1H), 7.17 (d, J=1.8 Hz, 1H), 7.25 (m, 2H), 7.38 (m, 6H), 7.45 (d, J=7.1 Hz, 2H), 7.71 (m, 2H), 7.99 (m, 2H), 8.19 (d, J=8.9 Hz, 1H), 8.80 (t, J=5.6, 5.8 Hz, 1H), 9.16 (t, J=5.9, 6.0 Hz, 1H). HRMS (ESI) calculated for C$_{27}$H$_{23}$N$_3$NaO$_3$: 460.1632, Found: 460.1644.

Example 54

3'-(benzylamino)-4'-nitrophenyl-3-carboxylic acid

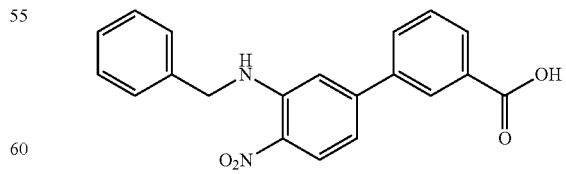

To a solution of N-benzyl-5-bromo-2-nitrobenzenamine (1 g, 3.2 mmol) and 3-carboxyphenylboronic acid (0.64 g, 3.92 mmol) in Toluene: EtOH: H$_2$O (8:8:1) was added K$_2$CO$_3$ (1.4 g, 9.78 mmol). After stirring reaction for 15 min under argon tetrakis (triphenylphosphine) palladium (0.184 mg, 0.016 mol) was added, resulting mixture was then heated at 100° C. for 12 h. The reaction mixture was cooled to room temperature and diluted with ethyl acetate and extracted three times with water. The aqueous layer was then acidified with 2M HCl to get 3'-(benzylamino)-4'-nitrophenyl-3-carboxylic acid (1.2 g), 94% yield. $^1$H NMR (500 MHz, DMSO): 4.76 (d, J=5.9 Hz, 2H), 7.00 (dd, J=1.8 Hz, 1H), 7.17 (d, J=1.75 Hz, 1H), 7.28 (m, 2H), 7.38 (m, 2H), 7.46 (d, J=7.5, 2H), 7.61 (t, J=7.7 Hz, 1H), 7.85 (m, 1H), 8.00 (m, 1H), 8.10 (m, 1H), 8.18 (d J=8.9 Hz, 1H), 8.79 (t, J=5.95, 1H) 13.10 (bs, 1H). HRMS (ESI) calculated for $C_{20}H_{16}N_2NaO_4$: 371.1002, Found: 371.0978.

Example 55

3'-(benzylamino)-4'-nitro-N-phenylbiphenyl-3-carboxamide

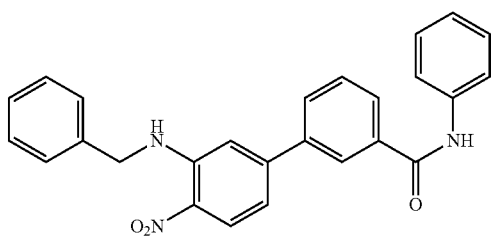 [SMILES: O=C(Nc1ccccc1)c1cccc(-c2ccc([N+](=O)[O-])c(NCc3ccccc3)c2)c1]

To a solution of 3'-(benzylamino)-4'-nitrophenyl-3-carboxylic acid (0.1 g, 0.28 mmol) and aniline (0.025 mL, 0.28 mmol) in DMF (5 mL) was added diisopropylethylamine (0.07 mL, 0.42 mmol) under argon. The mixture cooled to 0° C., HATU (0.1 gm, 0.28 mmol) was added at that temperature and then stirred at room temperature for 4 h. After completion of reaction (by TLC), H$_2$O (5 mL) was added drop by drop. The resulting yellow precipitate was filtered, washed with 2 mL of water, dried (high vacuum, 14 h) to furnish 3'-(benzylamino)-4'-nitro-N-phenylbiphenyl-3-carboxamide (0.098 g), 89% yield. $^1$H NMR (500 MHz, DMSO): 4.78 (d, J=5.9 Hz, 2H), 7.12 (m, 2H), 7.22 (m, 2H), 7.33 (m, 2H), 7.39 (m, 2H), 7.47 (d, J=7.5, 2H), 7.63 (t, J=7.7 Hz, 1H), 7.82 (m, 3H), 7.98 (m, 1H), 8.09 (m, 1H), 8.21 (d, J=8.9 Hz, 1H), 8.81 (t, J=5.95, 1H) 10.35 (bs, 1H). HRMS (ESI) calculated for $C_{26}H_{21}N_3NaO_3$: 446.1475, Found: 371.1453.

Example 56

N-benzyl-3'-(benzylamino)-4'-nitrobiphenyl-3-carboxamide

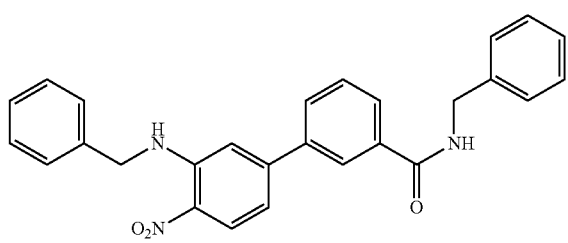 [SMILES: O=C(NCc1ccccc1)c1cccc(-c2ccc([N+](=O)[O-])c(NCc3ccccc3)c2)c1]

To a solution of 3'-(benzylamino)-4'-nitrophenyl-3-carboxylic acid (0.1 g, 0.28 mmol) and benzylamine (0.030 mL, 0.28 mmol) in DMF (5 mL) was added diisopropylethylamine (0.07 mL, 0.42 mmol) under argon. The mixture cooled to 0° C., HATU (0.1 gm, 0.28 mmol) was added at that temperature and then stirred at room temperature for 4 h. After completion of reaction (by TLC), H$_2$O (5 mL) was added drop by drop. The resulting yellow precipitate was filtered, washed with 2 mL of water, dried (high vacuum, 14 h) to furnish N-benzyl-3'-(benzylamino)-4'-nitrobiphenyl-3-carboxamide (0.11 g), 92% yield. $^1$H NMR (500 MHz, DMSO): 4.53 (d, J=5.9 Hz, 2H), 4.76 (d, J=5.9 Hz, 2H), 7.07 (dd, J=1.8 Hz, 1H), 7.20 (d, J=1.7 Hz, 2H), 7.25 (m, 2H), 7.35 (m, 5H), 7.45 (d, J=7.2, 2H), 7.60 (t, J=7.8, 7.7 Hz, 1H), 7.78 (m, 1H), 7.95 (m, 1H), 8.13 (m, 1H), 8.20 (d, J=8.9 Hz, 1H), 8.78 (t, J=5.95, 1H), 9.16 (t, J=5.9, 1H).

HRMS (ESI) calculated for $C_{27}H_{23}N_3NaO_3$: 460.1632, Found: 460.1615.

SCHEME 10: Examples 57-60

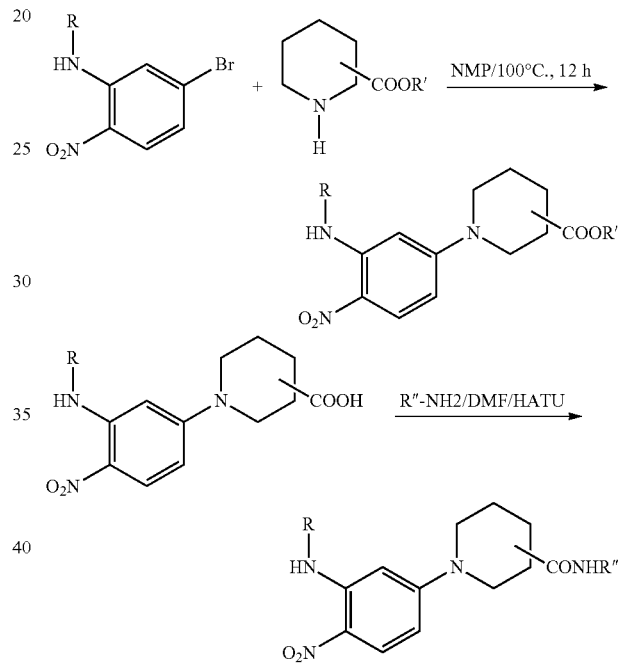

The following exemplary compounds were synthesized using this scheme:

Example 57 ethyl-1-(3-(benzylamino)-4-nitrophenyl)piperidine-4-carboxylate

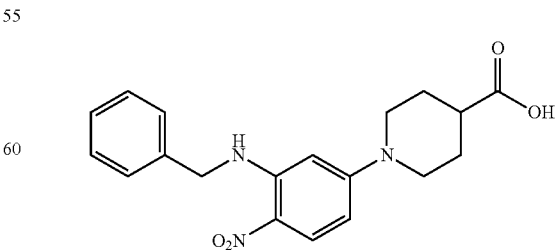

A solution of N-benzyl-5-bromo-2-nitrobenzenamine (1.5 g, 4.9 mmol) and ethyl isonipecoate (1.53 g, 9.8 mmol) in NMP (15 mL) was added diisopropylethylamine (1.18 mL, 7.35 mmol). The resulting mixture was then heated at 100° C. for 12 h. The solution was then cooled to room temperature to which water was added and extracted thrice with ethyl acetate. The combined ethyl acetate extract was then evaporated under vacuum to get crude product. Flash column chromatography gave ethyl-1-(3-(benzylamino)-4-nitrophenyl) piperidine-4-carboxylate (1.6 g) in 85% yield. $^1$H NMR (500 MHz, CDCl$_3$): δ 1.29 (t, J=7.1 Hz, 3H), 1.72 (m, 2H), 1.95 (m, 2H), 2.54 (m, 1H), 3.0 (m, 2H), 3.76 (m, 2H), 4.12 (q, J=7.1 Hz, 2H), 4.54 (d, J=5.5 Hz, 2H), 5.86 (d, J=2.5 Hz, 1H), 6.25 (dd, J=2.6 Hz, 1H), 7.27 (m, 1H), 7.37 (m, 5H), 8.11 (d, J=9.7 Hz, 1H), 8.84 (m, 1H).

To stirred solution of ethyl-1-(3-(benzylamino)-4-nitrophenyl)piperidine-4-carboxylate (2 g, 6.2 mmol) in 20 ml THF: H$_2$O (3:1) was added lithium hydroxide (0.740 g, 30.9 mmol) at room temperature. The resulting mixture was stirred for 5 h, solvent was evaporated and residue was dissolved in water washed with dichloromethane. The aqueous layer was then neutralised with 2M HCl to get yellow solid 1-(3-(benzylamino)-4-nitrophenyl)piperidine-4-carboxylic acid (1.5 g), 90% yield: $^1$H NMR (500 MHz, DMSO): δ 1.46 (m, 2H), 1.80 (m, 2H), 3.03 (m, 2H), 3.82 (m, 2H), 4.59 (d, J=5.7 Hz, 2H), 5.94 (d, J=2.5 Hz, 1H), 6.40 (dd, J=2.5 Hz, 1H), 7.27 (m, 1H), 7.37 (m, 2H) 7.42 (m, 2H), 7.90 (d, J=9.8 Hz, 1H), 8.83 (m, 1H). HRMS (ESI) calculated for C$_{19}$H$_{21}$N$_3$NaO$_4$: 378.1424, Found: 378.1417.

Example 58

1-(3-(benzylamino)-4-nitrophenyl)-N-phenyl piperidine-4-carboxamide

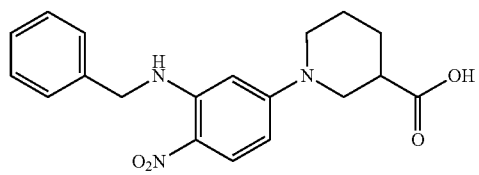

To a solution of 1-(3-(benzylamino)-4-nitrophenyl)piperidine-4-carboxylic acid (0.2 g, 0.56 mmol) and aniline (0.052 mL, 0.56 mmol) in DMF (5 mL) was added diisopropylethylamine (0.198 mL, 1.12 mmol) under argon. The mixture cooled to 0° C., HATU (0.212 g, 0.56 mmol) was added at that temperature and then stirred at room temperature for 4 h. After completion of reaction (by TLC), H$_2$O (5 mL) was added drop by drop. The resulting yellow precipitate was filtered, washed with 2 mL of water, dried (high vacuum, 14 h) to furnish 1-(3-(benzylamino)-4-nitrophenyl)-N-phenyl piperidine-4-carboxamide (0.21 g), 87% yield. $^1$H NMR (500 MHz, DMSO): δ 1.57 (m, 2H), 1.82 (m, 2H), 2.65 (m, 1H), 2.99 (m, 2H), 3.98 (m, 2H), 4.60 (d, J=5.7 Hz, 2H), 5.97 (d, J=2.5 Hz, 1H), 6.44 (dd, J=2.5 Hz, 1H), 7.03 (m, 1H), 7.29 (m, 3H) 7.37 (m, 2H), 7.43 (m, 2H), 7.60 (m, 2H), 7.92 (d, J=9.7 Hz, 1H), 8.84 (m, 1H), 9.9 (bs, 1H). HRMS (ESI) calculated for C$_{25}$H$_{27}$N$_4$O$_3$: 431.2078, Found: 431.2005.

Example 59

N-benzyl-1-(3-(benzylamino)-4-nitrophenyl)piperidine-4-carboxamide

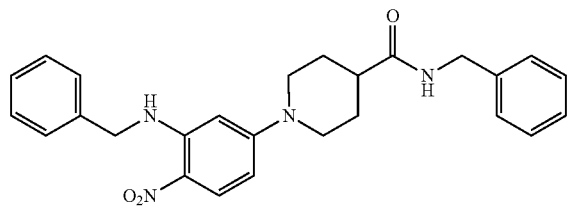 [SMILES: O=C(NCc1ccccc1)C1CCN(c2ccc([N+](=O)[O-])c(NCc3ccccc3)c2)CC1]

To a solution of 1-(3-(benzylamino)-4-nitrophenyl)piperidine-4-carboxylic acid (0.2 g, 0.56 mmol) and benzylamine (0.06 mL, 0.56 mmol) in DMF (5 mL) was added diisopropylethylamine (0.198 mL, 1.12 mmol) under argon. The mixture cooled to 0° C., HATU (0.212 g, 0.56 mmol) was added at that temperature and then stirred at room temperature for 4 h. After completion of reaction (by TLC), H$_2$O (5 mL) was added drop by drop. The resulting yellow precipitate was filtered, washed with 2 mL of water, dried (high vacuum, 14 h) to furnish N-benzyl-1-(3-(benzylamino)-4-nitrophenyl)piperidine-4-carboxamide (0.21 g), 84% yield. $^1$H NMR (500 MHz, DMSO): δ 1.51 (m, 2H), 1.74 (m, 2H), 2.48 (m, 1H), 2.96 (m, 2H), 3.93 (m, 2H), 4.26 (d, J=5.9 Hz, 2H), 4.59 (d, J=5.8 Hz, 2H), 5.95 (d, J=2.45 Hz, 1H), 6.42 (dd, J=2.5 Hz, 1H), 7.24 (m, 4H) 7.37 (m, 4H), 7.42 (m, 2H), 7.91 (d, J=9.7 Hz, 1H), 8.35 (m, 1H), 8.84 (m, 1H). HRMS (ESI) calculated for C$_{26}$H$_{28}$N$_4$NaO$_3$: 467.2054, Found: 467.2054.

Example 60

1-(3-(benzylamino)-4-nitrophenyl)piperidine-3-carboxylic acid

A solution of N-benzyl-5-bromo-2-nitrobenzenamine (0.5 g, 1.6 mmol) and ethyl nipecoate (0.5 g, 3.2 mmol) in NMP (15 mL) was added diisopropylethylamine (0.4 mL, 2.4 mmol). The resulting mixture was then heated at 100° C. for 12 h. The solution was then cooled to room temperature to which water was added and extracted thrice with ethyl acetate. The combined ethyl acetate extract was then evaporated under vacuum to get crude product. Flash column chromatography gave ethyl-1-(3-(benzylamino)-4-nitrophenyl) piperidine-3-carboxylate (0.42 g), 70% yield: $^1$H NMR (500 MHz, CDCl$_3$): δ 1.30 (t, J=7.1 Hz, 3H), 1.55 (m, 1H), 1.77 (m, 2H), 2.07 (m, 1H), 2.55 (m, 1H), 3.04 (m, 1H), 3.27 (m, 1H), 3.62 (m, 1H), 3.85 (m, 1H), 4.20 (q, J=7.1 Hz, 2H), 4.54 (d, J=5.5 Hz, 2H), 5.90 (d, J=2.6 Hz, 1H), 6.25 (dd, J=2.6 Hz, 1H), 7.37 (m, 5H), 8.12 (d, J=9.7 Hz, 1H), 8.84 (m, 1H).

To stirred solution of ethyl-1-(3-(benzylamino)-4-nitrophenyl)piperidine-3-carboxylate (1 g, 3.1 mmol) in 10 ml THF: H₂O (3:1) was added lithium hydroxide (0.35 g, 15.4 mmol) at room temperature. The resulting mixture was stirred for 5 h, solvent was evaporated and residue was dissolved in water washed with dichloromethane. The aqueous layer was then neutralised with 2M HCl to get yellow solid 1-(3-(benzylamino)-4-nitrophenyl)piperidine-3-carboxylic acid (0.7 g), 86% yield: ¹H NMR (500 MHz, DMSO): δ 1.55 (m, 1H), 1.87 (m, 2H), 2.10 (m, 1H), 2.62 (m, 1H), 3.07 (m, 1H), 3.30 (m, 1H), 3.60 (m, 1H), 3.82 (dd, J=3.6, 5.6 Hz, 1H), 4.55 (d, J=5.4 Hz, 2H), 5.92 (d, J=2.5 Hz, 1H), 6.28 (dd, J=2.6 Hz, 1H), 7.32 (m, 2H), 7.41 (m, 3H), 8.12 (d, J=9.6 Hz, 1H), 8.8 (m, 1H).

SCHEME 11: Examples 61-69

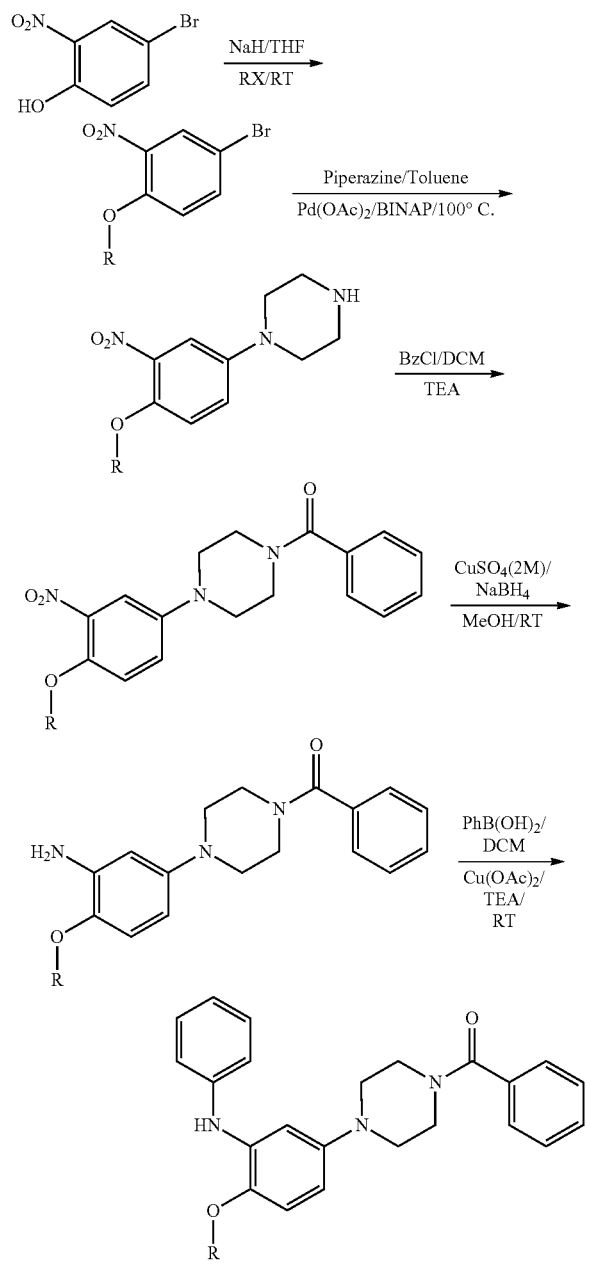

The following compounds were synthesized, some as intermediates for this scheme, others exemplary compounds of this scheme:

Example 61

4-bromo-2-nitroanisole

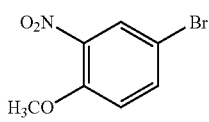

4-Bromo-2-nitrophenol (5.0 g, 23 mmol) and sodium hydride (0.6 g, 25.3 mmol) were suspended in DMF (50 ml). Methyl iodide (3.9 mL, 28 mmol) was added dropwise at room temperature and stirred for 30 minutes. Water was added slowly to reaction mixture to get precipitate of 4-bromo-2-nitroanisole (0.67 g), 90% yield. The crude solid that was used without further purification. ¹H NMR (500 MHz, CDCl₃): δ 3.98 (s, 3H), 7.03 (d, J=8.9 Hz, 1H), 7.68 (dd, J=2.45 Hz, 1H), 8.01 (d, J=2.45 Hz, 1H). ¹³C NMR (500 MHz, CDCl₃): δ 56.9, 112.0, 115.3, 128.5, 137.1, 140.2, 152.3.

Example 62

(4-(4-methoxy-3-nitrophenyl)piperazin-1-yl) (phenyl)methanone

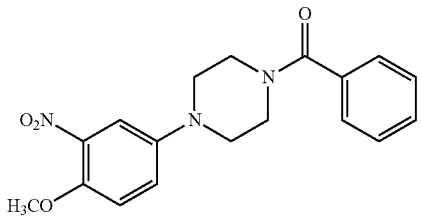 [SMILES: COc1ccc(N2CCN(C(=O)c3ccccc3)CC2)cc1[N+](=O)[O-]]

Palladium (II) acetate (0.094 g, 0.43 mmol) and rac-2,2'-bis (diphenylphosphino)-1,1'-binapthyl (0.38 g, 0.6 mmol) were heated to 50° C. in dioxane (20 mL) for 30 minutes. Cesium carbonate (8.38 g, 23.8 mmol), 4-bromo-2-nitroanisole (2.0 g, 8.6 mmol) and piperazine (1.47 g, 1.72 mmol) were added and the mixture heated at reflux for 18 hours. The solids were filtered through celite and washed with ethyl acetate. The filtrate was evaporated under vacuum to get crude residue. The residue was purified by flash column chromatography to afford 1-(4-methxoy-3-nitrophenyl)piperazine (1.3 g) 65% yield, which was used for next step without further purification.

1-(4-methxoy-3-nitrophenyl)piperazine (2.3 g, 10 mmol) and triethylamine (4.2 mL, 30 mmol) were dissolved in dichloromethane (50 ml), cooled to 0° C. Benzoyl chloride (1.5 ml, 13 mmol) was added drop by drop at 0° C., after addition is over reaction was brought to room temperature and stirred for 3 h. After completion of reaction (by TLC) solvent was evaporated, residue was purified by flash column chromatography to afford (4-(4-methoxy-3-nitrophenyl)piperazin-1-yl) (phenyl)methanone (2.8 g), 85% yield: ¹H NMR (500 MHz, CDCl₃): δ 3.10 (bs, 2H), 3.20 (bs, 2H), 3.92 (s, 3H), 3.96 (bs, 2H), 7.07 (d, J=9.15 Hz, 1H), 7.18 (dd, J=3.0 Hz, 1H), 7.44 (d, J=3 Hz, 1H), 7.48 (m, 5H).

Example 63

(4-(3-amino-4-methoxyphenyl)piperazin-1-yl) (phenyl)methanone

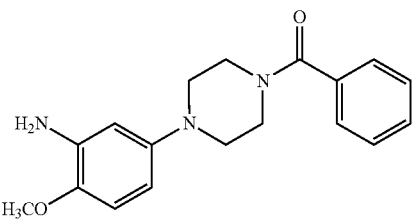

To a stirred solution of (4-(4-methoxy-3-nitrophenyl)piperazin-1-yl) (phenyl)methanone (3.41 g, 10 mmol) and 2M CuSO$_4$ (0.160 g, 1 mmol) in methanol (50 mL), NaBH4 (1.89 g, 50 mmol) was added in portions at room temperature. After stirring it for 30 min, it was filtered through celite, filtrate was evaporated under vacuum. Flash column chromatography afforded (4-(3-amino-4-methoxyphenyl)piperazin-1-yl) (phenyl)methanone (2.7 g,) 87% yield. $^1$H NMR (500 MHz, CDCl$_3$): δ 3.0 (bs, 2H), 3.15 (bs, 2H), 3.59 (bs, 2H), 3.84 (s, 5H), 3.98 (bs, 2H), 6.34 (dd, J=2.8 Hz, 1H), 6.43 (d, J=2.7 Hz, 1H), 6.75 (d, J=8.6 Hz, 1H), 7.45 (m, 5H). $^{13}$C NMR (500 MHz, CDCl$_3$): δ 42.4, 48.0, 56.3, 51.2, 51.5, 56.1, 105.9, 107.1, 111.3, 127.3, 128.7, 129.9, 135.9, 136.9, 142.6, 146.0, 170.5.

Example 64

4-(4-methoxy-3-(phenylamino)phenyl)piperazin-1-yl)(phenyl)methanone

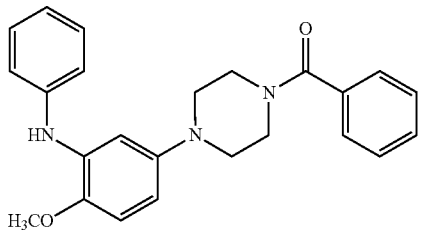

To a stirred solution of (4-(3-amino-4-methoxyphenyl)piperazin-1-yl) (phenyl)methanone (2 g, 6.4 mmol) and phenylboronic acid (2.34 g, 19.2 mmol) in DCM (100 mL) was added triethylamine (2.7 mL, 19.2 mmol) and Cu(OAc)$_2$ (1.74 g, 9.6 mmol). The mixture was stirred for 12 h. It was then filtered through celite, evaporated under vacuum. Flash column chromatography gave (4-(4-methoxy-3-(phenylamino) phenyl)piperazin-1-yl)(phenyl)methanone (2.0 g), 80% yield. $^1$H NMR (500 MHz, CDCl$_3$): δ 3.0 (bs, 2H), 3.15 (bs, 2H), 3.59 (bs, 2H), 3.89 (s, 3H), 3.95 (bs, 2H), 6.18 (s, 1H), 6.46 (dd, J=2.5, 3 Hz 1H), 6.85 (d, J=9 Hz, 1H), 7.01 (m, 2H), 7.19 (d, J=7.5 Hz, 2H), 7.34 (m, 2H), 7.49 (m, 5H).

HRMS (ESI) calculated for C$_{24}$H$_{26}$N$_3$O$_2$: 388.2020, Found: 388.2012.

Example 65

4-bromo-2-nitro-1-[(phenylmethyl)oxy]benzene

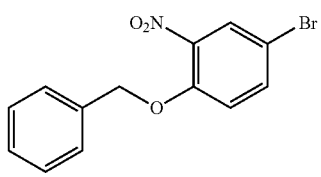 [SMILES: O=[N+]([O-])c1cc(Br)ccc1OCc1ccccc1]

To a solution of 4-bromo-2-nitrophenol (5.2 g, 23.8 mmol) in acetone (100 ml) was added potassium carbonate (9.0 g, 65.1 mmol) followed by benzyl bromide (2.6 ml, 21.8 mmol). The resulting mixture was stirred at room temperature for 30 minutes and then heated to reflux overnight. The solids were then removed by filtration, washing with acetone, and the filtrate reduced in vacuo. The residue was dissolved in ethyl acetate and washed with 2M aqueous sodium hydroxide solution (×3) and then brine. The organic layer was separated, dried over anhydrous magnesium sulfate, filtered and reduced in vacuo to afford 4-bromo-2-nitro-1-[(phenylmethyl)oxy] benzene (6 g), 92% yield. $^1$H NMR (500 MHz, CDCl$_3$): δ 5.26 (s, 2H), 7.05 (d, J=8.9 Hz, 1H), 7.42 (m, 5H), 7.63 (dd, J=2.5 Hz, 1H), 8.01 (d, J=2.45 Hz, 1H). $^{13}$C NMR (500 MHz, CDCl$_3$): δ 71.6, 112.4, 116.9, 127.1, 128.5, 128.6, 128.9, 135.2, 136.9, 140.7, 151.2.

Example 66

1-(4-(benzyloxy)-3-nitrophenyl)piperazine

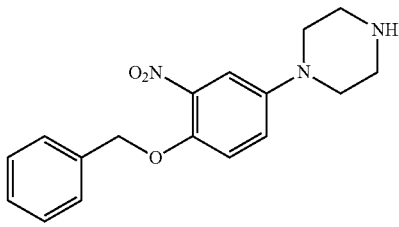 [SMILES: O=[N+]([O-])c1cc(N2CCNCC2)ccc1OCc1ccccc1]

To a solution of 4-bromo-2-nitro-1-[(phenylmethyl)oxy] benzene (3.08 g, 10 mmol) in dioxane (60 ml) was added piperazine (2.58 g, 30 mmol) followed by cesium carbonate (4.8 g, 15 mmol), rac-2,2' bis(diphenylphosphino)-1,1'-binapthyl (0.311 g, 0.5 mmol) and palladium acetate (0.112 g, 0.5 mmol). The resulting mixture was heated at 100° C. under an atmosphere of argon overnight. The mixture was allowed to cool, charcoal was added and the mixture stirred at room temperature for 30 minutes. The solids were then removed by filtration through celite and the residue washed with ethyl acetate. The filtrate was then reduced in vacuo and the residue was purified by flash column chromatography gave 1-(4-(benzyloxy)-3-nitrophenyl)piperazine which was used for next step without further purification.

Example 67

(4-(4-benzyloxy)-3-nitrophenyl)piperazin-1-yl) (phenyl)methanone

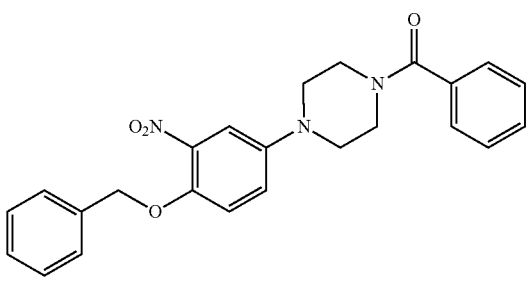 [SMILES: O=C(c1ccccc1)N1CCN(c2ccc(OCc3ccccc3)c([N+](=O)[O-])c2)CC1]

1-(4-(benzyloxy)-3-nitrophenyl)piperazine (2.3 g, 7.35 mmol) and triethylamine (3 mL, 22.05 mmol) were dissolved in dichloromethane (50 ml), cooled to 0° C. Benzoyl chloride (1.0 ml, 8.8 mmol) was added drop by drop at 0° C., after addition is over reaction was brought to room temperature and stirred for 3 h. After completion of reaction (by TLC) solvent was evaporated, residue was purified by flash column chromatography to afford (4-(4-benzyloxy)-3-nitrophenyl) piperazin-1-yl) (phenyl)methanone (3.0 g), 92% yield. This was used for next step without further purification.

Example 68

(4-(3-amino-4-(benzyloxy)phenyl)piperazin-1-yl) (phenyl)methanone

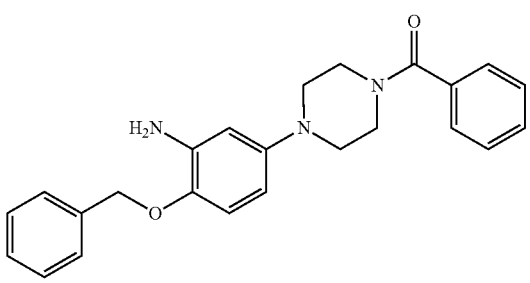 [SMILES: Nc1cc(N2CCN(C(=O)c3ccccc3)CC2)ccc1OCc1ccccc1]

A mixture of (4-(4-benzyloxy)-3-nitrophenyl)piperazin-1-yl) (phenyl)methanone (3.7 g, 10.8 mmol) in methanol (60 ml) was treated with iron powder (3.03 g, 54.3 mmol) and the resulting mixture heated to 50° C. under an atmosphere of argon. After 15 minutes, a solution of ammonium chloride (4.64 g, 86.7 mmol) in water (30 ml) was added and the resulting mixture heated to 70° C. and kept at this temperature for 17 hours. The mixture was then allowed to cool over 1.5 hours and was then filtered through celite, washing with methanol and the filtrate reduced in vacuo. The residue was re-suspended in methanol, filtered again and the filtrate reduced and the residue purified by chromatography on silica gel to give a brown residue which partially solidified on standing overnight. Trituration with diethyl ether afforded (4-(3-amino-4-(benzyloxy) phenyl)piperazin-1-yl) (phenyl) methanone (2.7 g), 80% yield. $^1$H NMR (500 MHz, CDCl$_3$): δ 3.01 (bs, 2H), 3.16 (bs, 2H), 3.59 (bs, 2H), 3.87 (s, 2H), 3.95 (bs, 2H), 5.06 (s, 2H), 6.32 (dd, J=2.8 Hz, 1H), 6.44 (d, J=2.8 Hz, 1H), 6.82 (d, J=8.6 Hz, 1H), 7.45 (m, 10H). $^{13}$C NMR (500 MHz, CDCl$_3$): 42.4, 47.9, 50.9, 51.3, 71.1, 105.7, 107.0, 113.3, 127.2, 127.7, 128.1, 128.7, 129.9, 135.8, 137.4 (x2), 141.6, 146.3, 170.5.

Example 69

(4-(4-(benzyloxy)-3-(phenylamino) phenyl)piperazin-1-yl) (phenyl)methanone

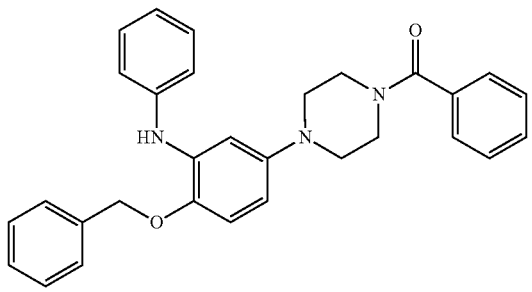 [SMILES: O=C(c1ccccc1)N1CCN(c2ccc(OCc3ccccc3)c(Nc3ccccc3)c2)CC1]

To a stirred solution of (4-(3-amino-4-(benzyloxy)phenyl) piperazin-1-yl)(phenyl) methanone (1 g, 2.58 mmol) and phenylboronic acid (0.94 g, 7.74 mmol) in DCM (100 mL) was added triethylamine (1.0 mL, 7.74 mmol) and Cu(OAc)$_2$ (0.7 g, 3.87 mmol). The mixture was stirred for 12 h. It was then filtered through celite, evaporated under vacuum. Flash column chromatography gave (4-(4-(benzyloxy)-3-(phenylamino) phenyl) piperazin-1-yl) (phenyl)methanone (0.87 g), 82% yield. $^1$H NMR (500 MHz, DMSO): δ 3.01 (bs, 2H), 3.16 (bs, 2H), 3.59 (bs, 2H), 3.95 (bs, 2H), 5.10 (s, 2H), 6.20 (s, 1H), 6.42 (dd, J=2.5, 3 Hz 1H), 6.91 (d, J=8.5 Hz, 1H), 7.01 (m, 2H), 7.17 (d, J=8.0 Hz, 2H), 7.32 (m, 2H), 7.37 (m, 10H). HRMS (ESI) calculated for C$_{30}$H$_{30}$N$_3$O$_2$: 464.2333, Found: 464.2338.

Example 70

Table 1

Compounds Showing Activity Observed in a ThT Functional Aβ 1-40 Aggregation Assay The following methodologies were used:
Preparation of Aβ$_{40}$ Stock Solutions
Aβ$_{40}$ (1.0 mg) was pre-treated in a 1.5 mL microfuge tube with HFIP (1 mL) and sonicated for 20 min to disassemble any pre-formed Aβ aggregates. The HFIP was removed with a stream of argon and the Aβ dissolved in Tris base (5.8 mL, 20 mM, pH ~10). The pH was adjusted to 7.4 with concentrated HCl (~10 μL) and the solution filtered using a syringe filter (0.2 μm) before being used.
ThT Aβ Aggregation Assay
The kinetic ThT assay for Aβ aggregation is similar to that of Chalifour et al (Chalifour et al, 2003, J. Biol. Chem. 278: 34874-81). Briefly, pre-treated Aβ40 (40 μM in 20 mM Tris, pH 7.4), was diluted with an equal volume of 8 μM ThT in Tris (20 mM, pH 7.4, 300 mM NaCl). Aliquots of Aβ/ThT (200 μL) were added to wells of a black polystyrene 96-well plate, followed by 2 μL of a compound in DMSO (variable concentration), or DMSO alone (controls). Incubations were performed in triplicate and were taken to contain 20 μM Aβ, various concentration of compound in 20 mM Tris, pH 7.4, 150 mM NaCl, 1% DMSO. Plates were covered with clear polystyrene lids and incubated at 37° C. in a Tecan Genios microplate reader. Fluorescence readings ($\lambda$ex=450 nm, $\lambda$em=480 nm) were taken every 15 min., after first shaking at high intensity for 15 s and allowing to settle for 10 s before each reading. Active compounds attenuated the increase in fluorescence over time that occurred in controls. By repeating this procedure over several concentrations, a mean inhibitory concentration ($IC_{50}$) was measured, as given in the table below. The column "A-syn" represents a similar procedure measuring inhibition of alpha-synuclein aggregation. The column "ratio" is a reproducible assessment of potency with respect to the compound of Example 7, in which 1=potency of that compound:

TABLE 1

| Structure | Aβ-ThT ($IC_{50}$/ μM) | Ratio | A-syn ($IC_{50}$/ μM) |
|---|---|---|---|
| 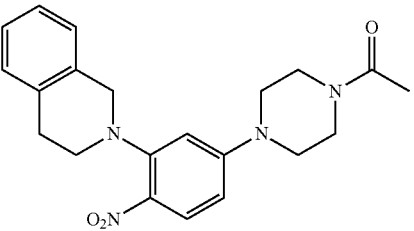 [SMILES: CC(=O)N1CCN(c2ccc([N+](=O)[O-])c(N3CCc4ccccc4C3)c2)CC1] | | 4.03 | |
| 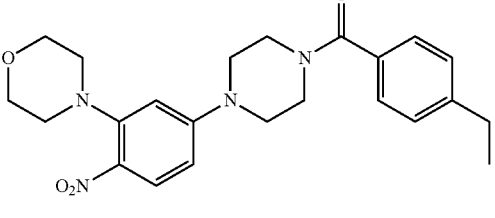 | | 2.7 | |
| 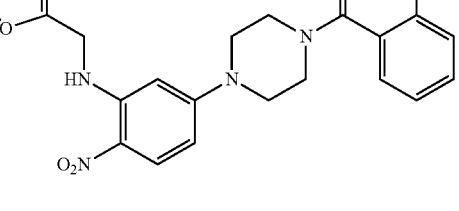 | | 2.1 | |
| 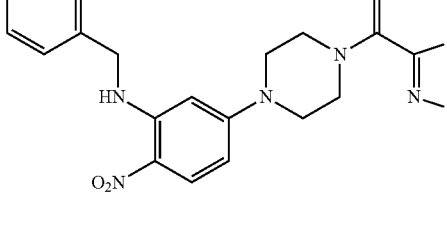 | | 1.4 | |
| 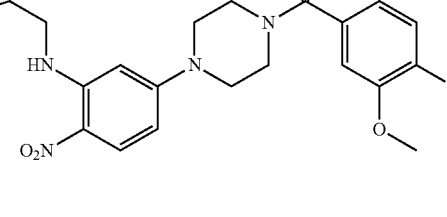 | | >20 | |

TABLE 1-continued

| Structure | Aβ-ThT (IC₅₀/ μM) | Ratio | A-syn (IC₅₀/ μM) |
|---|---|---|---|
| 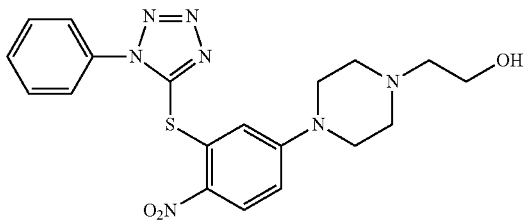 [SMILES: O=[N+]([O-])c1ccc(N2CCN(CCO)CC2)cc1Sc1nnnn1-c1ccccc1] | — | | |
| | >20 | | |
| | >20 | | |
| 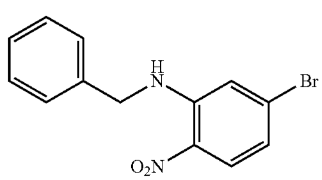 [SMILES: O=[N+]([O-])c1ccc(Br)cc1NCc1ccccc1] | 20-50 | | |
| 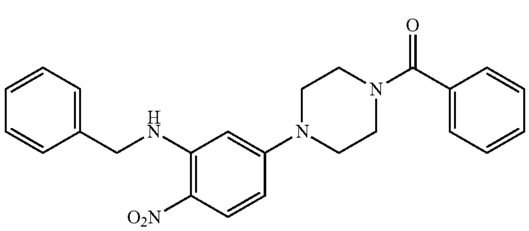 [SMILES: O=C(c1ccccc1)N1CCN(c2ccc([N+](=O)[O-])c(NCc3ccccc3)c2)CC1] | 10-20 | 0.09 | 51 |
| 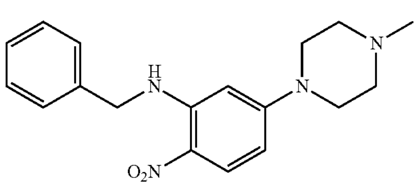 [SMILES: CN1CCN(c2ccc([N+](=O)[O-])c(NCc3ccccc3)c2)CC1] | 9.0 | 0.1 | 11.61 |

TABLE 1-continued

| Structure | Aβ-ThT (IC$_{50}$/ μM) | Ratio | A-syn (IC$_{50}$/ μM) |
|---|---|---|---|
| (phenyl-NH, 2-NO$_2$, 4-piperazine-N-C(O)-phenyl) | 0.85 | 1 | 6.34 |
| (propyl-NH, 2-NO$_2$, 4-piperazine-N-C(O)-phenyl) | 2.5 | 0.34 | 142 |
| (benzyl-NH, 2-NO$_2$, 4-piperazine-N-C(O)CH$_3$) | 25.8 | 0.58 | |
| (phenyl-NH, 2-NO$_2$, 4-piperazine-NH) | 8.82 | 0.54 | |
| (phenoxy, 2-NO$_2$, 4-piperazine-N-C(O)-phenyl) | >50 | | |
| (phenyl-NH, 2-NO$_2$, 4-(4-methylpiperazine)) | 23.2 | 0.42 | |
| (phenyl-NH, 2-NO$_2$, 4-(4-benzylpiperazine)) | >50 | | |

TABLE 1-continued

| Structure | Aβ-ThT (IC$_{50}$/ μM) | Ratio | A-syn (IC$_{50}$/ μM) |
|---|---|---|---|
| [structure: phenyl-NH-(nitrophenyl)-piperazine-SO$_2$-phenyl] | >50 | | |
| [structure: phenyl-NH-(nitrophenyl)-piperidine] | >100 | | |
| [structure: phenyl-NH-(nitrophenyl)-morpholine] | 23 | 0.40 | |
| [structure: phenyl-NH-(nitrophenyl)-piperazine-SO$_2$-CH$_3$] | >50 | | |
| [structure: phenyl-NH-(nitrophenyl)-piperazine-C(O)-N(CH$_3$)$_2$] | 8.4 | 0.72 | |
| [structure: phenyl-NH-(nitrophenyl)-N(CH$_3$)$_2$] | 39 | 0.15 | |
| [structure: PhC(O)NH-(nitrophenyl)-piperazine-C(O)Ph] | 177.5 | 0.05 | |

TABLE 1-continued

| Structure | Aβ-ThT (IC$_{50}$/ μM) | Ratio | A-syn (IC$_{50}$/ μM) |
|---|---|---|---|
| (structure) | 9.64 | 0.9 | 5 |
| (structure) | 44 | 0.19 | |
| (structure) | 25 | 0.88 | 4 |
| (structure) | 100 | 0.21 | |
| (structure) | 41.9 | 0.5 | |
| (structure) | 184 | 0.02 | |
| (structure) | 152 | 0.03 | |

TABLE 1-continued

| Structure | Aβ-ThT (IC$_{50}$/ μM) | Ratio | A-syn (IC$_{50}$/ μM) |
|---|---|---|---|
| 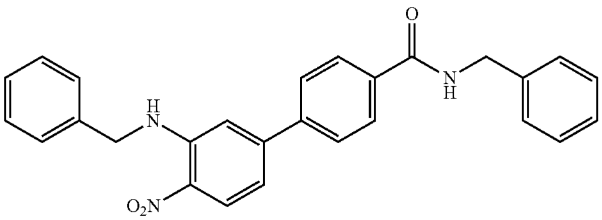 [SMILES: O=C(NCc1ccccc1)c1ccc(-c2ccc([N+](=O)[O-])c(NCc3ccccc3)c2)cc1] | 42 | 0.11 | |
| 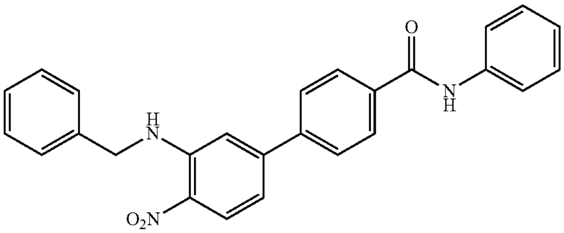 [SMILES: O=C(Nc1ccccc1)c1ccc(-c2ccc([N+](=O)[O-])c(NCc3ccccc3)c2)cc1] | 217 | 0.07 | |
| 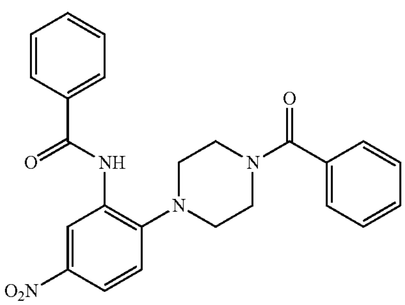 [SMILES: O=C(Nc1cc([N+](=O)[O-])ccc1N1CCN(C(=O)c2ccccc2)CC1)c1ccccc1] | 1035 | 0.01 | |
| 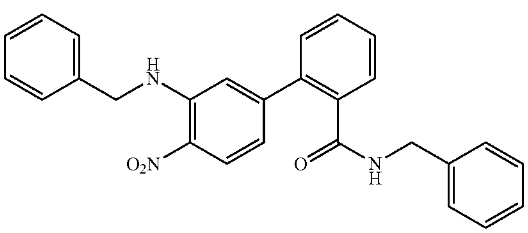 [SMILES: O=C(NCc1ccccc1)c1ccccc1-c1ccc([N+](=O)[O-])c(NCc2ccccc2)c1] | 631 | 0.02 | |
| 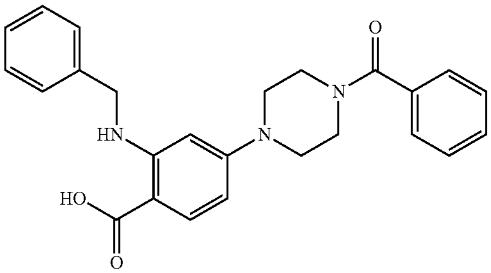 [SMILES: O=C(O)c1ccc(N2CCN(C(=O)c3ccccc3)CC2)cc1NCc1ccccc1] | 189 | 0.05 | |
| 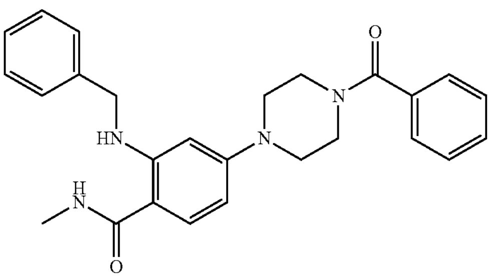 [SMILES: CNC(=O)c1ccc(N2CCN(C(=O)c3ccccc3)CC2)cc1NCc1ccccc1] | ND | ND | |

TABLE 1-continued

| Structure | Aβ-ThT (IC$_{50}$/ μM) | Ratio | A-syn (IC$_{50}$/ μM) |
|---|---|---|---|
| *[structure: 4-benzoylpiperazinyl-N,N-dimethylbenzamide with benzylamino substituent]* | 84 | 0.11 | |
| *[structure: 1-benzoyl-4-(3-nitrophenyl)piperazine]* | 196 | 0.04 | |
| *[structure: 4-(4-benzoylpiperazin-1-yl)-2-(benzylamino)benzamide]* | 265 | 0.03 | |
| *[structure: 4-(4-benzoylpiperazin-1-yl)-2-(benzylamino)-N-ethylbenzamide]* | 66.2 | 0.13 | |
| *[structure: N-benzyl-2-nitroaniline]* | 63 | 0.38 | |

TABLE 1-continued

| Structure | Aβ-ThT (IC$_{50}$/ μM) | Ratio | A-syn (IC$_{50}$/ μM) |
|---|---|---|---|
| [structure] | 174 | 0.14 | |
| [structure] | 18 | 0.22 | |
| [structure] | 105 | 0.04 | |
| [structure] | 1.47 | 2.85 | 8 |
| [structure] | 5734 | 0 | |
| [structure] | 14935 | 0 | |
| [structure] | 23 | 0.89 | |

TABLE 1-continued

| Structure | Aβ-ThT (IC$_{50}$/ μM) | Ratio | A-syn (IC$_{50}$/ μM) |
|---|---|---|---|
| 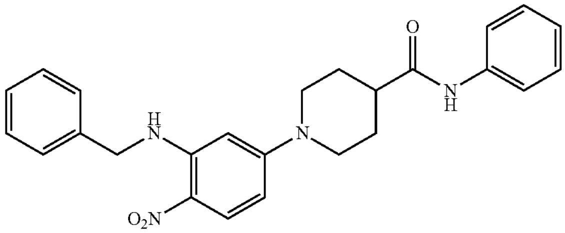 [SMILES: O=C(Nc1ccccc1)C1CCN(c2ccc([N+](=O)[O-])c(NCc3ccccc3)c2)CC1] | 544 | 0.05 | |
| 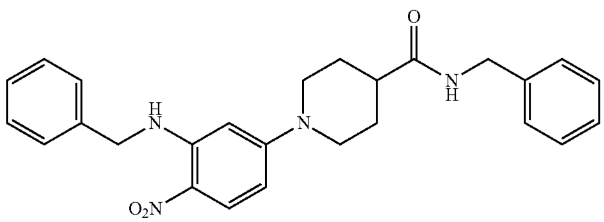 [SMILES: O=C(NCc1ccccc1)C1CCN(c2ccc([N+](=O)[O-])c(NCc3ccccc3)c2)CC1] | 975 | 0.03 | |
| 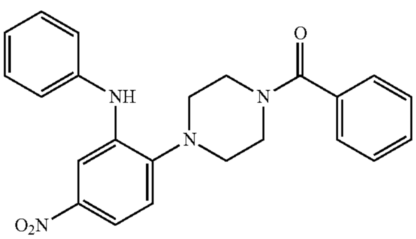 [SMILES: O=C(c1ccccc1)N1CCN(c2ccc([N+](=O)[O-])cc2Nc2ccccc2)CC1] | 92 | 0.34 | |
| 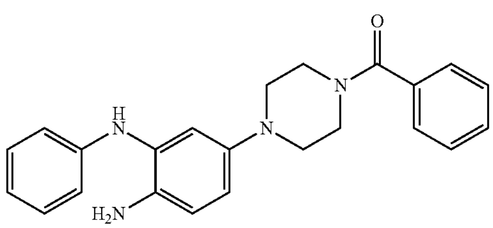 [SMILES: Nc1ccc(N2CCN(C(=O)c3ccccc3)CC2)cc1Nc1ccccc1] | 1.9 | 9.9 | |
| 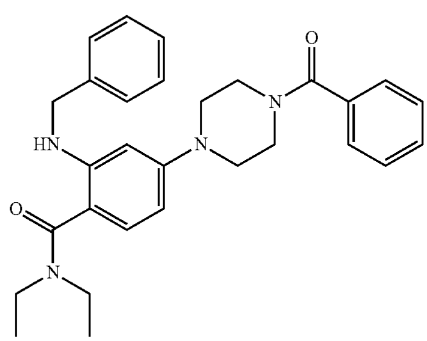 [SMILES: CCN(CC)C(=O)c1ccc(N2CCN(C(=O)c3ccccc3)CC2)cc1NCc1ccccc1] | 361 | 0.05 | |
| 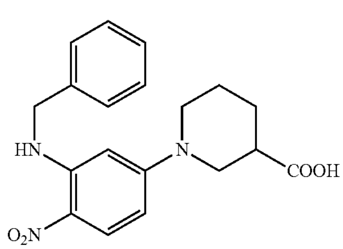 [SMILES: O=C(O)C1CCCN(c2ccc([N+](=O)[O-])c(NCc3ccccc3)c2)C1] | 21.7 | 0.88 | |

TABLE 1-continued

| Structure | Aβ-ThT (IC$_{50}$/ μM) | Ratio | A-syn (IC$_{50}$/ μM) |
|---|---|---|---|
| [structure: 3'-(phenylamino)-4'-nitro-biphenyl-3-carboxylic acid] | 9.23 | 2.3 | 10 |
| [structure: (4-(dimethylamino)-5-nitrophenyl)piperazinyl phenyl ketone] | 27 | 0.8 | 15 |
| [structure: (4-(3-nitrophenyl)piperazin-1-yl)(phenyl)methanone] | 360 | 0.06 | |
| [structure: (4-(3-aminophenyl)piperazin-1-yl)(phenyl)methanone] | 428 | 0.05 | |
| [structure: (4-(3-(phenylamino)phenyl)piperazin-1-yl)(phenyl)methanone] | 539 | 0.05 | |
| [structure: 4'-amino-3'-(phenylamino)biphenyl-3-carboxylic acid] | 26.6 | 2.5 | 45 |
| [structure: (4-(4-amino-3-(N-benzyl-N-phenylamino)phenyl)piperazin-1-yl)(phenyl)methanone] | 106.6 | 0.35 | |

TABLE 1-continued

| Structure | Aβ-ThT (IC$_{50}$/ μM) | Ratio | A-syn (IC$_{50}$/ μM) |
|---|---|---|---|
| *structure* | 148 | 0.25 | |
| *structure* | 3.5 | 11 | ~7 |
| *structure* | 15.5 | 0.65 | |
| *structure* | 7.8 | 1.3 | |
| *structure* | 2.29 | 4.4 | |
| *structure* | 90 | 0.1 | |

TABLE 1-continued

| Structure | Aβ-ThT (IC$_{50}$/ μM) | Ratio | A-syn (IC$_{50}$/ μM) |
|---|---|---|---|
| 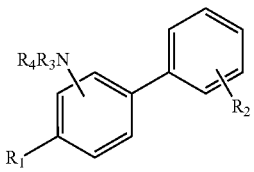 | 54.4 | 0.17 | |
| 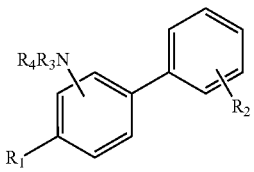 | 238.4 | 0.04 | |

This measurement indicates that many compounds listed above are potent inhibitors of beta-amyloid aggregation, and that some are also potent inhibitors of alpha-synuclein aggregation.

We claim:

1. A compound of Formula Ic or a pharmaceutically acceptable salts salt thereof:

(Ic)

wherein $R_1$ is selected from the group consisting of nitro, carboxylic acid, alkylcarboxylic acid, acetamide connected in either direction, N-(2-ethanol)amine, N-(2-morpholinethyl)amine, amine optionally substituted with one or more alkyl groups, amide optionally substituted with one or more alkyl groups, and alkoxy; $R_2$ is selected from the group consisting of carboxylic acid, alkyl, alkanoyl, alkanesulfonyl, benzenesulfonyl, phenonyl optionally substituted with any one or more of alkoxy, halogen, or alkyl groups, benzyl optionally substituted with any one or more of alkoxy, halogen, or alkyl groups, and amide optionally substituted with any one or more of alkyl or aryl groups; $R_3$ is selected from the group consisting of H, alkyl, furanoalkyl, thiophenealkyl, alkanoyl, phenyl optionally substituted with any one or more halogen, alkyl, or alkoxy groups, benzyl optionally substituted with any one or more halogen, alkyl, or alkoxy groups, and phenonyl optionally substituted with any one or more halogen, alkyl, or alkoxy groups; and $R_4$ is selected from the group consisting of H, alkyl, or phenyl optionally substituted with any one or more halogen, alkyl, or alkoxy groups.

2. The compound of claim 1, wherein $R_1$ is selected from the group consisting of nitro, acetamide connected in either direction, N-(2-ethanol) amine, amino optionally substituted with any one or more alkyl groups, and amide optionally substituted with any one or more alkyl groups;

$R_2$ is selected from the group consisting of carboxylic acid, amide optionally substituted with any one or more of alkyl, and phenonyl optionally substituted with any one or more of alkoxy or alkyl;

$R_3$ is selected from the group consisting of methyl, phenyl optionally substituted with any one or more halogen, alkyl, or alkoxy groups, benzyl optionally substituted with any one or more halogen, alkyl, or alkoxy groups, and phenonyl optionally substituted with any one or more halogen, alkyl, or alkoxy groups; and $R_4$ is selected from the group consisting of H, alkoxy, and alkyl;

with the exceptions that the compounds of Formula Ic do not include compounds wherein:

i) the $NR_3R_4$ moiety is connected ortho to the $R_1$ moiety on the phenyl ring, $R_1$ is nitro, $R_2$ is phenonyl, $R_4$ is H, and $R_3$ is selected from the group consisting of methyl and benzyl;

ii) the $NR_3R_4$ moiety is connected ortho to the $R_1$ moiety on the phenyl ring, $R_1$ is nitro, $R_2$ is phenonyl optionally substituted with any one or more of halogen, alkyl, or alkoxy, $R_4$ is H, and $R_3$ is selected from the group consisting of benzyl, (4-fluorophenyl)methyl, and (4-isopropylphenyl)methyl;

iii) $R_1$ is nitro, $R_2$ is carboxylic acid, $R_3$ is selected from the group consisting of benzyl optionally substituted with any one or more of halogen and methyl, and $R_4$ is selected from the group consisting of H and alkyl; and iv) $R_1$ is amino, $R_2$ is selected from the group consisting of alkylamide and carboxylic acid, $R_3$ is methyl, and $R_4$ is selected from the group consisting of H and alkyl.

3. The compound of claim 1, wherein $R_1$ is selected from the group consisting of nitro, acetamide connected in either direction, N-(2-ethanol)amine, amino optionally substituted with methyl or dimethyl, amide optionally substituted with methyl, ethyl, dimethyl, or diethyl, and methoxy;

$R_2$ is selected from the group consisting of phenonyl optionally substituted with any one or more of methoxy, alkyl, or halogen, amide optionally substituted with any one or more of methyl, phenyl, benzyl, or dimethyl, and carboxylic acid;

$R_3$ is selected from the group consisting of methyl, phenyl optionally substituted with any one or more of halogen, alkyl, or methoxy, benzyl optionally substituted with any one or more of halogen, alkyl, or methoxy, and phenonyl optionally substituted with any one or more of halogen, alkyl, or methoxy; and $R_4$ is selected from the group consisting of H, methyl, and phenyl optionally substituted with any one or more of halogen, alkyl, or alkoxy;

with the exceptions that compounds of Formula Ic do not include compounds wherein:

i) the $NR_3R_4$ moiety is connected ortho to the $R_1$ moiety on the phenyl ring, $R_1$ is nitro, $R_2$ is phenonyl, $R_4$ is H, and $R_3$ is selected from the group consisting of methyl and benzyl;

ii) the $NR_3R_4$ moiety is connected ortho to the $R_1$ moiety on the phenyl ring, $R_1$ is nitro, $R_2$ is phenonyl optionally substituted with any one or more of methoxy, alkyl, or hydrogen, $R_4$ is H, and $R_3$ is selected from the group consisting of (4-fluorophenyl)methyl and (4-isopropylphenyl)methyl;

iii) $R_1$ is nitro, $R_2$ is carboxylic acid, $R_3$ is selected from the group consisting of benzyl optionally substituted with any one or more of halogen and methyl, and $R_4$ is selected from the group consisting of H and methyl; and iv) $R_1$ is amino, $R_2$ is selected from the group consisting of alkylamide and carboxylic acid, $R_3$ is methyl, and $R_4$ is selected from the group consisting of H and methyl.

4. The compound of claim 1, wherein the $NR_3R_4$ moiety is connected ortho to the $R_1$ moiety on the phenyl ring; $R_1$ is selected from the group consisting of nitro, amino optionally substituted with methyl or dimethyl, and amide optionally substituted with methyl, dimethyl, ethyl, or diethyl; the $R_2$ moiety is connected meta with respect to the phenyl ring; $R_2$ is carboxylic acid; $R_3$ is selected from the group consisting of phenyl optionally substituted by any one or more of methoxy or halogen and benzyl optionally substituted by any one or more of methoxy or halogen; and $R_4$ is selected from the group consisting of H and methyl.

5. The compound of claim 1, wherein the compound is selected from the group consisting of 3'-(benzyl amino)-4'-nitrophenyl-3-carboxylic acid, 3'-(benzylamino)-4'-nitro-N-phenylbiphenyl-3-carboxamide, 4'-nitro-3'-(phenylamino) biphenyl-3-carboxylic acid, and 4'-amino-3'-(phenylamino) biphenyl-3-carboxylic acid, and pharmaceutically acceptable salts thereof.

6. The compound of claim 1, which inhibits the aggregation of an amyloidogenic protein.

7. A method of treating amyloid diseases, comprising administering a pharmaceutically effective dosage form containing a compound of claim 1 to a human.

8. The compound of claim 6, wherein said amyloid disease is selected from the group consisting of Alzheimer's disease, Parkinson's disease, Huntington's disease, and prion diseases.

9. A pharmaceutical composition, comprising a compound of claim 1 and a pharmaceutically acceptable excipient.

10. The composition of claim 9, wherein said composition is an oral dosage form.

11. The composition of claim 9, wherein said composition is a parenteral dosage form.

12. A method of treating amyloid diseases, comprising administering to a human a compound of Formula Ic or a pharmaceutically acceptable salt thereof:

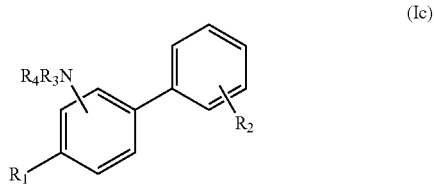

(Ic)

wherein $R_1$ is selected from the group consisting of nitro, carboxylic acid, alkylcarboxylic acid, acetamide connected in either direction, N-(2-ethanol)amine, N-(2-morpholinethyl)amine, amine optionally substituted with one or more alkyl groups, amide optionally substituted with one or more alkyl groups, and alkoxy; $R_2$ is selected from the group consisting of carboxylic acid, alkyl, alkanoyl, alkanesulfonyl, benzenesulfonyl, phenonyl optionally substituted with any one or more of alkoxy, halogen, or alkyl groups, benzyl optionally substituted with any one or more of alkoxy, halogen, or alkyl groups, and amide optionally substituted with any one or more of alkyl or aryl groups; $R_3$ is selected from the group consisting of H, alkyl, furanoalkyl, thiophenealkyl, alkanoyl, phenyl optionally substituted with any one or more halogen, alkyl, or alkoxy groups, benzyl optionally substituted with any one or more halogen, alkyl, or alkoxy groups, and phenonyl optionally substituted with any one or more halogen, alkyl, or alkoxy groups; and $R_4$ is selected from the group consisting of H, alkyl, or phenyl optionally substituted with any one or more halogen, alkyl, or alkoxy groups, in the manufacture of a dosage form for the treatment of amyloid diseases.

13. The method of claim 12, wherein $R_1$ is selected from the group consisting of nitro, acetamide connected in either direction, N-(2-ethanol)amine, amino optionally substituted with any one or more alkyl groups, and amide optionally substituted with any one or more alkyl groups; $R_2$ is selected from the group consisting of carboxylic acid, amide optionally substituted with any one or more of alkyl or aryl groups, and phenonyl optionally substituted with any one or more of alkoxy, alkyl, or aryl groups; $R_3$ is selected from the group consisting of methyl, phenyl optionally substituted with any one or more halogen, alkyl, or alkoxy groups, benzyl optionally substituted with any one or more halogen, alkyl, or alkoxy groups, and phenonyl optionally substituted with any one or more halogen, alkyl, or alkoxy groups; and $R_4$ is selected from the group consisting of H, alkoxy, and aryl.

14. The method of claim 12, wherein $R_1$ is selected from the group consisting of nitro, acetamide connected in either direction, N-(2-ethanol)amine, amino optionally substituted with methyl or dimethyl, amide optionally substituted with methyl, ethyl, dimethyl, or diethyl, and methoxy; $R_2$ is selected from the group consisting of phenonyl optionally substituted with any one or more of methoxy, alkyl, or halogen, amide optionally substituted with any one or more of methyl, phenyl, benzyl, or dimethyl, and carboxylic acid; $R_3$ is selected from the group consisting of methyl, phenyl optionally substituted with any one or more of halogen, alkyl, or methoxy, benzyl optionally substituted with any one or more of halogen, alkyl, or methoxy, and phenonyl optionally substituted with any one or more of halogen, alkyl, or methoxy; and $R_4$ is selected from the group consisting of H, methyl, and phenyl optionally substituted with any one or more of halogen, alkyl, or alkoxy.

15. The method of claim 12, wherein the $NR_3R_4$ moiety is connected ortho to the $R_1$ moiety on the phenyl ring; $R_1$ is selected from the group consisting of nitro, amino optionally substituted with methyl or dimethyl, and amide optionally substituted with methyl, dimethyl, ethyl, or diethyl; the $R_2$ moiety is connected meta with respect to the phenyl ring; $R_2$ is carboxylic acid; $R_3$ is selected from the group consisting of phenyl optionally substituted by any one or more of methoxy or halogen and benzyl optionally substituted by any one or more of methoxy or halogen; and $R_4$ is selected from the group consisting of H and methyl.

16. The method of claim 12, wherein the compound is selected from the group consisting of 3'-(benzyl amino)-4'-nitrophenyl-3-carboxylic acid, 3'-(benzylamino)-4'-nitro-N-phenylbiphenyl-3-carboxamide, 4'-nitro-3'-(phenylamino) biphenyl-3-carboxylic acid, and 4'-amino-3'-(phenylamino) biphenyl-3-carboxylic acid, pharmaceutically acceptable salts, stereo-isomers, polymorphs, metabolites, analogues, pro-drugs and combinations thereof.

17. A pharmaceutical composition, comprising a therapeutically effective amount of a compound of Formula Ic or a pharmaceutically acceptable salt thereof:

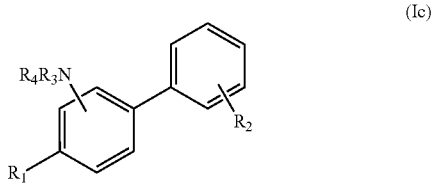

(Ic)

wherein $R_1$ is selected from the group consisting of nitro, carboxylic acid, alkylcarboxylic acid, acetamide connected in either direction, N-(2-ethanol)amine, N-(2-morpholinethyl)amine, amine optionally substituted with one or more alkyl groups, amide optionally substituted with one or more alkyl groups, and alkoxy; $R_2$ is selected from the group consisting of carboxylic acid, alkyl, alkanoyl, alkanesulfonyl, benzenesulfonyl, phenonyl optionally substituted with any one or more of alkoxy, halogen, or alkyl groups, benzyl optionally substituted with any one or more of alkoxy, halogen, or alkyl groups, and amide optionally substituted with any one or more of alkyl or aryl groups; $R_3$ is selected from the group consisting of H, alkyl, furanoalkyl, thiophenealkyl, alkanoyl, phenyl optionally substituted with any one or more halogen, alkyl, or alkoxy groups, benzyl optionally substituted with any one or more halogen, alkyl, or alkoxy groups, and phenonyl optionally substituted with any one or more halogen, alkyl, or alkoxy groups; and $R_4$ is selected from the group consisting of H, alkyl, or phenyl optionally substituted with any one or more halogen, alkyl, or alkoxy groups.

18. The pharmaceutical composition of claim 17, wherein
$R_1$ is selected from the group consisting of nitro, acetamide connected in either direction, N-(2-ethanol)amine, amino optionally substituted with any one or more alkyl groups, and amide optionally substituted with any one or more alkyl groups;

$R_2$ is selected from the group consisting of carboxylic acid, amide optionally substituted with any one or more of alkyl, and phenonyl optionally substituted with any one or more of alkoxy or alkyl;

$R_3$ is selected from the group consisting of methyl, phenyl optionally substituted with any one or more halogen, alkyl, or alkoxy groups, benzyl optionally substituted with any one or more halogen, alkyl, or alkoxy groups, and phenonyl optionally substituted with any one or more halogen, alkyl, or alkoxy groups; and $R_4$ is selected from the group consisting of H, alkoxy, and alkyl;

with the exceptions that the compounds of Formula Ic do not include compounds wherein:
i) the $NR_3R_4$ moiety is connected ortho to the $R_1$ moiety on the phenyl ring, $R_1$ is nitro, $R_2$ is phenonyl, $R_4$ is H, and $R_3$ is selected from the group consisting of methyl and benzyl;
ii) the $NR_3R_4$ moiety is connected ortho to the $R_1$ moiety on the phenyl ring, $R_1$ is nitro, $R_2$ is phenonyl optionally substituted with any one or more of halogen, alkyl, or alkoxy, $R_4$ is H, and $R_3$ is selected from the group consisting of benzyl, (4-fluorophenyl)methyl, and (4-isopropylphenyl)methyl;
iii) $R_1$ is nitro, $R_2$ is carboxylic acid, $R_3$ is selected from the group consisting of benzyl optionally substituted with any one or more of halogen and methyl, and $R_4$ is selected from the group consisting of H and alkyl; and
iv) $R_1$ is amino, $R_2$ is selected from the group consisting of alkylamide and carboxylic acid, $R_3$ is methyl, and $R_4$ is selected from the group consisting of H and alkyl.

19. The pharmaceutical composition of claim 17, wherein
$R_1$ is selected from the group consisting of nitro, acetamide connected in either direction, N-(2-ethanol)amine, amino optionally substituted with methyl or dimethyl, amide optionally substituted with methyl, ethyl, dimethyl, or diethyl, and methoxy;

$R_2$ is selected from the group consisting of phenonyl optionally substituted with any one or more of methoxy, alkyl, or halogen, amide optionally substituted with any one or more of methyl, phenyl, benzyl, or dimethyl, and carboxylic acid;

$R_3$ is selected from the group consisting of methyl, phenyl optionally substituted with any one or more of halogen, alkyl, or methoxy, benzyl optionally substituted with any one or more of halogen, alkyl, or methoxy, and phenonyl optionally substituted with any one or more of halogen, alkyl, or methoxy; and $R_4$ is selected from the group consisting of H, methyl, and phenyl optionally substituted with any one or more of halogen, alkyl, or alkoxy;

with the exceptions that compounds of Formula Ic do not include compounds wherein:

i) the $NR_3R_4$ moiety is connected ortho to the $R_1$ moiety on the phenyl ring, $R_1$ is nitro, $R_2$ is phenonyl, $R_4$ is H, and $R_3$ is selected from the group consisting of methyl and benzyl;

ii) the $NR_3R_4$ moiety is connected ortho to the $R_1$ moiety on the phenyl ring, $R_1$ is nitro, $R_2$ is phenonyl optionally substituted with any one or more of methoxy, alkyl, or hydrogen, $R_4$ is H, and $R_3$ is selected from the group consisting of (4-fluorophenyl)methyl and (4-isopropylphenyl)methyl;

iii) $R_1$ is nitro, $R_2$ is carboxylic acid, $R_3$ is selected from the group consisting of benzyl optionally substituted with any one or more of halogen and methyl, and $R_4$ is selected from the group consisting of H and methyl; and iv) $R_1$ is amino, $R_2$ is selected from the group consisting of alkylamide and carboxylic acid, $R_3$ is methyl, and $R_4$ is selected from the group consisting of H and methyl.

20. The pharmaceutical composition of claim 17, wherein the compound is selected from the group consisting of 3'-(benzyl amino)-4'-nitrophenyl-3-carboxylic acid, 3'-(benzylamino)-4'-nitro-N-phenylbiphenyl-3-carboxamide, 4'-nitro-3'-(phenylamino) biphenyl-3-carboxylic acid, and 4'-amino-3'-(phenylamino) biphenyl-3-carboxylic acid, pharmaceutically acceptable salts, stereo-isomers, polymorphs, metabolites, analogues, pro-drugs and combinations thereof.

21. The pharmaceutical composition of claim 17, which is an oral dosage form.

22. The pharmaceutical composition of claim 18, which is a parenteral dosage form.

* * * * *